(12) United States Patent
Aburatani et al.

(10) Patent No.: US 9,139,647 B2
(45) Date of Patent: Sep. 22, 2015

(54) DIAGNOSIS AND TREATMENT OF CANCER USING ANTI-TM4SF20 ANTIBODY

(75) Inventors: Hiroyuki Aburatani, Tokyo (JP); Shunpei Ishikawa, Tokyo (JP); Shigeto Kawai, Tokyo (JP)

(73) Assignees: FORERUNNER PHARMA RESEARCH CO., LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 125 days.

(21) Appl. No.: 13/138,014

(22) PCT Filed: Dec. 25, 2009

(86) PCT No.: PCT/JP2009/007237
§ 371 (c)(1),
(2), (4) Date: Sep. 9, 2011

(87) PCT Pub. No.: WO2010/073694
PCT Pub. Date: Jul. 1, 2010

(65) Prior Publication Data
US 2012/0004117 A1    Jan. 5, 2012

(30) Foreign Application Priority Data
Dec. 25, 2008 (JP) ................................. 2008-330487

(51) Int. Cl.
| | | |
|---|---|---|
| *C12P 21/08* | (2006.01) |
| *C07K 16/00* | (2006.01) |
| *C07K 16/28* | (2006.01) |
| *C07K 16/30* | (2006.01) |
| *G01N 33/574* | (2006.01) |
| *A61K 39/00* | (2006.01) |

(52) U.S. Cl.
CPC .............. *C07K 16/28* (2013.01); *C07K 16/30* (2013.01); *G01N 33/57423* (2013.01); *G01N 33/57438* (2013.01); *G01N 33/57446* (2013.01); *G01N 33/57492* (2013.01); *A61K 2039/505* (2013.01); *C07K 2317/34* (2013.01); *C07K 2317/56* (2013.01); *C07K 2317/732* (2013.01); *C07K 2317/734* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 2003/0045684 A1* | 3/2003 | Eaton et al. ................ | 530/350 |
| 2003/0105000 A1* | 6/2003 | Pero et al. .................. | 514/12 |
| 2004/0180002 A1* | 9/2004 | Young et al. ................ | 424/1.49 |
| 2006/0160186 A1 | 7/2006 | Eaton et al. | |
| 2007/0237770 A1* | 10/2007 | Lai et al. ................... | 424/138.1 |

FOREIGN PATENT DOCUMENTS

| | | |
|---|---|---|
| JP | 2004-516802 A | 6/2004 |
| JP | 2007-209214 A | 8/2007 |
| WO | 99-63088 A2 | 12/1999 |
| WO | 2006132788 | 12/2006 |

OTHER PUBLICATIONS

Rudikoff et al. (PNAS, USA, 1982, 79: 1979-1983).*
Coleman et al. (Research in Immunology, 1994; 145(1): 33-36).*
Abaza et al. (Journal of Protein Chemistry, 1992 vol. 11, No. 5: 433-444).*
Burgess et al. (J. of Cell Bio. 1990, 111:2129-2138).*
Gussow et al. (1991, Methods in Enzymology 203:99-121).*
MacCallum et al. (J. Mol. Biol. (1996) 262, 732-745).*
Gura (Science, 1997, 278:1041-1042).*
Kaiser (Science, 2006, 313: 1370).*
Transmembrane 4 L6 family member 20 (UniProtKB: locus T4S20_HUMAN, accession Q53R12, Nov. 13, 2007).*
Wright, M.D. et al. The L6 membrane proteins—A new four-transmembrane superfamily. IN: Protein Science; 2000; vol. 9; pp. 1594-1600.
Fox, C.A. et al. Altered expression of TFF-1 and CES-2 in Barrett's esophagus and associated adenocarcinomas. IN: Neoplasia; 2005; vol. 7, No. 4; pp. 407-416.
Niewold, T.A. et al. The early transcriptional response of pig small intestinal mucosa to invasion by *Salmonella enterica* serovar *typhimurium* DT104. IN: Molecular Immunology; 2007; vol. 44; pp. 1316-1322.
Tan, Y-J. et al. The severe acute respiratory syndrome coronavirus 3a protein up-regulates expression of fibrinogen in lung epithelial cells. IN: Journal of Virology; Aug. 2005; vol .79, No. 15; pp. 10083-10087.
Goodman, G.E. et al. Phase I trial of chimeric (human-mouse) monoclonal antibody L6 in patients with non-small-cell lung, colon, and breast cancer. IN: Cancer Immunology Immunotherapy; 1993; vol. 36; pp. 267-273.
Kao, Y-R. et al. Tumor-associated antigen L6 and the invasion of human lung cancer cells. IN: Clinical Cancer Research; Jul. 2003; vol. 9; pp. 2807-2816.
Wice, B.M. et al. A tetraspan membrane glycoprotein produced in the human intestinal epithelium and liver that can regulate cell density-dependent proliferation. IN: The Journal of Biological Chemistry; Sep. 15, 1995; vol. 270, No. 37; pp. 21907-21918.

(Continued)

*Primary Examiner* — Peter J Reddig
(74) *Attorney, Agent, or Firm* — Sughrue Mion, PLLC

(57) ABSTRACT

The present invention relates to an antibody binding to a TM4SF20 protein and the diagnosis and treatment of cancer using the antibody. Specifically, the present invention provides an anti-TM4SF20 antibody and a pharmaceutical composition (e.g., an anticancer agent and a diagnostic drug for cancer) comprising the antibody as an active ingredient.

8 Claims, 11 Drawing Sheets
(1 of 11 Drawing Sheet(s) Filed in Color)

(56) References Cited

OTHER PUBLICATIONS

Muller-Pillasch, F. et al. Identification of a new tumour-associated antigen TM4SF5 and its expression in human cancer. IN: Gene; vol. 208; 1998; pp. 25-30.

Hemler, M.E. Tetraspanin functions and associated microdomains. IN: Nature Reviews Molecular Cell Biology; vol. 6; Oct. 2005; pp. 801-811.

Lazo, P.A. Functional implications of tetraspanin proteins in cancer biology. IN: Cancer Science; vol. 98, No. 11; Nov. 2007; pp. 1666-1677.

Lee, S-Y. et al. Focal adhesion and actin organization by a cross-talk of TM4SF5 with integrin α2 are regulated by serum treatment. IN: Experimental Cell Research; vol. 312; 2006; pp. 2983-2999.

Lee, S-A. et al. Tetraspanin TM4SF5 mediates loss of contact inhibition through epithelial-mesenchymal transition in human hepatocarcinoma. IN: Journal of Clinical Investigation; vol. 118, No. 4; Apr. 2008; pp. 1354-1366.

Marken, J.S. et al. Cloning and expression of the tumor-associated antigen L6. IN: Procedures of National Academy of Science USA; vol. 89, No. 8; Apr. 1992; pp. 3503-3507.

Hellstrom, I. et al. Antitumor effects of L6, an IgG2a antibody that reacts with most human carcinomas. IN: Procedures of National Academy of Science USA; vol. 83, No. 18; Sep. 1986; pp. 7059-7063.

Liu, A.Y. et al. Chimeric mouse-human IgG1 antibody that can mediate lysis of cancer cells. IN: Procedures of National Academy of Science USA; vol. 84, No. 10; May 1987; pp. 3439-3443.

International Search Report for PCT/JP2009/007237; Feb. 16, 2010.

Davies et al., "Affinity improvement of single antibody VH domains: residues in all three hypervariable regions affect antigen binding", Immunotechnology. 2:169-179 (1996).

Hevel et al., "Novel functional view of the crocidolite asbestos-treated A549 human lung epithelial transcriptome reveals an intricate network of pathways with opposing functions", BMC Genomics, 9(1):376 [pp. 1-17] (2008).

Holt et al., "Domain antibodies: proteins for therapy", Trends in Biotechnology, 21(11):484-490 (2003).

Hulst et al., "Early transcriptional response in the jejunum of germ-free piglets after oral infection with virulent rotavirus", Arch. Virol., 153:1311-1322 (2008).

European Search Report for EP 09834500 dated Jul. 6, 2012, with Supplemental European Search Report dated Jun. 28, 2012.

\* cited by examiner

Bold line; B8
Solid line; B11
Dotted line; B12
Gray filled line; mIgG2a

Bold line; B15
Solid line; C7
Dotted line; C9
Gray filled line; mIgG2a

Fig.11 (A)
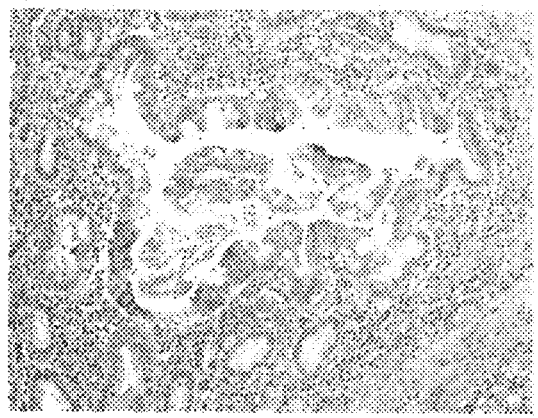
(B)
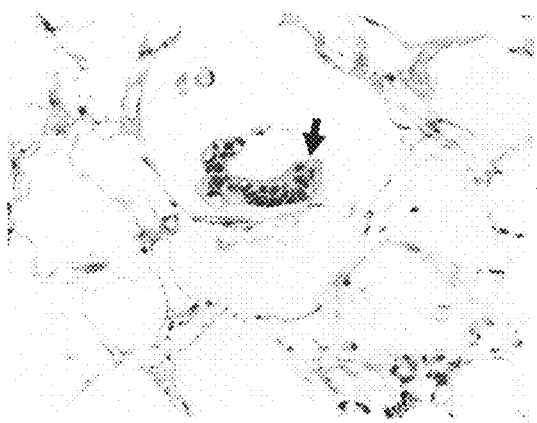
(C)
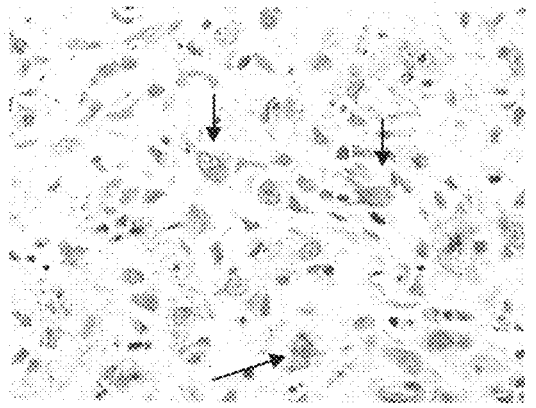

DIAGNOSIS AND TREATMENT OF CANCER USING ANTI-TM4SF20 ANTIBODY

TECHNICAL FIELD

The present invention relates to an anti-TM4SF20 antibody and the diagnosis and treatment of cancer using the antibody.

BACKGROUND ART

Transmembrane 4 L6 family member 20 (TM4SF20) is a four-transmembrane protein expressed on a cell membrane and belongs to the L6 tetraspanin family. TM4SF1 (L6), TM4SF4 (ILTMP), TM4SF5, and the like are known as members of the L6 tetraspanin family. All of them are 4-transmembrane proteins which have a short intracellular region at the N and C termini and have a short extracellular region between a transmembrane region 1 (TM1) and TM2 and a long extracellular region between TM3 and TM4 (Non Patent Literature 1). TM4SF1 is expressed in lung cancer, colon cancer, breast cancer, and ovarian cancer, and the clinical tests of anticancer agents have been practiced using an anti-TM4SF1 antibody (Non Patent Literature 2). Moreover, the anti-TM4SF1 antibody is known to reduce the invasive capacity of lung cancer cells (Non Patent Literature 3). TM4SF4 has been reported to be expressed on the luminal side of intestinal epithelial cells (Non Patent Literature 4). TM4SF5 has been found as a molecule highly expressed in pancreatic cancer (Non Patent Literature 5).

While the L6 tetraspanin family belongs to the tetraspanin superfamily, many members of the tetraspanin superfamily are known to bind to integrin (Non Patent Literatures 6 and 7). TM4SF5 is also known to bind to integrin α2 and further induce EMT (epithelial-mesenchymal transition) by focal adhesion kinase-mediated signal transduction (Non Patent Literatures 8 and 9).

For TM4SF20, its enhanced expression is known in Barrett's esophagus, in the swine small intestine infected with *Salmonella*, and in a human lung cancer cell line A549 expressing severe acute respiratory syndrome (SARS) virus proteins (Non Patent Literatures 10 to 12). According to reports, its expression is reduced in stomach cancer among cancers (Patent Literature 1). On the other hand, a patent application has reported use of TM4SF20 as an insulin secretion inducer (Patent Literature 2). However, there are few reports as to TM4SF20, and its physiological functions or expression specific for cancer tissues have not been reported so far.

CITATION LIST

Patent Literature

Patent Literature 1: U.S. Patent Publication No. 2006/0160186A1
Patent Literature 2: Japanese Patent Laid-Open No. 2007-209214

Non Patent Literature

Non Patent Literature 1: The L6 membrane proteins—a new four—transmembrane superfamily. Protein Sci 2000; 9:1594
Non Patent Literature 2: Phase I trial of chimeric (human-mouse) monoclonal antibody L6 in patients with non-small—cell lung, colon, and breast cancer. Cancer Immunol Immunother 1993; 36:267
Non Patent Literature 3: Tumor-associated antigen L6 and the invasion of human lung cancer cells. Clin Cancer Res 2003; 9:2807
Non Patent Literature 4: A tetraspan membrane glycoprotein produced in the human intestinal epithelium and liver that can regulate cell density-dependent proliferation. J Biol Chem 1995; 270:21907
Non Patent Literature 5: Identification of a new tumour-associated antigen TM4SF5 and its expression in human cancer. Gene 1998; 208:25
Non Patent Literature 6: Tetraspanin functions and associated microdomains. Nat Rev Mol Cell Biol 2005; 6:801
Non Patent Literature 7: Functional implications of tetraspanin proteins in cancer biology. Cancer Sci 2007; 98:1666
Non Patent Literature 8: Focal adhesion and actin organization by a cross-talk of TM4SF5 with integrin alpha2 are regulated by serum treatment. Exp Cell Res 2006; 312:2983
Non Patent Literature 9: Tetraspanin TM4SF5 mediates loss of contact inhibition through epithelial-mesenchymal transition in human hepatocarcinoma. J Clin Invest 2008; 118:1354
Non Patent Literature 10: Altered expression of TFF-1 and CES-2 in Barrett's Esophagus and associated adenocarcinomas. Neoplasia 2005; 7:407
Non Patent Literature 11: The early transcriptional response of pig small intestinal mucosa to invasion by *Salmonella enterica* serovar typhimurium DT104. Mol Immunol 2007; 44:1316
Non Patent Literature 12: The severe acute respiratory syndrome coronavirus 3a protein up-regulates expression of fibrinogen in lung epithelial cells. J Virol 2005; 79:10083

SUMMARY OF INVENTION

Technical Problem

An object of the present invention is to elucidate the in vivo expression and functions of TM4SF20 and to study its availability as a novel molecular target in the treatment and diagnosis of cancer.

Solution to Problem

The present inventors have found by gene expression analysis using microarrays that TM4SF20 mRNA is expressed in stomach cancer, lung adenocarcinoma, pancreatic cancer, and colon cancer tissues but hardly expressed in normal tissues other than the small intestine and the fetal large intestine. Moreover, as a result of analysis using immunohistochemical staining, TM4SF20 proteins have been detected on the cell membrane of clinical stomach cancer samples (adenocarcinoma and signet ring cell carcinoma). The present inventors have further prepared an anti-TM4SF20 monoclonal antibody and examined its activity against cancer cells. As a result, the anti-TM4SF20 antibody has been confirmed to bind to a human lung adenocarcinoma cell line A549 and kill the human lung adenocarcinoma cells by antibody-dependent cellular cytotoxicity (ADCC) and complement-dependent cytotoxicity (CDC). These findings show that the anti-TM4SF20 antibody is useful in the treatment and diagnosis of TM4SF20-expressing cancer such as stomach cancer, lung adenocarcinoma, pancreatic cancer, and colon cancer.

The present invention has been achieved based on these findings and provides the following [1] to [20]:

[1]
An antibody binding to a TM4SF20 protein.

[2]
The antibody according to [1], wherein the antibody has cytotoxic activity.

[3]
The antibody according to [2], wherein the cytotoxic activity is antibody-dependent cellular cytotoxicity (ADCC activity).

[4]
The antibody according to [2], wherein the cytotoxic activity is complement-dependent cytotoxicity (CDC activity).

[5]
An antibody selected from the followings:
(1) an antibody comprising a heavy chain variable region comprising heavy chain CDR1 having the amino acid sequence represented by SEQ ID NO: 79, heavy chain CDR2 having the amino acid sequence represented by SEQ ID NO: 80, and heavy chain CDR3 having the amino acid sequence represented by SEQ ID NO: 81 (B8);
(2) an antibody comprising a heavy chain variable region comprising heavy chain CDR1 having the amino acid sequence represented by SEQ ID NO: 85, heavy chain CDR2 having the amino acid sequence represented by SEQ ID NO: 86, and heavy chain CDR3 having the amino acid sequence represented by SEQ ID NO: 87 (B11);
(3) an antibody comprising a heavy chain variable region comprising heavy chain CDR1 having the amino acid sequence represented by SEQ ID NO: 91, heavy chain CDR2 having the amino acid sequence represented by SEQ ID NO: 92, and heavy chain CDR3 having the amino acid sequence represented by SEQ ID NO: 93 (B12);
(4) an antibody comprising a heavy chain variable region comprising heavy chain CDR1 having the amino acid sequence represented by SEQ ID NO: 97, heavy chain CDR2 having the amino acid sequence represented by SEQ ID NO: 98, and heavy chain CDR3 having the amino acid sequence represented by SEQ ID NO: 99 (B15);
(5) an antibody comprising a heavy chain variable region comprising heavy chain CDR1 having the amino acid sequence represented by SEQ ID NO: 103, heavy chain CDR2 having the amino acid sequence represented by SEQ ID NO: 104, and heavy chain CDR3 having the amino acid sequence represented by SEQ ID NO: 105 (C7);
(6) an antibody comprising a heavy chain variable region comprising heavy chain CDR1 having the amino acid sequence represented by SEQ ID NO: 109, heavy chain CDR2 having the amino acid sequence represented by SEQ ID NO: 110, and heavy chain CDR3 having the amino acid sequence represented by SEQ ID NO: 111 (C9);
(7) an antibody comprising a light chain variable region comprising light chain CDR1 having the amino acid sequence represented by SEQ ID NO: 82, light chain CDR2 having the amino acid sequence represented by SEQ ID NO: 83, and light chain CDR3 having the amino acid sequence represented by SEQ ID NO: 84 (B8);
(8) an antibody comprising a light chain variable region comprising light chain CDR1 having the amino acid sequence represented by SEQ ID NO: 88, light chain CDR2 having the amino acid sequence represented by SEQ ID NO: 89, and light chain CDR3 having the amino acid sequence represented by SEQ ID NO: 90 (B11);
(9) an antibody comprising a light chain variable region comprising light chain CDR1 having the amino acid sequence represented by SEQ ID NO: 94, light chain CDR2 having the amino acid sequence represented by SEQ ID NO: 95, and light chain CDR3 having the amino acid sequence represented by SEQ ID NO: 96 (B12);
(10) an antibody comprising a light chain variable region comprising light chain CDR1 having the amino acid sequence represented by SEQ ID NO: 100, light chain CDR2 having the amino acid sequence represented by SEQ ID NO: 101, and light chain CDR3 having the amino acid sequence represented by SEQ ID NO: 102 (B15);
(11) an antibody comprising a light chain variable region comprising light chain CDR1 having the amino acid sequence represented by SEQ ID NO: 106, light chain CDR2 having the amino acid sequence represented by SEQ ID NO: 107, and light chain CDR3 having the amino acid sequence represented by SEQ ID NO: 108 (C7);
(12) an antibody comprising a light chain variable region comprising light chain CDR1 having the amino acid sequence represented by SEQ ID NO: 112, light chain CDR2 having the amino acid sequence represented by SEQ ID NO: 113, and light chain CDR3 having the amino acid sequence represented by SEQ ID NO: 114 (C9);
(13) an antibody comprising the heavy chain variable region of the antibody (1) and the light chain variable region of the antibody (7) (B8);
(14) an antibody comprising the heavy chain variable region of the antibody (2) and the light chain variable region of the antibody (8) (B11);
(15) an antibody comprising the heavy chain variable region of the antibody (3) and the light chain variable region of the antibody (9) (B12);
(16) an antibody comprising the heavy chain variable region of the antibody (4) and the light chain variable region of the antibody (10) (B15);
(17) an antibody comprising the heavy chain variable region of the antibody (5) and the light chain variable region of the antibody (11) (C7);
(18) an antibody comprising the heavy chain variable region of the antibody (6) and the light chain variable region of the antibody (12) (C9);
(19) an antibody derived from any antibody of (1) to (18) by the substitution, deletion, addition, and/or insertion of one or more amino acid(s), wherein the antibody has activity equivalent to that of the any antibody of (1) to (18); and
(20) an antibody binding to the same epitope as that via which any antibody of (1) to (18) binds to the TM4SF20 protein.

[6]
The antibody according to any of [1] to [5], wherein the antibody recognizes the second loop of the TM4SF20 protein comprising amino acids 168-184 in the amino acid sequence of SEQ ID NO: 116.

[7]
A pharmaceutical composition comprising an antibody according to any of [1] to [5] as an active ingredient.

[8]
The pharmaceutical composition according to [7], wherein the pharmaceutical composition is an anticancer agent.

[9]
The pharmaceutical composition according to [8], wherein the pharmaceutical composition is used in the treatment of cancer selected from stomach cancer, lung adenocarcinoma, pancreatic cancer, and colon cancer.

[10]
A method for diagnosing cancer, comprising the following steps:
(a) preparing a sample isolated from a test subject; and
(b) detecting the expression level of a TM4SF20 protein or a TM4SF20 gene in the sample.

[11]

The diagnosis method according to [10], wherein the diagnosis method is intended for the diagnosis of cancer selected from stomach cancer, lung adenocarcinoma, pancreatic cancer, and colon cancer.

[12]

A diagnostic drug for cancer comprising an antibody according to any of [1] to [6].

[13]

The diagnostic drug according to [12], wherein the diagnostic drug is intended for the diagnosis of cancer selected from stomach cancer, lung adenocarcinoma, pancreatic cancer, and colon cancer.

Advantageous Effects of Invention

The present invention provides novel means for the treatment and diagnosis of cancer, particularly, stomach cancer, lung adenocarcinoma, pancreatic cancer, and colon cancer.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 11 is diagram showing results of evaluating TM4SF20 protein expression in clinical stomach cancer samples by immunohistochemical staining. Adenocarcinomas of the stomach (FIGS. 11(A) and 11(B)) and signet ring cell carcinoma of the stomach (FIG. 11(C)) were used.

Figure 1:
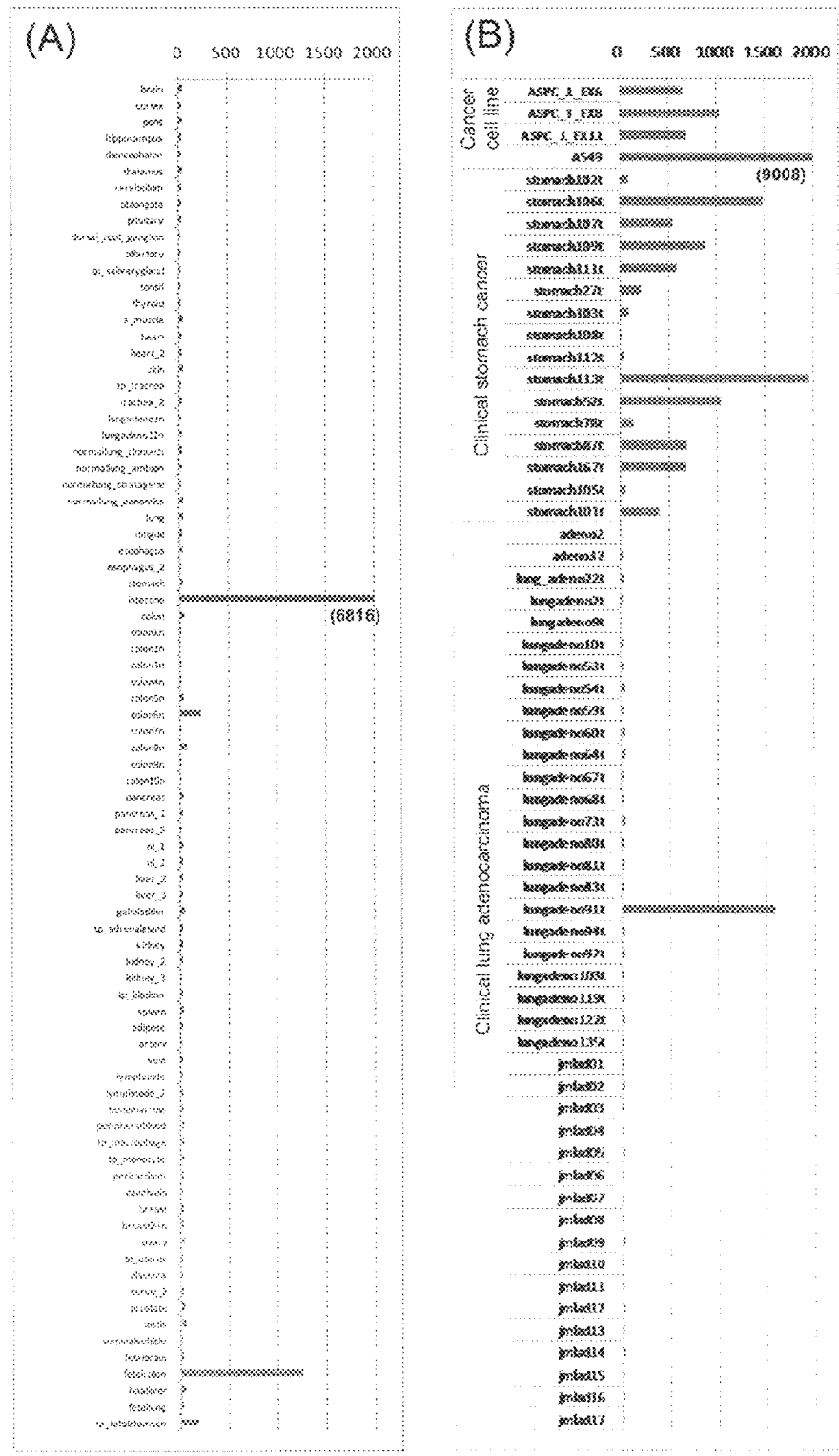
FIG. 1 is a diagram showing the expression profile of TM4SF20 mRNA in normal tissues (A) and cancers (B) obtained using Human Exon 1.0 ST Array.

The present specification encompasses the contents described in the specification of Japanese Patent Application No. 2008-330487 that serves as a basis for the priority of the present application.

DESCRIPTION OF EMBODIMENTS

1. TM4SF20

Transmembrane 4 L6 family member 20 (TM4SF20) according to the present invention is a four-transmembrane protein expressed on a cell membrane and belongs to the L6 tetraspanin family. Members of the L6 tetraspanin family include TM4SF1 (L6), TM4SF4 (ILTMP), TM4SF5, and the like. All of them are 4-transmembrane proteins which have a short intracellular region at the N and C termini and have a short extracellular region between a transmembrane region 1 (TM1) and TM2 and a long extracellular region between TM3 and TM4.

The origin of the TM4SF20 protein used in the present invention is not particularly limited, and any of TM4SF20 proteins known in the art can be used. Preferably, the TM4SF20 protein is human TM4SF20. The amino acid sequence of human TM4SF20 and a nucleotide sequence encoding this are known in the art and registered in a public database such as GenBank or Unigene, for example, as GenBank Accession No: NM_024795 (nucleotide sequence=SEQ ID NO: 115, amino acid sequence=SEQ ID NO: 116) or UniProtKB; Q53R12.

As a result of expression analysis using microarrays, the present inventors have found that TM4SF20 mRNA is expressed in stomach cancer, lung adenocarcinoma, pancreatic cancer, and colon cancer tissues but hardly expressed in normal tissues other than the small intestine and the fetal large intestine. Moreover, as a result of immunohistochemical analysis, the present inventors have confirmed that TM4SF20 proteins are present on the cell membrane of clinical stomach cancer samples (adenocarcinoma and signet ring cell carcinoma).

2. Anti-TM4SF20 Antibody

An anti-TM4SF20 antibody used in the present invention is not limited by its origin, type, shape, and the like as long as the anti-TM4SF20 antibody binds to the TM4SF20 protein. Specifically, antibodies known in the art can be used, such as non-human animal antibodies (e.g., mouse, rat, and camel antibodies), human antibodies, chimeric antibodies, and humanized antibodies. The anti-TM4SF20 antibody used in the present invention may be a polyclonal or monoclonal antibody and is preferably a monoclonal antibody. It is preferred that the antibody should bind to the TM4SF20 protein with high specificity. More preferably, its binding is particularly specific for human TM4SF20.

The anti-TM4SF20 antibody used in the present invention can be obtained as a polyclonal or monoclonal antibody using means known in the art. The anti-TM4SF20 antibody used in the present invention is particularly preferably a mammal-derived monoclonal antibody. The mammal-derived monoclonal antibody encompasses, for example, those produced by hybridomas and those produced by hosts transformed with expression vectors comprising the antibody gene by a genetic engineering approach.

The anti-TM4SF20 antibody of the present invention may be modified with various molecules such as polyethylene glycol (PEG). Moreover, the anti-TM4SF20 antibody of the present invention may be modified with a chemotherapeutic agent, a radioactive chemical, or the like, having cytotoxic activity, as described later.

Examples of the antibody that recognizes TM4SF20, used in the present invention, can include the following antibodies:

(1) an antibody comprising a heavy chain variable region comprising heavy chain CDR1 having the amino acid sequence represented by SEQ ID NO: 79, heavy chain CDR2 having the amino acid sequence represented by SEQ ID NO: 80, and heavy chain CDR3 having the amino acid sequence represented by SEQ ID NO: 81 (B8);

(2) an antibody comprising a heavy chain variable region comprising heavy chain CDR1 having the amino acid sequence represented by SEQ ID NO: 85, heavy chain CDR2 having the amino acid sequence represented by SEQ ID NO: 86, and heavy chain CDR3 having the amino acid sequence represented by SEQ ID NO: 87 (B11);

(3) an antibody comprising a heavy chain variable region comprising heavy chain CDR1 having the amino acid sequence represented by SEQ ID NO: 91, heavy chain CDR2 having the amino acid sequence represented by SEQ ID NO: 92, and heavy chain CDR3 having the amino acid sequence represented by SEQ ID NO: 93 (B12);

(4) an antibody comprising a heavy chain variable region comprising heavy chain CDR1 having the amino acid sequence represented by SEQ ID NO: 97, heavy chain CDR2 having the amino acid sequence represented by SEQ ID NO: 98, and heavy chain CDR3 having the amino acid sequence represented by SEQ ID NO: 99 (B15);

(5) an antibody comprising a heavy chain variable region comprising heavy chain CDR1 having the amino acid sequence represented by SEQ ID NO: 103, heavy chain CDR2 having the amino acid sequence represented by SEQ ID NO: 104, and heavy chain CDR3 having the amino acid sequence represented by SEQ ID NO: 105 (C7);

(6) an antibody comprising a heavy chain variable region comprising heavy chain CDR1 having the amino acid sequence represented by SEQ ID NO: 109, heavy chain CDR2 having the amino acid sequence represented by SEQ ID NO: 110, and heavy chain CDR3 having the amino acid sequence represented by SEQ ID NO: 111 (C9);

(7) an antibody comprising a light chain variable region comprising light chain CDR1 having the amino acid sequence represented by SEQ ID NO: 82, light chain CDR2 having the amino acid sequence represented by SEQ ID NO: 83, and light chain CDR3 having the amino acid sequence represented by SEQ ID NO: 84 (B8);

(8) an antibody comprising a light chain variable region comprising light chain CDR1 having the amino acid sequence represented by SEQ ID NO: 88, light chain CDR2 having the amino acid sequence represented by SEQ ID NO: 89, and light chain CDR3 having the amino acid sequence represented by SEQ ID NO: 90 (B11);

(9) an antibody comprising a light chain variable region comprising light chain CDR1 having the amino acid sequence represented by SEQ ID NO: 94, light chain CDR2 having the amino acid sequence represented by SEQ ID NO: 95, and light chain CDR3 having the amino acid sequence represented by SEQ ID NO: 96 (B12);

(10) an antibody comprising a light chain variable region comprising light chain CDR1 having the amino acid sequence represented by SEQ ID NO: 100, light chain CDR2 having the amino acid sequence represented by SEQ ID NO: 101, and light chain CDR3 having the amino acid sequence represented by SEQ ID NO: 102 (B15);

(11) an antibody comprising a light chain variable region comprising light chain CDR1 having the amino acid sequence represented by SEQ ID NO: 106, light chain CDR2 having the amino acid sequence represented by SEQ ID NO: 107, and light chain CDR3 having the amino acid sequence represented by SEQ ID NO: 108 (C7);

(12) an antibody comprising a light chain variable region comprising light chain CDR1 having the amino acid sequence represented by SEQ ID NO: 112, light chain CDR2 having the amino acid sequence represented by SEQ ID NO: 113, and light chain CDR3 having the amino acid sequence represented by SEQ ID NO: 114 (C9);

(13) an antibody comprising the heavy chain variable region of the antibody (1) and the light chain variable region of the antibody (7) (B8);

(14) an antibody comprising the heavy chain variable region of the antibody (2) and the light chain variable region of the antibody (8) (B11);

(15) an antibody comprising the heavy chain variable region of the antibody (3) and the light chain variable region of the antibody (9) (B12);

(16) an antibody comprising the heavy chain variable region of the antibody (4) and the light chain variable region of the antibody (10) (B15);

(17) an antibody comprising the heavy chain variable region of the antibody (5) and the light chain variable region of the antibody (11) (C7);

(18) an antibody comprising the heavy chain variable region of the antibody (6) and the light chain variable region of the antibody (12) (C9);

(19) an antibody derived from any antibody of (1) to (18) by the substitution, deletion, addition, and/or insertion of one or more amino acid(s), wherein the antibody has activity equivalent to that of the any antibody of (1) to (18); and

(20) an antibody binding to the same epitope as that via which any antibody of (1) to (18) binds to the TM4SF20 protein.

In the present invention, the phrase "having activity equivalent to that of the antibody of the present invention" refers to having avidity to TM4SF20 and/or cytotoxic activity (ADCC activity, CDC activity, etc.) against TM4SF20-expressing cells equivalent to those of the antibody of the present invention. In the present invention, the equivalent avidity or the equivalent cytotoxic activity is not necessarily required to be identical activity and needs only to be, for example, 50% or more, preferably 70% or more, more preferably 90% or more activity compared to that of any antibody of (1) to (18). The upper limit of the activity is not particularly limited, and examples thereof can include 1000% or less, 500% or less, 300% or less, 150% or less, and 100% or less.

In the present invention, the antibody derived from the antibody of the present invention by the substitution, deletion, addition, and/or insertion of one or more amino acid(s) may be prepared artificially or may naturally occur. A method for introducing a mutation to polypeptides is one of methods well known by those skilled in the art for preparing polypeptides functionally equivalent to certain polypeptides. For example, those skilled in the art can prepare an antibody functionally equivalent to the antibody of the present invention by appropriately introducing a mutation to the antibody of the present invention using site-directed mutagenesis (Hashimoto-Gotoh, T. et al. (1995) Gene 152, 271-275; Zoller, M J, and Smith, M. (1983) Methods Enzymol. 100, 468-500; Kramer, W. et al. (1984) Nucleic Acids Res. 12, 9441-9456; Kramer W, and Fritz H J (1987) Methods. Enzymol. 154, 350-367; Kunkel, T A (1985) Proc Natl Acad Sci USA. 82, 488-492; and Kunkel (1988) Methods Enzymol. 85, 2763-2766) or the like. Moreover, such an amino acid mutation can occur in the natural world. Such an antibody which has an amino acid sequence derived from the amino acid sequence of the antibody of the present invention by the mutation of one or more amino acid(s) and is functionally equivalent to the antibody of the present invention is also encompassed by the antibody of the present invention.

In such a variant, the number of amino acids to be varied is usually within 50 amino acids, preferably within 30 amino acids, more preferably within 10 amino acids (e.g., within 5 amino acids).

For amino acid residues to be varied, it is preferred that this mutation should be performed conservatively between amino acids having the same side chain property. For example, the following classification has been established based on the properties of amino acid side chains:
hydrophobic amino acids (A, I, L, M, F, P, W, Y, and V),
hydrophilic amino acids (R, D, N, C, E, Q, G, H, K, S, and T),
amino acids having an aliphatic side chain (G, A, V, L, I, and P),
amino acids having a hydroxyl group-containing side chain (S, T, and Y),
amino acids having a sulfur atom-containing side chain (C and M),
amino acids having a carboxylic acid- and amide-containing side chain (D, N, E, and Q),
amino acids having a base-containing side chain (R, K, and H), and
amino acids having an aromatic group-containing side chain (H, F, Y, and W).
(All the symbols within the parentheses represent a single-character code for each amino acid)

It is already known that a polypeptide having an amino acid sequence modified from a certain amino acid sequence by the deletion and/or addition of one or more amino acid residue(s) and/or by the substitution by other amino acids maintains its biological activity (Mark, D. F. et al., Proc. Natl. Acad. Sci. USA (1984) 81, 5662-5666; Zoller, M. J. and Smith, M., Nucleic Acids Research (1982) 10, 6487-6500; Wang, A. et al., Science 224, 1431-1433; and Dalbadie-McFarland, G. et al., Proc. Natl. Acad. Sci. USA (1982) 79, 6409-6413). Specifically, when an amino acid in an amino acid sequence constituting a certain polypeptide is substituted by an amino acid classified into the same group thereas, it is allegedly highly probable that the polypeptide maintains the activity. In the present invention, the substitution between amino acids within each of the amino acid groups is referred to as conservative substitution.

Moreover, the present invention also provides an antibody binding to the same epitope as that to which any antibody of (1) to (18) binds. Specific examples of the antibodies (1) to (18) can include B8, B11, B12, B15, C7, and C9 described in Examples of the present application. Specifically, the present invention also provides an antibody which recognizes the same epitope as that recognized by B8, B11, B12, B15, C7, or C9. Such an antibody can be obtained, for example, by a method shown below.

Whether an antibody to be tested and a certain antibody share an epitope can be confirmed based on their competition for the same epitope. The competition between the antibodies is detected by cross-blocking assay or the like. For example, competitive ELISA assay is preferable cross-blocking assay.

Specifically, in the cross-blocking assay, TM4SF20 proteins coated on the wells of a microtiter plate are preincubated in the presence or absence of a candidate competing antibody, and the anti-TM4SF20 antibody of the present invention is then added to the wells. The amount of the anti-TM4SF20 antibody of the present invention bound to the TM4SF20 protein in the well indirectly correlates with the binding capability of the candidate competing antibody (antibody to be tested) that competes therewith for the binding to the same epitope. Specifically, the larger affinity the antibody to be tested has for the same epitope, the smaller amount of the anti-TM4SF20 antibody of the present invention is bound to the TM4SF20 protein-coated well while the larger amount of the antibody to be tested is bound to the TM4SF20 protein-coated well.

The amount of the antibody bound to the well can be measured easily by labeling the antibody in advance. For example, a biotin-labeled antibody can be measured by use of an avidin-peroxidase conjugate and an appropriate substrate. The cross-blocking assay using enzyme (e.g., peroxidase) labeling is particularly referred to as competitive ELISA assay. The antibody can be labeled with other detectable or measurable labeling substances. Specifically, radiolabeling, fluorescent labeling, or the like is known in the art.

Furthermore, when the antibody to be tested has constant regions derived from a species different from that of the anti-TM4SF20 antibody of the present invention, the amount of any antibody bound to the well can also be measured using a labeled antibody that recognizes any constant region. Alternatively, even antibodies differing in class, albeit derived from the same species, can be measured for their respective amounts bound to the well using antibodies that discriminate each class.

Provided that the candidate competing antibody can block the binding of the anti-TM4SF20 antibody by at least 20%, preferably at least 30%, more preferably at least 50%, compared to the avidity obtained in the control test performed in the absence of the candidate competing antibody, this candidate competing antibody is determined as an antibody that binds to substantially the same epitope as that to which the anti-TM4SF20 antibody of the present invention binds or as an antibody that competes therewith for the binding to the same epitope.

For this epitope assay, the constant region of the anti-TM4SF20 antibody of the present invention may be substituted by the same constant region as that of the antibody to be tested.

Moreover, examples of a preferable aspect of the antibody of the present invention can include an antibody which recognizes the second loop of TM4SF20. The second loop of TM4SF20 refers to a region from amino acids 105 to 185 in the amino acid sequence of SEQ ID NO: 116 (TM4SF20).

Furthermore, examples of another preferable aspect of the antibody of the present invention can include an antibody which recognizes a region from amino acids 168 to 184 in the amino acid sequence of SEQ ID NO: 116 (TM4SF20).

Such an antibody has high cytotoxic activity and as such, is useful as a pharmaceutical drug, particularly, an anticancer agent. The antibody, when administered to humans, can be converted to a genetically recombinant antibody that has been engineered artificially, for example, for the purpose of reducing heteroantigenicity in humans. The genetically recombinant antibody encompasses, for example, chimeric antibodies and humanized antibodies. These engineered antibodies can be produced using a method known in the art.

(1) Chimeric Antibody

The chimeric antibodies refer to antibodies comprising variable and constant regions of different origins ligated with each other. For example, mouse-human heterogeneous chimeric antibodies are antibodies comprising the heavy and light chain variable regions of a mouse antibody and the heavy and light chain constant regions of a human antibody. Mouse antibody variable region-encoding DNAs are ligated with human antibody constant region-encoding DNAs, and the ligation products can be incorporated into expression vectors to prepare chimeric antibody-expressing recombinant vectors. Cells transformed with these vectors (recombinant cells) can be cultured for the expression of the DNA insert to obtain the chimeric antibodies produced during the culture. Human antibody C regions are used as the C regions of the chimeric antibodies and the humanized antibodies.

For example, Cγ1, Cγ2, Cγ3, Cγ4, Cμ, Cδ, Cα1, Cα2, and Cε can be used as H chain C regions. Moreover, Cκ and Cλ can be used as L chain C regions. The amino acid sequences of these C regions and nucleotide sequences encoding them are known in the art. Moreover, one or more amino acid(s) in the human antibody C regions can be substituted, deleted, added, and/or inserted for improving the stability of the antibody itself or its production.

In addition to the mouse antibodies, antibodies derived from animals such as rats, rabbits, goats, sheep, camels, and monkeys can be used. Their sequences are known in the art. Moreover, the C regions can be modified for improving the stability of the antibody or its production.

(2) Humanized Antibody

In general, the chimeric antibodies comprise non-human animal-derived antibody V regions and human antibody-derived C regions. By contrast, the humanized antibodies comprise non-human animal-derived antibody complementarity-determining regions (CDRs), human antibody-derived framework regions (FRs), and human antibody-derived C regions. The humanized antibodies are useful as active ingredients for a therapeutic agent of the present invention, owing to their reduced antigenicity in the human body.

Each antibody variable region usually comprises 3 CDRs flanked by 4 FRs. The CDR regions substantially determine the binding specificity of the antibody. The CDRs have diverse amino acid sequences. On the other hand, amino acid sequences constituting the FRs often exhibit high homology among antibodies having different binding specificities. Therefore, in general, the binding specificity of a certain antibody can allegedly be transplanted to other antibodies through CDR grafting.

The humanized antibodies are also called reshaped human antibodies. Specifically, for example, humanized antibodies comprising non-human animal (e.g., mouse) antibody CDRs grafted in human antibodies are known in the art. General gene recombination approaches are also known for obtaining the humanized antibodies.

Specifically, for example, Overlap Extension PCR is known in the art as a method for grafting mouse antibody CDRs into human FRs. In the Overlap Extension PCR, a nucleotide sequence encoding each mouse antibody CDR to be grafted is added to primers for human antibody FR synthesis. The primers are prepared for each of the 4 FRs. In the mouse CDR grafting into the human FRs, in general, it is allegedly advantageous to select human FRs highly homologous to mouse FRs for maintaining the CDR functions. Specifically, it is generally preferred to use human FRs comprising amino acid sequences highly homologous to those of the FRs adjacent to the mouse CDRs to be grafted.

Moreover, the nucleotide sequences to be ligated are designed such that they are connected in frame. The human FRs are individually synthesized using their respective primers. As a result, products are obtained, which comprise the mouse CDR-encoding DNA added to each FR-encoding sequence. The mouse CDR-encoding nucleotide sequence in each product is designed such that the nucleotide sequence overlaps with another. Subsequently, the overlapping CDR portions in the products synthesized with human antibody genes as templates are annealed to each other for complementary strand synthesis reaction. Through this reaction, the human FR sequences are ligated via the mouse CDR sequences.

Finally, the full length of the gene of the V region comprising 3 CDRs and 4 FRs ligated is amplified with primers that respectively anneal to the 5' and 3' ends thereof and comprise an added recognition sequence for an appropriate restriction enzyme. The DNA thus obtained and human antibody C region-encoding DNA can be inserted into expression vectors such that they are fused in frame to prepare vectors for human antibody expression. These vectors are introduced into hosts to establish recombinant cells, which are then cultured for the expression of the humanized antibody-encoding DNA to produce the humanized antibodies into the cultures of the cultured cells (see European Patent Publication No. EP 239400 and International Publication No. WO 96/02576).

The humanized antibodies thus prepared can be evaluated for their avidities for the antigen by qualitative or quantitative assay to preferably select human antibody FRs that allow CDRs to form a favorable antigen-binding site when ligated via the CDRs. If necessary, FR amino acid residue(s) may be substituted such that the CDRs of the humanized antibody form an appropriate antigen-binding site. For example, a mutation can be introduced in the amino acid sequence of FR by applying the PCR method used in the mouse CDR grafting into the human FRs. Specifically, a mutation of a partial nucleotide sequence can be introduced in the primers annealing to the FR nucleotide sequence. The FR nucleotide sequence synthesized using such primers contains the mutation thus introduced. The variant antibodies having the substituted amino acid(s) can be evaluated for their avidities for the antigen by the same assay as above to select variant FR sequences having the desired property (Sato, K. et al., Cancer Res, 1993, 53, 851-856).

(3) Low-Molecular Antibody

The antibody of the present invention encompasses not only bivalent antibodies typified by IgG (IgG1, IgG2, IgG4, etc.) but also monovalent antibodies or polyvalent antibodies typified by IgM as long as these antibodies bind to the TM4SF20 protein. The polyvalent antibody of the present invention encompasses polyvalent antibodies having antigen-binding sites, all of which are the same as each other or some or all of which are different from each other. The antibody of the present invention is not limited to whole antibody molecules and may be a low-molecular antibody or a modified form thereof as long as the antibody binds to the TM4SF20 protein.

The low-molecular antibody encompasses an antibody fragment deficient in a portion of the whole antibody (e.g., whole IgG). Such partial deficiency of the antibody molecule is accepted as long as the resultant antibody fragment is capable of binding to the TM4SF20 antigen. It is preferred that the antibody fragment according to the present invention should contain one or both of heavy chain variable (VH) and light chain variable (VL) regions. It is also preferred that the antibody fragment according to the present invention should contain CDRs. The number of CDRs contained in the antibody fragment of the present invention is not particularly limited and is preferably at least 6 CDRs: heavy chain CDR1, CDR2, and CDR3 and light chain CDR1, CDR2, and CDR3.

The amino acid sequence of VH or VL can contain substitution, deletion, addition, and/or insertion. Furthermore, the antibody fragment of the present invention may be deficient in a portion of one or both of VH and VL as long as the resultant antibody fragment is capable of binding to the TM4SF20 antigen. Moreover, its variable region may be chimerized or humanized. Specific examples of the antibody fragment can include Fab, Fab', F(ab')2, and Fv. Moreover, specific examples of the low-molecular antibody can include Fab, Fab', F(ab')2, Fv, scFv (single chain Fv), Diabody, sc(Fv)2 (single chain (Fv)2), and scFv-Fc. These antibody multimers (e.g., dimmers, trimers, tetramers, and polymers) are also encompassed by the low-molecular antibody of the present invention.

Such fragments of the antibody can be obtained by enzymatically treating the antibody to form antibody fragments. For example, papain, pepsin, or plasmin is known in the art as the enzyme for forming the antibody fragments. Alternatively, genes encoding these antibody fragments are constructed, and these genes can be introduced into expression vectors and then expressed in appropriate host cells (see e.g., Co, M. S. et al., J. Immunol. (1994) 152, 2968-2976; Better, M. & Horwitz, A. H. Methods in Enzymology (1989) 178, 476-496; Plueckthun, A. & Skerra, A. Methods in Enzymology (1989) 178, 476-496; Lamoyi, E., Methods in Enzymology (1989) 121, 652-663; Rousseaux, J. et al., Methods in Enzymology (1989) 121, 663-669; and Bird, R. E. et al., TIBTECH (1991) 9, 132-137).

The digestive enzymes cleave the antibody fragment at a particular position to give antibody fragments having a particular structure shown below. The use of a genetic engineering approach for the antibody fragments thus obtained enzymatically can delete an arbitrary portion of the antibody.
Papain digestion: F(ab)2 or Fab; and
Pepsin digestion: F(ab')2 or Fab'.

Thus, the low-molecular antibody according to the present invention can be an antibody fragment that lacks an arbitrary region as long as the antibody fragment has binding affinity for TM4SF20.

The Diabody refers to a bivalent antibody fragment constructed by gene fusion (e.g., Holliger P et al., Proc. Natl. Acad. Sci. USA 90: 6444-6448 (1993), EP404,097, and WO 93/11161). The Diabody is a dimer comprising two polypeptide chains. Usually, each of the polypeptide chains constituting the dimer comprises VL and VH linked via a linker on the same chain. The linker in the Diabody is generally too short to allow paring between VL and VH on the same chain. Specifically, the number of amino acid residues constituting the linker is, for example, approximately 5 residues. Therefore, VL and VH encoded on the same polypeptide chain cannot together form a single chain variable region fragment. Instead, they form a dimer by pairing with another single chain variable region fragment. As a result, the Diabody has two antigen-binding sites.

The scFv is obtained by linking H and L chain V regions of the antibody. In the scFv, the H and L chain V regions are linked via a linker, preferably, a peptide linker (Huston, J. S. et al., Proc. Natl. Acad. Sci. U.S.A., 1988, 85, 5879-5883). The H and L chain V regions in the scFv can be derived from any of the antibodies described in the present specification. The peptide linker that links the V regions is not particularly limited. For example, an arbitrary single chain peptide of approximately 3 to 25 residues can be used as the linker. Specifically, for example, a peptide linker described later can be used.

The V regions of both the chains can be linked, for example, by PCR as described above. First, of the following DNAs, DNAs encoding the whole or desired partial amino acid sequence are used as templates for linking the V regions by PCR:
DNA sequences encoding the H chain or H chain V region of the antibody, and
DNA sequences encoding the L chain or L chain V region of the antibody.

The H chain V region-encoding DNA and the L chain V region-encoding DNA are separately amplified by PCR using a pair of primers having sequences corresponding to both terminal sequences of each DNA to be amplified. Subsequently, DNA encoding the peptide linker portion is prepared. The DNA encoding the peptide linker can also be synthesized using PCR. Nucleotide sequences that can be linked to the amplification product of each V region gene separately synthesized are respectively added to the 5' sequences of primers used in this PCR. Subsequently, PCR reaction is performed using each DNA of [H chain V region DNA]-[peptide linker DNA]-[L chain V region DNA] and primers for assembly PCR.

The primers for assembly PCR comprises the combination of a primer annealed to the 5' sequence of the [H chain V region DNA] and a primer annealed to the 3' sequence of the [L chain V region DNA]. Specifically, the primers for assembly PCR are a primer set that is capable of amplifying DNA encoding the full-length sequence of the scFv to be synthesized. On the other hand, the [peptide linker DNA] contains the added nucleotide sequences that can be linked to each V region DNA. As a result, these DNAs are linked and, further, finally prepared into a full-length scFv gene amplification product using the primers for assembly PCR. Once the scFv-encoding DNA is prepared, expression vectors containing this DNA and cells transformed with the expression vectors (recombinant cells) can be obtained according to a routine method. Moreover, the resultant recombinant cells can be cultured for the expression of the scFv-encoding DNA to obtain the scFv.

The scFv-Fc is a low-molecular antibody comprising an Fc region fused to scFv (Cellular & Molecular Immunology 2006; 3: 439-443). The origin of the scFv used in the scFv-Fc is not particularly limited, and, for example, scFv derived from IgM can be used. Moreover, the origin of the Fc is not particularly limited, and, for example, Fc derived from human IgG (human IgG1, etc.) can be used. Thus, examples of a preferable aspect of the scFv-Fc can include scFv-Fc comprising an IgM antibody scFv fragment linked to human IgG1 CH2 (e.g., Cγ2) and CH3 (e.g., Cγ3) via the hinge region (Hγ) of human IgG1.

The sc(Fv)2 is a low-molecular antibody having a single chain comprising two VHs and two VLs linked via linkers or the like (Hudson et al., J. Immunol. Methods 1999; 231: 177-189). The sc(Fv)2 can be prepared, for example, by linking scFvs via a linker.

Moreover, the sc(Fv)2 is preferably an antibody wherein two VHs and two VLs are aligned as VH, VL, VH, and VL (i.e., [VH]-linker-[VL]-linker-[VH]-linker-[VL]) in this order starting at the N-terminus of the single chain polypeptide.

The order of two VHs and two VLs is not particularly limited to the arrangement described above and may be any order of arrangement. Examples thereof can also include the following arrangements:

[VL]-linker-[VH]-linker-[VH]-linker-[VL],
[VH]-linker-[VL]-linker-[VL]-linker-[VH],
[VH]-linker-[VL]-linker-[VH]-linker-[VL],
[VL]-linker-[VL]-linker-[VH]-linker-[VH], and
[VL]-linker-[VH]-linker-[VL]-linker-[VH].

For example, an arbitrary peptide linker or synthetic compound linker (e.g., linkers disclosed in the reference Protein Engineering, 9 (3), 299-305, 1996) that can be introduced by genetic engineering can be used as the linker that links the antibody variable regions. In the present invention, the peptide linker is preferable. The length of the peptide linker is not particularly limited and can be selected appropriately by those skilled in the art according to the purpose. The number of amino acid residues constituting the peptide linker is usually 1 to 100 amino acids, preferably 3 to 50 amino acids, more preferably 5 to 30 amino acids, particularly preferably 12 to 18 amino acids (e.g., 15 amino acids).

The amino acid sequence constituting the peptide linker can be an arbitrary sequence as long as this sequence does not inhibit the binding effect of the scFv. For example, the following amino acid sequences can be used for the peptide linker:

```
Ser,

Gly-Ser,

Gly-Gly-Ser,

Ser-Gly-Gly,

Gly-Gly-Gly-Ser,            (SEQ ID NO: 117)

Ser-Gly-Gly-Gly,            (SEQ ID NO: 118)

Gly-Gly-Gly-Gly-Ser,        (SEQ ID NO: 119)

Ser-Gly-Gly-Gly-Gly,        (SEQ ID NO: 120)

Gly-Gly-Gly-Gly-Gly-Ser,    (SEQ ID NO: 121)

Ser-Gly-Gly-Gly-Gly-Gly,    (SEQ ID NO: 122)

Gly-Gly-Gly-Gly-Gly-Gly-Ser (SEQ ID NO: 123)

Ser-Gly-Gly-Gly-Gly-Gly-Gly,(SEQ ID NO: 124)

(Gly-Gly-Gly-Gly-Ser)n,     (SEQ ID NO: 119)
and (Ser-Gly-Gly-Gly-Gly)n.     (SEQ ID NO: 120)

[n is an integer of 1 or more]
```

The amino acid sequence of the peptide linker can be selected appropriately by those skilled in the art according to the purpose. For example, the integer n that determines the length of the peptide linker is usually 1 to 5, preferably 1 to 3, more preferably 1 or 2.

Accordingly, examples of a particularly preferable aspect of the sc(Fv)2 according to the present invention can include the following sc(Fv)2:
[VH]-peptide linker (15 amino acids)-[VL]-peptide linker (15 amino acids)-[VH]-peptide linker (15 amino acids)-[VL].

Alternatively, the V regions can also be linked using the chemically synthesized linker (chemical cross-linking agent). Cross-linking agents usually used in the cross-link of peptide compounds or the like can be used in the present invention. For example, chemical cross-linking agents as shown below are known in the art. These cross-linking agents are commercially available.
N-hydroxysuccinimide (NHS),
disuccinimidyl suberate (DSS),
bis(sulfosuccinimidyl)suberate (BS3),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST),
disulfosuccinimidyl tartrate (sulfo-DST),
bis[2-(succinimidoxycarbonyloxy)ethyl]sulfone (BSOCOES), and
bis[2-(sulfosuccinimidoxycarbonyloxy)ethyl]sulfone (sulfo-BSOCOES), etc.

The linking of the 4 antibody variable regions usually requires 3 linkers. These plural linkers may be the same. Alternatively, different linkers may be used. In the present invention, the low-molecular antibody is preferably Diabody or sc(Fv)2. For obtaining such a low-molecular antibody, the antibody may be treated with an enzyme, for example, papain or pepsin to form antibody fragments. Alternatively, DNAs encoding these antibody fragments are constructed, and these DNAs may be introduced into expression vectors and then expressed in appropriate host cells (see e.g., Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; and Bird, R. E. and Walker, B. W., Trends Biotechnol. (1991) 9, 132-137).

3. Activity of Anti-TM4SF20 Antibody

For the treatment of cell-proliferative disease such as cancer, it is preferred that the antibody should maintain its effector activity. Specifically, the preferable antibody according to the present invention has both of binding affinity for TM4SF20 and effector functions. The effector functions of the antibody encompass ADCC activity and CDC activity. The therapeutic antibody according to the present invention particularly preferably possesses one or both of ADCC activity and CDC activity as effector functions.

3.1 Cytotoxic Activity

When the antibody of the present invention is used for the therapeutic purpose, the antibody is preferably an antibody having cytotoxic activity.

Examples of the cytotoxic activity according to the present invention can include antibody-dependent cell-mediated cytotoxicity (ADCC) activity and complement-dependent cytotoxicity (CDC) activity. In the present invention, the CDC activity means cytotoxic activity mediated by the complement system. On the other hand, the ADCC activity means the activity of damaging target cells through the binding of Fcγ receptor-bearing cells (immunocytes, etc.) via the Fcγ receptors to the Fc domains of antibodies specifically attached to the cell surface antigens of the target cells.

Whether or not the anti-TM4SF20 antibody has ADCC activity or has CDC activity can be determined by a method known in the art (e.g., Current protocols in Immunology, Chapter 7. Immunologic studies in humans, Editor, John E, Coligan et al., John Wiley & Sons, Inc., (1993)).

Specifically, effector cells, a complement solution, and target cells are first prepared.

i) Preparation of Effector Cells

The spleens are excised from CBA/N mice or the like, and spleen cells are separated therefrom in an RPMI1640 medium (manufactured by Invitrogen Corp.). The cells can be washed with the same medium containing 10% fetal bovine serum (FBS, manufactured by HyClone Laboratories, Inc.) and then adjusted to a cell concentration of $5 \times 10^6$ cells/ml to prepare effector cells.

ii) Preparation of Complement Solution

Baby Rabbit Complement (manufactured by CEDARLANE Laboratories Ltd.) can be diluted 10-fold with a medium (manufactured by Invitrogen Corp.) containing 10% FBS to prepare a complement solution.

iii) Preparation of Target Cells

Cells expressing TM4SF20 proteins can be cultured at 37° C. for 1 hour, together with 0.2 mCi $^{51}$Cr-sodium chromate (manufactured by GE Healthcare Bio-Sciences Corp.), in a DMEM medium containing 10% FBS to radiolabel the target cells. Cells transformed with TM4SF20 protein-encoding genes, stomach cancer cells, lung adenocarcinoma cells, pancreatic cancer cells, colon cancer cells, or the like can be used as the cells expressing TM4SF20 proteins. After the radiolabeling, the cells can be washed three times with an RPMI1640 medium containing 10% FBS and adjusted to a cell concentration of $2 \times 10^5$ cells/ml to prepare the target cells.

The ADCC or CDC activity can be assayed by a method described below. For the ADCC activity assay, the target cells and the anti-TM4SF20 antibody (50 µl each) are added to a U-bottom 96-well plate (manufactured by Becton, Dickinson and Company) and reacted for 15 minutes on ice. Then, 100 µl of the effector cells is added to the plate, and the cells are cultured for 4 hours in a $CO_2$ incubator. The final concentration of the antibody is set to 0 or 10 µg/ml. After the culture, 100 µl of the supernatant is collected, and the radioactivity is measured using a gamma counter (COBRA II AUTOGAMMA, MODEL D5005, manufactured by Packard Instrument Company). The cytotoxic activity (%) can be calculated based on the calculation formula $(A-C)/(B-C) \times 100$ using the obtained value. In the formula, A represents radioactivity (cpm) from each sample; B represents radioactivity (cpm) from a sample supplemented with 1% NP-40 (manufactured by Nacalai Tesque, Inc.); and C represents radioactivity (cpm) from a sample containing only the target cells.

On the other hand, for the CDC activity assay, the target cells and the anti-TM4SF20 antibody (50 µl each) are added to a flat-bottomed 96-well plate (manufactured by Becton, Dickinson and Company) and reacted for 15 minutes on ice. Then, 100 µl of the complement solution is added to the plate, and the cells are cultured for 4 hours in a $CO_2$ incubator. The final concentration of the antibody is set to 0 or 3 µg/ml. After the culture, 100 µl of the supernatant is collected, and the radioactivity is measured using a gamma counter. The cytotoxic activity can be calculated in the same way as in the ADCC activity assay.

On the other hand, in the assay of cytotoxic activity using antibody conjugates, the target cells and the anti-TM4SF20 antibody conjugates (50 µl each) are added to a flat-bottomed 96-well plate (manufactured by Becton, Dickinson and Company) and reacted for 15 minutes on ice. The cells are cultured for 1 to 4 hours in a $CO_2$ incubator. The final concentration of the antibody is set to 0 or 3 µg/ml. After the culture, 100 µl of the supernatant is collected, and the radioactivity is measured using a gamma counter. The cytotoxic activity can be calculated in the same way as in the ADCC activity assay.

(1) Modification with Cytotoxic Substance

The antibody may be conjugated to a cytotoxic substance such as a chemotherapeutic agent, a toxic peptide, or a radioactive chemical. Such a modified antibody (hereinafter, referred to as an antibody conjugate) can be obtained by chemically modifying the obtained antibody. A method for the antibody modification has already been established in the art.

Examples of the chemotherapeutic agent whose cytotoxic activity functions through the conjugation to the anti-TM4SF20 antibody can include the following chemotherapeutic agents: azaribine, anastrozole, azacytidine, bleomycin, bortezomib, bryostatin-1, busulfan, camptothecin, 10-hydroxycamptothecin, carmustine, Celebrex, chlorambucil, cisplatin, irinotecan, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin, ethinyl estradiol, estramustine, etoposide, etoposide glucuronide, floxuridine, fludarabine, flutamide, fluorouracil, fluoxymesterone, gemcitabine, hydroxyprogesterone caproate, hydroxyurea, idarubicin, ifosfamide, leucovorin, lomustine, mechlorethamine, medroxyprogesterone acetate, megestrol acetate, melphalan, mercaptopurine, methotrexate, mitoxantrone, mithramycin, mitomycin, mitotane, phenylbutyrate, prednisone, procarbazine, paclitaxel, pentostatin, semustine, streptozocin, tamoxifen, taxanes, taxol, testosterone propionate, thalidomide, thioguanine, thiotepa, teniposide, topotecan, uracil mustard, vinblastine, vinorelbine, and vincristine.

The chemotherapeutic agent is preferably a low-molecular chemotherapeutic agent. The low-molecular chemotherapeutic agent is less likely to interfere with the antibody functions even after its conjugation to the antibody. In the present invention, the low-molecular chemotherapeutic agent usually has a molecular weight of 100 to 2000, preferably 200 to 1000. All of the chemotherapeutic agents exemplified above are low-molecular chemotherapeutic agents. These chemotherapeutic agents according to the present invention encompass prodrugs that are converted in vivo to active chemotherapeutic agents. The prodrug activation may be enzymatic conversion or nonenzymatic conversion.

Moreover, the antibody can be modified with the toxic peptide. Examples of the toxic peptide can include the followings: diphtheria toxin A chain (Langone J. J., et al., Methods in Enzymology, 93, 307-308, 1983), *Pseudomonas* exotoxin (Nature Medicine, 2, 350-353, 1996), ricin A chain (Fulton R. J., et al., J. Biol. Chem., 261, 5314-5319, 1986; Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; and Gheeite V., et al., J. Immunol. Methods, 142, 223-230, 1991), deglycosylated ricin A chain (Thorpe P. E., et al., Cancer Res., 47, 5924-5931, 1987), abrin A chain (Wawrzynczak E. J., et al., Br. J. Cancer, 66, 361-366, 1992; Wawrzynczak E. J., et al., Cancer Res., 50, 7519-7562, 1990; Sivam G., et al., Cancer Res., 47, 3169-3173, 1987; and Thorpe P. E., et al., Cancer Res., 47, 5924-5931, 1987), gelonin (Sivam G., et al., Cancer Res., 47, 3169-3173, 1987; Cumber A. J. et al., J. Immunol. Methods, 135, 15-24, 1990; Wawrzynczak E. J., et al., Cancer Res., 50, 7519-7562, 1990; and Bolognesi A., et al., Clin. exp. Immunol., 89, 341-346, 1992), PAP-s (pokeweed anti-viral protein from seeds) (Bolognesi A., et al., Clin. exp. Immunol., 89, 341-346, 1992), bryodin (Bolognesi A., et al., Clin. exp. Immunol., 89, 341-346, 1992), saporin (Bolognesi A., et al., Clin. exp. Immunol., 89, 341-346, 1992), momordin (Cumber A. J., et al., J. Immunol. Methods, 135, 15-24, 1990; Wawrzynczak E. J., et al., Cancer Res., 50, 7519-7562, 1990; and Bolognesi A., et al., Clin. exp. Immunol., 89, 341-346, 1992), momorcochin (Bolognesi A., et al., Clin. exp. Immunol., 89, 341-346, 1992), dianthin 32 (Bolognesi A., et al., Clin. exp. Immunol., 89, 341-346, 1992), dianthin 30 (Stirpe F., Barbieri L., FEBS letter 195, 1-8, 1986), modeccin (Stirpe F., Barbieri L., FEES letter 195, 1-8, 1986), viscumin (Stirpe F., Barbieri L., FEBS letter 195, 1-8, 1986), volkensin (Stirpe F., Barbieri L., FEBS letter 195, 1-8, 1986), dodecandrin (Stirpe F., Barbieri L., FEBS letter 195, 1-8, 1986), tritin (Stirpe F., Barbieri L., FEBS letter 195, 1-8, 1986), luffin (Stirpe F., Barbieri L., FEBS letter 195, 1-8, 1986), and trichokirin (Casellas P., et al., Eur. J. Biochem. 176, 581-588, 1988; and Bolognesi A., et al., Clin. exp. Immunol., 89, 341-346, 1992).

In the present invention, the radioactive chemical refers to a chemical containing a radioisotope. Any radioisotope may be used without particular limitations as the radioisotope. For example, $^{32}P$, $^{14}C$, $^{125}I$, $^{3}H$, $^{131}I$, $^{186}Re$, or $^{188}Re$ can be used.

In another aspect, one or two or more low-molecular chemotherapeutic agents and one or two or more toxic peptides can be used in combination in the antibody modification. The anti-TM4SF20 antibody can be conjugated to the low-molecular chemotherapeutic agent via a covalent or noncovalent bond. A method for preparing such a chemotherapeutic agent-conjugated antibody is known in the art.

A proteinous agent or toxin can be conjugated to the antibody by a genetic engineering approach. Specifically, for example, DNA encoding the toxic peptide and DNA encoding the anti-TM4SF20 antibody are fused in frame with each other, and this fused DNA can be incorporated into expression vectors to construct recombinant vectors. The vectors are introduced into appropriate host cells, and the resultant transformed cells are cultured. The DNA insert can be expressed by the cells to obtain toxic peptide-conjugated anti-TM4SF20 antibodies as fusion proteins. For obtaining antibody-fusion proteins, the proteinous agent or toxin is generally located on the C-terminal side of the antibody. A peptide linker may be allowed to intervene between the antibody and the proteinous agent or toxin.

(2) Bispecific Antibody

Furthermore, the antibody of the present invention may be a bispecific antibody. The bispecific antibody refers to an antibody having, in the same antibody molecule, variable regions that recognize different epitopes. In the present invention, the bispecific antibody can have antigen-binding sites that recognize different epitopes on the TM4SF20 molecule. Thus, two such bispecific antibody molecules can bind to one TM4SF20 molecule. As a result, stronger cytotoxic effect can be expected.

Alternatively, the antibody of the present invention may be a bispecific antibody having antigen-binding sites, one of which recognizes TM4SF20 and the other of which recognizes a cytotoxic substance. The cytotoxic substance specifically encompasses, for example, a chemotherapeutic agent, a toxic peptide, and a radioactive chemical. Such a bispecific antibody binds to cells expressing TM4SF20, while it captures the cytotoxic substance. As a result, the cytotoxic substance can be allowed to directly act on the cells expressing TM4SF20. Specifically, the bispecific antibody that recognizes the cytotoxic substance can specifically damage tumor cells and inhibit the growth of the tumor cells.

Moreover, in the present invention, a bispecific antibody that recognizes an antigen other than TM4SF20 can be combined with the bispecific antibody described above. For example, the bispecific antibody that can be combined therewith recognizes an antigen that is specifically expressed on the surface of target cancer cells, as with TM4SF20, but is different from TM4SF20.

A method for producing the bispecific antibody is known in the art. For example, two antibodies differing in antigen recognized thereby can be bound to prepare the bispecific antibody. Each of the antibodies bound may be a ½ molecule having H and L chains or may be a ¼ molecule consisting of H chains. Alternatively, different monoclonal antibody-producing hybridomas can also be fused to prepare fusion cells producing bispecific antibodies. Furthermore, the bispecific antibody can be prepared by a genetic engineering approach.

The avidity of the antibody to antigens can be determined using means known in the art (Antibodies A Laboratory Manual. Ed Harlow, David Lane, Cold Spring Harbor Laboratory, 1988). For example, ELISA (enzyme-linked immunosorbent assay), EIA (enzyme immunoassay), RIA (radioimmunoassay), or fluoroimmunoassay can be used.

(3) Modification of Sugar Chain

The antibody of the present invention may be an antibody having a modified sugar chain. It is known that the cytotoxic activities of antibodies can be enhanced by modifying their sugar chains. For example, the following antibodies are known in the art as the antibody having a modified sugar chain:

glycosylated antibodies (WO 99/54342, etc.),
antibodies deficient in fucose added to their sugar chains (WO 00/61739, WO 02/31140, etc.), and
antibodies having a sugar chain having bisecting GlcNAc (WO 02/79255, etc.).

3.2 Internalization Activity

Moreover, the antibody of the present invention may have internalization activity. In the present invention, the "antibody having internalization activity" means an antibody that is transported into cells (cytoplasm, vesicles, other organelles, etc.) through its binding to TM4SF20.

Whether or not the antibody has internalization activity can be confirmed by a method generally known by those skilled in the art and can be confirmed by, for example, a method comprising contacting labeling substance-bound anti-TM4SF20 antibodies with TM4SF20-expressing cells and confirming whether or not the labeling substance is incorporated into the cells, or a method comprising contacting cytotoxic substance-conjugated anti-TM4SF20 antibodies with TM4SF20-expressing cells and confirming whether or not the death of the TM4SF20-expressing cells is induced.

The antibody having internalization activity can be conjugated to, for example, the cytotoxic substance and used as a pharmaceutical composition such as an anticancer agent described later.

4. Preparation of Anti-TM4SF20 Antibody 4.1 Preparation of Anti-TM4SF20 Antibody Using Monoclonal Antibody-Producing Hybridoma Monoclonal antibody-producing hybridomas can be prepared according to a technique known in the art as follows: first, animals are immunized with TM4SF20 proteins or partial peptides thereof (which will be described later) used as sensitizing antigens according to a usual immunization method. The obtained immunocytes are fused with parental cells known in the art by a usual cell fusion method to obtain hybridomas. From these hybridomas, cells producing the antibody of interest can further be screened by a usual screening method to select hybridomas producing the anti-TM4SF20 antibody. The desired anti-TM4SF20 monoclonal antibody is obtained from the selected hybridomas. Specifically, the anti-TM4SF20 monoclonal antibody is prepared as follows:

(1) Preparation of TM4SF20 Protein

First, TM4SF20 genes can be expressed to obtain TM4SF20 proteins used as sensitizing antigens for antibody obtainment. Specifically, the TM4SF20-encoding gene sequence is inserted into expression vectors known in the art, with which appropriate host cells are then transformed. Then, the human TM4SF20 proteins of interest are purified from the host cells or a culture supernatant thereof by a method known in the art. Purified natural TM4SF20 proteins or fusion proteins comprising the desired partial polypeptide of the TM4SF20 protein fused with a different polypeptide may be used as immunogens. For example, antibody Fc fragments, peptide tags, and so on can be used for producing the fusion proteins used as immunogens. Expression vectors for the fusion proteins can be prepared by fusing, in frame, two or more genes respectively encoding the desired polypeptide fragments and inserting this fusion gene into expression vectors. The method for preparing the fusion proteins is described in Molecular Cloning 2nd ed. (Sambrook, J. et al., Molecular Cloning 2nd ed., 9.47-9.58, Cold Spring Harbor Lab. Press, 1989).

The TM4SF20 proteins thus purified can be used as sensitizing antigens used for the immunization of mammals. Partial peptides of TM4SF20 can also be used as sensitizing antigens. For example, the following peptides can be used as sensitizing antigens:

peptides obtained by chemical synthesis based on the amino acid sequence of human TM4SF20;

peptides obtained by incorporating a portion of the TM4SF20 gene to expression vectors, followed by its expression; and peptides obtained by digesting the TM4SF20 protein with protease.

The region and size of the partial peptide of TM4SF20 used are not limited. The number of amino acids constituting the peptide serving as a sensitizing antigen is preferably at least 3 or more, for example, 5 or more or 6 or more. More specifically, peptides of 8 to 50, preferably 10 to 30 residues can be used as sensitizing antigens.

(2) Immunization with TM4SF20 Protein

Mammals are immunized with the TM4SF20 proteins or partial peptides thereof as sensitizing antigens. The immunized mammals are not particularly limited. For obtaining the monoclonal antibody by the cell fusion method, it is preferred that the immunized animals should be selected in consideration of compatibility with the parental cells used in cell fusion. In general, rodents are preferable as the immunized animals. Specifically, mice, rats, hamsters, or rabbits can be used as the immunized animals. In addition, monkeys or the like may be used as the immunized animals.

These animals can be immunized with the sensitizing antigens according to a method known in the art. For example, a general method can involve immunizing the mammals with the sensitizing antigens by intraperitoneal or subcutaneous injection. Specifically, the sensitizing antigens are administered to the mammals several times at 4- to 21-day intervals. The sensitizing antigens are diluted with PBS (phosphate-buffered saline), saline, or the like at an appropriate dilution ratio and used in the immunization. Furthermore, the sensitizing antigens may be administered together with an adjuvant. For example, the antigens can be mixed with a Freund's complete adjuvant for emulsification to prepare sensitizing antigens. Moreover, an appropriate carrier can be used in the immunization with the sensitizing antigens. Particularly, when partial peptides having a small molecular weight are used as the sensitizing antigens, it is preferred that the sensitizing antigen peptides should be bound to carrier proteins such as albumin or keyhole limpet hemocyanin and used in the immunization.

(3) DNA Immunization

The monoclonal antibody can also be obtained by DNA immunization. The DNA immunization is an immunostimulation method comprising: immunizing animals by the administration of vector DNA that has been constructed in a form capable of expressing antigenic protein-encoding genes in the immunized animals; and allowing the immunized animals to express the immunizing antigens in vivo. The DNA immunization can be expected to be superior to general immunization methods using the administration of protein antigens as follows:

it can provide immunostimulation with membrane protein (e.g., TM4SF20) structures maintained; and it eliminates the need of purifying immunizing antigens.

For obtaining the monoclonal antibody of the present invention by the DNA immunization, first, animals are immunized by the administration of TM4SF20 protein expression vector DNA. TM4SF20-encoding DNA can be synthesized by a method known in the art such as PCR. The obtained DNA is inserted into appropriate expression vectors, with which animals are immunized by administration. For example, commercially available expression vectors such as pcDNA3.1 can be used as the expression vectors. A method generally used can also be used as a method for administering the vectors to the animals. For example, gold particles with the expression vectors adsorbed onto can be inserted into cells using a gene gun to perform DNA immunization.

(4) Preparation of Hybridoma

Increase in the amount of the desired antibody in the serum of the mammals thus immunized is confirmed. Then, immunocytes are collected from the mammals and subjected to cell fusion. Particularly, spleen cells can be used as preferable immunocytes.

Mammalian myeloma cells are used as cells fused with the immunocytes. It is preferred that the myeloma cells should have an appropriate selection marker for screening. The selection marker refers to a character that can survive (or cannot survive) under particular culture conditions. For example, hypoxanthine-guanine phosphoribosyltransferase deficiency (hereinafter, abbreviated to HGPRT deficiency) or thymidine kinase deficiency (hereinafter, abbreviated to TK deficiency) is known in the art as the selection marker. Cells having the HGPRT or TK deficiency is sensitive to hypoxanthine-aminopterin-thymidine (hereinafter, abbreviated to HAT-sensitive). The HAT-sensitive cells are killed in a HAT selective medium because they cannot synthesize DNA. By contrast, these cells, when fused with normal cells, can grow even in the HAT selective medium because they can continue DNA synthesis by use of the salvage pathway of the normal cells.

The cells having the HGPRT or TK deficiency can be selected in a medium containing 6-thioguanine or 8-azaguanine (hereinafter, abbreviated to 8AG) for the HGPRT deficiency or 5'-bromodeoxyuridine for the TK deficiency. The normal cells are killed in such a medium because they incorporate these pyrimidine analogs into their DNAs. By contrast, the cells deficient in these enzymes can survive in the selective medium because they cannot incorporate the pyrimidine analogs therein. In addition, a selection marker called G418 resistance imparts, to cells, 2-deoxystreptamine antibiotic (gentamicin analog) resistance via a neomycin resistance gene. Various myeloma cells suitable for the cell fusion are known in the art. For example, the following myeloma cells can be used in the production of the monoclonal antibody according to the present invention:

P3 (P3x63Ag8.653) (J. Immunol. (1979) 123, 1548-1550),
P3x63Ag8U.1 (Current Topics in Microbiology and Immunology (1978) 81, 1-7),
NS-1 (Kohler. G. and Milstein, C. Eur. J. Immunol. (1976) 6, 511-519),
MPC-11 (Margulies. D. H. et al., Cell (1976) 8, 405-415),
SP2/0 (Shulman, M. et al., Nature (1978) 276, 269-270),
FO (de St. Groth, S. F. et al., J. Immunol. Methods (1980) 35, 1-21), S194 (Trowbridge, I. S. J. Exp. Med. (1978) 148, 313-323), and
R210 (Galfre, G. et al., Nature (1979) 277, 131-133).

Basically, the cell fusion of the immunocytes with the myeloma cells is performed according to a method known in the art, for example, the method of Kohler and Milstein et al. (Kohler. G. and Milstein, C., Methods Enzymol. (1981) 73, 3-46).

More specifically, the cell fusion can be performed, for example, in a usual nutrient culture medium in the presence of a cell fusion promoter. For example, polyethylene glycol (PEG) or hemagglutinating virus of Japan (HVJ) can be used as the fusion promoter. Furthermore, an auxiliary such as dimethyl sulfoxide can also be added thereto, if desired, for enhancing fusion efficiency.

The ratio between the immunocytes and the myeloma cells used can be set arbitrarily. For example, it is preferred that the amount of the immunocytes should be set to 1 to 10 times that of the myeloma cells. For example, RPMI1640 or MEM culture medium suitable for the growth of the myeloma cell line as well as usual culture media used in this kind of cell culture can be used as the culture medium used in the cell fusion. Furthermore, a solution supplemented with serum (e.g., fetal calf serum (FCS)) can be added to the culture medium.

For the cell fusion, the immunocytes and the myeloma cells are well mixed in the predetermined amounts in the culture medium, and these mixed cells are mixed with a PEG solution preheated to approximately 37° C. to form the fusion cells (hybridomas) of interest. In the cell fusion method, for example, PEG with an average molecular weight on the order of 1000 to 6000 can usually be added at a concentration of 30 to 60% (w/v). Subsequently, the appropriate culture medium exemplified above is sequentially added to the hybridomas, and the mixture is centrifuged, followed by removal of the supernatant. This procedure is repeated to remove the cell fusion agents or the like unfavorable for hybridoma growth.

The hybridomas thus obtained can be selected by use of a selective culture medium appropriate for the selection marker of the myeloma cells used in the cell fusion. For example, the cells having the HGPRT or TK deficiency can be selected by culturing the hybridomas in a HAT culture medium (culture medium containing hypoxanthine, aminopterin, and thymidine). Specifically, when HAT-sensitive myeloma cells are used in the cell fusion, only cells successfully fused with normal cells can be grown selectively in the HAT culture medium. The culture using the HAT culture medium is continued for a time long enough to kill cells (non-fused cells) other than the hybridomas of interest. Specifically, the culture can generally be performed for a few days to a few weeks to select the hybridomas of interest. Subsequently, hybridomas producing the antibody of interest can be screened and cloned as single clones by a usual limiting dilution method.

The screening of the antibody of interest and cloning as single clones thereof can be performed preferably by a screening method based on antigen-antibody reaction known in the art. For example, the antigens are bound to a carrier such as beads made of polystyrene or the like or a commercially available 96-well microtiter plate and reacted with the culture supernatant of the hybridomas. Subsequently, the carrier is washed and then reacted with enzyme-labeled secondary antibodies or the like. If the culture supernatant contains the antibody of interest reactive with the sensitizing antigens, the secondary antibodies bind to the carrier via this antibody. Finally, the secondary antibodies bound with the carrier can be detected to determine the presence of the antibody of interest in the culture supernatant. The hybridomas producing the desired antibody capable of binding to the antigen can be cloned by a limiting dilution method or the like. In this screening, the TM4SF20 proteins used in the immunization or TM4SF20 proteins substantially identical thereto can be used preferably as the antigens. For example, cell lines expressing TM4SF20, soluble TM4SF20, or the like can be used as the antigens.

A method described in International Publication No. WO 03/104453 may be used in the production of the antibody against human TM4SF20.

Moreover, in addition to the method for obtaining the hybridomas by immunizing non-human animals with the antigens, human lymphocytes may be sensitized with the antigens to obtain the antibody of interest.

Specifically, the human lymphocytes are first sensitized with the TM4SF20 proteins in vitro. Subsequently, the sensitized lymphocytes are fused with appropriate fusion partners. For example, human-derived myeloma cells capable of dividing throughout their lives can be used as the fusion partners (see Japanese Patent Publication No. 1-59878).

Furthermore, the anti-TM4SF20 human antibody can also be obtained by administering the TM4SF20 proteins as antigens to transgenic animals having all repertoires of human antibody genes or by immunizing the animals with DNA that has been constructed to express TM4SF20 in the animals. Antibody-producing cells from the immunized animals can be immortalized by treatment such as cell fusion with appropriate fusion partners or infection with Epstein-Barr virus. From the immortalized cells thus obtained, human antibodies against the TM4SF20 protein can be isolated (see International Publication Nos. WO 94/25585, WO 93/12227, WO 92/03918, and WO 94/02602). Furthermore, the immortalized cells can also be cloned as cells producing antibodies having the reaction specificity of interest. When transgenic animals are used as the immunized animals, the immune systems of the animals recognize human TM4SF20 as foreigners. Thus, the human antibodies against human TM4SF20 can be obtained easily.

(5) Obtainment of Monoclonal Antibody from Hybridoma

The monoclonal antibody-producing hybridomas thus prepared can be subcultured in a usual culture medium. Moreover, the hybridomas can also be stored over a long period in liquid nitrogen.

The hybridomas are cultured according to a usual method, and the monoclonal antibody of interest can be obtained from the culture supernatant thereof. Alternatively, the hybridomas are administered to mammals compatible therewith and grown, and the monoclonal antibody can also be obtained in the form of ascitic fluids. The former method is suitable for obtaining highly pure antibodies.

4.2 Preparation of Anti-TM4SF20 Antibody by Genetic Engineering Approach (1) Cloning of Antibody Gene The antibody may be prepared by a genetic engineering approach using antibody genes cloned from antibody-producing cells. The cloned antibody genes can be incorporated into appropriate vectors and expressed as antibodies by the transformation of hosts. Methods for the antibody gene isolation, the introduction into vectors, and the transformation of host cells have already been established (see e.g., Vandamme, A. M. et al., Eur. J. Biochem. (1990) 192, 767-775).

For example, cDNAs encoding the variable regions (V regions) of the anti-TM4SF20 antibody can be obtained from the anti-TM4SF20 antibody-producing hybridoma cells. For this purpose, usually, total RNAs are first extracted from the hybridomas. For example, the following methods can be used as a method for mRNA extraction from the cells:

guanidine ultracentrifugation method (Chirgwin, J. M. et al., Biochemistry (1979) 18, 5294-5299), and
AGPC method (Chomczynski, P. et al., Anal. Biochem. (1987) 162, 156-159).

The extracted mRNAs can be purified using mRNA Purification Kit (manufactured by GE Healthcare Bio-Sciences Corp.) or the like. Alternatively, a kit for directly extracting total mRNAs from cells is also commercially available, such as QuickPrep mRNA Purification Kit (manufactured by GE Healthcare Bio-Sciences Corp.). The total mRNAs may be obtained from the hybridomas using such a kit. From the obtained mRNAs, antibody V region-encoding cDNAs can be synthesized using reverse transcriptase. In this procedure, arbitrary 15- to 30-base sequences selected from sequences common to the antibody gene can be used as primers. The cDNAs can be synthesized using AMV Reverse Transcriptase First-strand cDNA Synthesis Kit (manufactured by SEIKAGAKU CORP.) or the like. Moreover, 5'-Ampli FINDER RACE Kit (manufactured by Clontech Laboratories, Inc.) and 5'-RACE PCR (Frohman, M. A. et al., Proc. Natl. Acad. Sci. USA (1988) 85, 8998-9002; and Belyaysky, A. et al., Nucleic Acids Res. (1989) 17, 2919-2932) can be used for the cDNA synthesis and amplification. Furthermore, appropriate restriction sites described later can be introduced into both ends of the cDNAs in the course of such cDNA synthesis.

From the obtained PCR products, the cDNA fragments of interest are purified and subsequently ligated with vector DNAs. The recombinant vectors thus prepared are introduced into *E. coli* or the like. After colony selection, the desired recombinant vectors can be prepared from *E. coli* that has formed the colony. Then, the nucleotide sequence of the cDNA can be confirmed by a method known in the art, for example, a dideoxynucleotide chain termination method.

Moreover, cDNA libraries may be used for obtaining the antibody variable region-encoding genes. First, cDNAs are synthesized with mRNAs extracted from the antibody-producing cells as templates to obtain cDNA libraries. A commercially available kit is conveniently used in the cDNA library synthesis. In actuality, mRNAs from only a small number of cells are obtained in very small amounts. Therefore, direct purification thereof results in low yields. Thus, carrier RNAs shown to be free from the antibody genes are usually added thereto, followed by purification. Alternatively, when RNAs can be extracted in given amounts, efficient extraction can be achieved only using those from the antibody-producing cells. The addition of the carrier RNAs may be unnecessary for RNA extraction from, for example, 10 or more or 30 or more, preferably 50 or more antibody-producing cells.

The antibody genes are amplified by PCR with the obtained cDNA libraries as templates. Primers for the PCR amplification of the antibody genes are known in the art. For example, primers for human antibody gene amplification can be designed based on the disclosure of the paper (J. Mol. Biol. (1991) 222, 581-597) or the like. These primers have a nucleotide sequence differing on an immunoglobulin subclass basis. Thus, when cDNA libraries whose subclass is unknown are used as templates, PCR is performed in consideration of every possibility.

Specifically, for example, for the purpose of obtaining human IgG-encoding genes, primers can be used, which are capable of respectively amplifying genes encoding γ1 to γ5 heavy chains and κ and λ light chains. For amplifying IgG variable region genes, 3' primers are generally used, which anneal to a portion corresponding to the hinge region. On the other hand, primers appropriate for each subclass can be used as 5' primers.

The PCR products obtained from the primers for gene amplification for these heavy and light chain subclasses are prepared as their respective independent libraries. The libraries thus synthesized can be used to reshape immunoglobulins comprising the heavy and light chains in combination. The antibody of interest can be screened with the avidity of the reshaped immunoglobulins for TM4SF20 as an index.

(2) Introduction of Antibody Gene into Host Cell

For producing the anti-TM4SF20 antibody, the cloned antibody genes can be incorporated into expression vectors such that these genes are expressed under the control of expression control regions. The expression control regions for antibody expression encompass, for example, enhancers and promoters. Subsequently, appropriate host cells can be transformed with these expression vectors to obtain recombinant cells expressing the anti-TM4SF20 antibody-encoding DNA.

For the antibody gene expression, the antibody heavy chain (H chain)- and light chain (L chain)-encoding DNAs can be incorporated separately in different expression vectors. The same host cell can be co-transfected with the H chain- and L chain-incorporated vectors and thereby allowed to express antibody molecules comprising the H and L chains. Alternatively, the H chain- and L chain-encoding DNAs may be incorporated in single expression vectors, with which host cells are transformed (see International Publication No. WO 94/11523).

The hosts and the expression vectors for introducing the isolated antibody genes into appropriate hosts for antibody preparation are known in the art as many combinations. All of these expression systems can be applied to the present invention. When eukaryotic cells are used as the hosts, animal, plant, or fungus cells can be used. Specifically, examples of the animal cells that can be used in the present invention can include the following cells:

i) mammalian cells: CHO, COS, myeloma, BHK (baby hamster kidney), Hela, Vero, HEK293, Ba/F3, HL-60, Jurkat, and SK-HEP1 cells;
ii) amphibian cells: *Xenopus* oocytes; and
iii) insect cells: sf9, sf21, and Tn5 cells.

For the plant cells, antibody gene expression systems are known in the art, which involve cells derived from the genus *Nicotiana* (e.g., *Nicotiana tabacum*). Cultured callus cells can be used in the plant cell transformation.

Furthermore, the following cells can be used as the fungus cells:
cells derived from: yeasts such as the genus *Saccharomyces* (e.g., *Saccharomyces cerevisiae*) and filamentous fungi of the genus *Pichia* (e.g., *Pichia pastoris*); and the genus *Aspergillus* (e.g., *Aspergillus niger*).

Alternatively, antibody gene expression systems using prokaryotic cells are also known in the art. For example, when bacterial cells are used, bacterial cells derived from *E. coli, Bacillus subtilis*, or the like can be used in the present invention.

When the mammalian cells are used, a useful promoter routinely used, the antibody gene to be expressed, and a poly A signal located 3'-downstream thereof can be ligated functionally for the gene expression. Examples of the promoter/enhancer can include a human cytomegalovirus immediate early promoter/enhancer.

Moreover, in addition, virus promoters/enhancers and mammalian cell-derived promoters/enhancers (e.g., human elongation factor 1α (HEF1α)) can be used in the antibody expression. Examples of the viruses whose promoter/enhancer can be used can specifically include retrovirus, polyomavirus, adenovirus, and simian virus 40 (SV40).

The SV40 promoter/enhancer can be used according to the method of Mulligan et al. (Nature (1979) 277, 108). Moreover, the HEF1α promoter/enhancer can be used easily in the gene expression of interest by the method of Mizushima et al. (Nucleic Acids Res. (1990) 18, 5322).

For the *E. coli*, a useful promoter routinely used, a signal sequence for antibody secretion, and the antibody gene to be expressed can be ligated functionally for the gene expression. Examples of the promoter can include lacZ and araB promoters. The lacZ promoter can be used according to the method of Ward et al. (Nature (1989) 341, 544-546; and FASEBJ. (1992) 6, 2422-2427). Alternatively, the araB promoter can be used in the gene expression of interest by the method of Better et al. (Science (1988) 240, 1041-1043).

When antibodies are produced in *E. coli* periplasm, a pelB signal sequence (Lei, S. P. et al., J. Bacteriol. (1987) 169, 4379) may be used as the signal sequence for antibody secretion. Then, the antibodies produced in the periplasm are separated and then refolded by use of protein denaturants such as urea and guanidine hydrochloride such that the resultant antibodies have the desired avidity.

When antibodies are produced using animal cells, the signal sequence of the heavy chain or light chain gene of the antibody is preferably used as a signal sequence required for extracellular secretion. Moreover, the signal sequence of a secretory protein such as IL-3 or IL-6 may be used.

A replication origin derived from SV40, polyomavirus, adenovirus, bovine papillomavirus (BPV), or the like can be used as a replication origin inserted in the expression vectors. Furthermore, a selection marker can be inserted in the expression vectors for increasing a gene copy number in the host cell systems. Specifically, the following selection markers can be used:

aminoglycoside phosphotransferase (APH) gene,
thymidine kinase (TK) gene,
*E. coli* xanthine-guanine phosphoribosyltransferase (Ecogpt) gene, and
dihydrofolate reductase (dhfr) gene, etc.

(3) Obtainment of Antibody from Host Cell

The host cells are transformed with these expression vectors, and the transformed host cells are then cultured in vitro or in vivo to produce the antibody of interest. The culture of the host cells is performed according to a method known in the art. For example, a DMEM, MEM, RPMI1640, or IMDM culture medium can be used and may be used in combination with a solution supplemented with serum such as fetal calf serum (FCS).

The antibodies thus expressed and produced can be purified by using, alone or in appropriate combination, usual protein purification methods known in the art. For example, affinity or chromatography columns (e.g., protein A columns), filters, ultrafiltration, salting-out, and dialysis can be selected and combined appropriately to separate and purify the antibodies (Antibodies A Laboratory Manual. Ed Harlow, David Lane, Cold Spring Harbor Laboratory, 1988).

4.3 Antibody Production by Transgenic Animal

In addition to the host cells, transgenic animals can also be used in the recombinant antibody production. Specifically, the antibody of interest can be obtained from animals transfected with the genes encoding this antibody of interest. For example, the antibody genes can be inserted in frame into genes encoding proteins specifically produced in milk to construct fusion genes. For example, goat β casein can be used as the proteins secreted into milk. DNA fragments containing the fusion genes having the antibody gene insert are injected into goat embryos, which are in turn introduced into female goats. From milk produced by transgenic goats (or progeny thereof) brought forth by the goats that have received the embryos, the desired antibody can be obtained as a fusion protein with the milk protein. Moreover, in the transgenic goats, hormone can be used appropriately for increasing the amount of milk containing the desired antibody produced from the transgenic goats (Ebert, K. M. et al., Bio/Technology (1994) 12, 699-702).

5. Pharmaceutical Composition

TM4SF20 is highly expressed in a specific manner in tissues of cancer such as stomach cancer, lung adenocarcinoma, pancreatic cancer, or colon cancer. The anti-TM4SF20 antibody has cancer cell-specific cytotoxic effect. Thus, the anti-TM4SF20 antibody is useful in the treatment of these cancers expressing TM4SF20.

Specifically, the present invention provides a pharmaceutical composition comprising the antibody binding to a TM4SF20 protein as an active ingredient. In an embodiment, the pharmaceutical composition is a cell growth inhibitor, particularly, an anticancer agent. It is preferred that the cell growth inhibitor and the anticancer agent of the present invention should be administered to a subject having cancer or possibly having cancer.

The anti-TM4SF20 antibody used in the pharmaceutical composition (e.g., anticancer agent) of the present invention is not particularly limited, and, for example, any of the anti-TM4SF20 antibodies described above can be used.

In the present invention, the phrase "comprising the antibody binding to TM4SF20 as an active ingredient" means comprising the anti-TM4SF20 antibody as a main active ingredient and does not limit the content of the anti-TM4SF20 antibody.

The pharmaceutical composition of the present invention may comprise the cytotoxic substance-conjugated anti-TM4SF20 antibody, as described in the paragraph 3.1 (1), as an active ingredient. This pharmaceutical composition can be used as a cell growth inhibitor, particularly, an anticancer agent. It is preferred that the cell growth inhibitor and the anticancer agent of the present invention should be administered to a subject having cancer or possibly having cancer.

In the present invention, the phrase "comprising the cytotoxic substance-conjugated anti-TM4SF20 antibody as an active ingredient" means comprising the cytotoxic substance-conjugated anti-TM4SF20 antibody as a main active ingredient and does not limit the content of the cytotoxic substance-conjugated anti-TM4SF20 antibody.

When the disease targeted by the pharmaceutical composition of the present invention is cancer, the targeted cancer is not particularly limited and is preferably stomach cancer, lung adenocarcinoma, pancreatic cancer, or colon cancer. The cancer may be any of primary foci and metastatic foci.

The pharmaceutical composition of the present invention can be administered either orally or parenterally to a patient. Parenteral administration is preferable. Specific examples of such an administration method include injection, transnasal, pulmonary, and transdermal administrations. Examples of the injection administration include intravenous, intramuscular, intraperitoneal, and subcutaneous injections, through which the pharmaceutical composition of the present invention can be administered systemically or locally. Moreover, the administration method can be selected appropriately according to the age or symptoms of the patient. The dose of the pharmaceutical composition of the present invention can be selected from among a dose range of, for example, 0.0001 mg to 1000 mg per kg body weight per dosing. Alternatively, the dose can be selected from among a range of, for example, 0.001 to 100000 mg/body per patient. However, the pharmaceutical composition of the present invention is not limited to these doses.

The pharmaceutical composition of the present invention can be formulated according to a standard method (e.g., Remington's Pharmaceutical Science, latest edition, Mark Publishing Company, Easton, U.S.A.) and may additionally contain pharmaceutically acceptable carriers or additives. Examples thereof include, but not limited thereto, surfactants, excipients, coloring agents, flavoring agents, preservatives, stabilizers, buffers, suspending agents, tonicity agents, binders, disintegrants, lubricants, flow promoters, and corrigents. Other carriers routinely used can be used appropriately. Specific examples of the carriers can include light anhydrous silicic acid, lactose, crystalline cellulose, mannitol, starch, carmellose calcium, carmellose sodium, hydroxypropylcellulose, hydroxypropylmethylcellulose, polyvinyl acetal diethylaminoacetate, polyvinyl pyrrolidone, gelatin, middle chain fatty acid triglyceride, polyoxyethylene hydrogenated castor oil 60, white sugar, carboxymethylcellulose, corn starch, and inorganic salts.

The anti-TM4SF20 antibody of the present invention can cause damage to TM4SF20-expressing cells or inhibition of their growth by contact with the TM4SF20-expressing cells. Such a method using the anti-TM4SF20 antibody is also incorporated in the scope of the present invention. The antibody used is not particularly limited, and, for example, any of the antibodies described above can be used. The cells to which the anti-TM4SF20 antibody binds are not particularly limited as long as the cells express TM4SF20. In the present invention, the TM4SF20-expressing cells are preferably cancer cells, more preferably stomach cancer cells, lung adenocarcinoma cells, pancreatic cancer cells, or colon cancer cells. The method can also be applied to any of the primary foci and metastatic foci of these cancers.

In the present invention, the "contact" is performed, for example, by adding the antibody to a culture medium of TM4SF20-expressing cells cultured in a test tube. Moreover, in the present invention, the "contact" is also performed by administering the anti-TM4SF20 antibody to non-human animals implanted with TM4SF20-expressing cells in their bodies or to animals endogenously having cancer cells expressing TM4SF20.

Methods shown below are preferably used as methods for evaluating or determining cytotoxicity caused in the TM4SF20-expressing cells by the contact of the anti-TM4SF20 antibody. Examples of methods for evaluating or determining the cytotoxic activity in vitro can include assay for antibody-dependent cell-mediated cytotoxicity (ADCC) activity or complement-dependent cytotoxicity (CDC) activity. Whether or not the anti-TM4SF20 antibody has ADCC activity or has CDC activity can be determined by a method known in the art (e.g., Current protocols in Immunology, Chapter 7. Immunologic studies in humans, Editor, John E, Coligan et al., John Wiley & Sons, Inc., (1993)). In the activity assay, conjugated antibodies that have an isotype identical to that of the anti-TM4SF20 antibody and are free from the cytotoxic activity are used as control antibodies in the same way as in the anti-TM4SF20 antibody. When the anti-TM4SF20 antibody exhibits stronger cytotoxic activity than that of the control antibodies, the anti-TM4SF20 antibody can be determined to have the activity.

The isotype of an antibody is specified based on the sequence of the H chain constant region in the amino acid sequence of this antibody. The antibody isotype is finally determined depending on class switching caused by genetic recombination on the chromosome during the maturation of antibody-producing B cells in vivo. Difference in isotype reflects difference between the physiological/pathological functions of antibodies. Specifically, for example, it is known that the strength of cytotoxic activity is influenced not only by antigen expression levels but by antibody isotypes. Thus, for the cytotoxic activity assay, it is preferred that the antibodies used as controls should have an isotype identical to that of the antibody to be tested.

Moreover, for evaluating or determining the cytotoxic activity in vivo, for example, TM4SF20-expressing cancer cells are intradermally or subcutaneously transplanted to non-human test animals. Then, the antibody to be tested is intravenously or intraperitoneally administered thereto on a daily basis or at a few day-intervals from the administration day or the next day. The cytotoxic activity can be determined by measuring tumor sizes over time. Control antibodies having an isotype identical thereto are administered in the same way in the in vitro evaluation. When the anti-TM4SF20 antibody-administered group has a significantly smaller tumor size than that of the control antibody-administered group, the anti-TM4SF20 antibody can be determined to have the cytotoxic activity. When mice were used as the non-human test animals, nude (nu/nu) mice can be used preferably, which are genetically deficient in thymus gland and thus lack the functions of T lymphocytes. The use of the mice can exclude the involvement of the T lymphocytes in the test animals in the evaluation/determination of cytotoxic activity of administered antibodies.

6. Diagnostic Drug (Diagnosis Method)

The present invention also provides a method for diagnosing cancer, comprising detecting a TM4SF20 protein or a TM4SF20 protein-encoding gene. TM4SF20 has been confirmed to have remarkably increased expression in various cancer tissues or cancer cell lines. Thus, TM4SF20 is useful as a marker for specifically detecting cancer.

6.1 Detection of TM4SF20 Protein

In one aspect of the method of the present invention, cancer is diagnosed by detecting a TM4SF20 protein in a sample. It is preferred that the TM4SF20 protein detection should be performed using an antibody that recognizes the TM4SF20 protein.

One specific example of the diagnosis method of the present invention can include a method for diagnosing cancer, comprising the following steps:
(a) preparing a sample isolated from a test subject; and
(b) detecting the expression level of a TM4SF20 protein or a TM4SF20 gene in the sample.

Moreover, the diagnosis method of the present invention may further comprise, in addition to the steps (a) and (b), the step (c) of evaluating the possibility that the test subject has cancer, based on the expression level of the TM4SF20 protein or the TM4SF20 gene.

In the present invention, the detection encompasses quantitative or qualitative detection. Examples of the qualitative detection can include the following assays: simple assay on the presence or absence of the TM4SF20 protein, assay on the presence or absence of more than a predetermined amount of the TM4SF20 protein, and assay comprising comparing the amount of the TM4SF20 protein with that contained in another sample (e.g., a control sample).

On the other hand, examples of the quantitative detection can include measurement of a TM4SF20 protein concentration and measurement of the amount of the TM4SF20 protein.

The test sample according to the present invention is not particularly limited as long as the sample is likely to contain the TM4SF20 protein. Specifically, samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a preparation on which tissues or cells collected from living body is fixed, or a sample obtained from the test sample, such as a cell culture medium.

The cancer diagnosed by the present invention may be any cancer without particular limitations. Specific examples thereof can include stomach cancer, lung adenocarcinoma, pancreatic cancer, and colon cancer. In the present invention, any of primary foci and metastatic foci of these cancers can be diagnosed.

In the present invention, when the protein is detected in the test sample, cancer is diagnosed with its level as an index. Specifically, when the amount of the TM4SF20 protein detected in the test sample is larger than that of a negative control or a healthy individual, the test subject is shown to have cancer or possibly have cancer in the future. Specifically, the present invention relates to a method for diagnosing cancer, comprising the following steps:
(1) detecting the expression level of TM4SF20 in a biological sample collected from a test subject, and
(2) comparing the expression level of TM4SF20 detected in the step (1) with that of a control, wherein when the expression level of TM4SF20 is higher than that of the control, the test subject is shown to have cancer.

In the present invention, the control refers to a reference sample for comparison and encompasses negative controls and biological samples of healthy individuals. The negative controls can be obtained by collecting biological samples of healthy individuals and mixing them, if necessary. The expression level of TM4SF20 in the control can be detected in parallel with the detection of the expression level of TM4SF20 in the biological sample of the test subject. Alternatively, the expression level of TM4SF20 in a large number of biological samples of healthy individuals can be detected in advance to statistically determine the standard expression level in the healthy individuals. Specifically, for example, mean±2× standard deviation (S.D.) or mean±3× standard deviation (S.D.) can also be used as the standard value. Statistically, the mean±2× standard deviation (S.D.) and the mean±3× standard deviation (S.D.) include 80% and 90% of the healthy individuals, respectively.

Alternatively, the expression level of TM4SF20 in the control can be set using an ROC curve. The ROC curve, or receiver operating characteristic curve, is a graph showing detection sensitivity in the ordinate and false positive rates (i.e., "1-specificity") in the abscissa. In the present invention, the ROC curve can be obtained by plotting changes in sensitivity and false positive rate at a series of varying reference values for determining the expression level of TM4SF20 in biological samples.

The "reference value" for obtaining the ROC curve is a numeric value temporarily used for statistical analysis. In general, the "reference value" for obtaining the ROC curve is serially varied within a range which can cover all selectable reference values. For example, the reference value can be varied between the minimal and maximal measured values of TM4SF20 in a population to be analyzed.

A standard value that can be expected to offer the desired detection sensitivity and precision can be selected based on the obtained ROC curve. The standard value statistically set based on the ROC curve or the like is also called a cut-off value. In a method for detecting cancer based on the cut-off value, the step (2) comprises comparing the expression level of TM4SF20 detected in the step (1), with the cut-off value. Then, when the expression level of TM4SF20 detected in the step (1) is higher than the cut-off value, cancer is detected in the test subject.

In the present invention, the expression level of TM4SF20 can be determined by an arbitrary method. Specifically, the expression level of TM4SF20 can be determined by evaluating the amount of TM4SF20 mRNA, the amount of the TM4SF20 protein, and the biological activity of the TM4SF20 protein. The amount of the TM4SF20 mRNA or protein can be determined by a method as described in the present specification.

In the present invention, the test subject is particularly preferably a human. When a non-human animal is used as the test subject, a TM4SF20 protein derived from this animal species is detected.

A method for detecting the TM4SF20 protein contained in the test sample is not particularly limited and is preferably detection by an immunological method using the anti-TM4SF20 antibody as exemplified below:
enzyme-linked immunosorbent assay (ELISA),
radioimmunoassay (RIA),
enzyme immunoassay (EIA),
fluoroimmunoassay (FIA),
luminescent immunoassay (LIA),
immunoprecipitation (IP),
turbidimetric immunoassay (TIA),
western blotting (WB),
immunohistochemical (IHC) method,
single radial immunodiffusion (SRID),
dot blot, and
slot blot.

Among these approaches, the immunohistochemical (IHC) method is a immunological assay method preferable as a method for diagnosing cancer, comprising the step of detecting TM4SF20 proteins in sections in which a tissue or cells obtained from a patient having cancer is fixed. The immunological methods such as the immunohistochemical (IHC) method are methods generally known by those skilled in the art.

Since TM4SF20 is a membrane protein with enhanced expression specific for cancer cells, cancer cells or cancer tissues can be detected using the anti-TM4SF20 antibody. Cancer cells contained in cells or tissues collected from living bodies are detected by the immunohistological analysis.

In another preferable aspect, cancer tissues can also be detected in vivo using the anti-TM4SF20 antibody. This method specifically comprises the steps of: (1) administering, to a test subject, a labeling substance (e.g., radioisotope)-labeled antibody binding to a TM4SF20 protein; and (2) detecting the accumulation of the labeling substance. The antibody can be labeled detectably for tracing the antibody administered into the living body. For example, the antibody can be labeled with a fluorescent or luminescent material or a radioisotope, and its in vivo behavior can be traced. The antibody labeled with the fluorescent or luminescent material can be observed using an endoscope or peritoneoscope. The localization of the antibody can be imaged by tracing the radioactivity of the radioisotope. In the present invention, the in vivo localization of the anti-TM4SF20 antibody represents the presence of cancer cells.

A positron-emitting nuclide can be used as the radioisotope for labeling the antibody for in vivo cancer detection. For example, the antibody can be labeled with a positron-emitting nuclide such as $^{18}$F, $^{55}$Co, $^{64}$Cu, $^{66}$Ga, $^{68}$Ga, $^{76}$Br, $^{89}$Zr, and $^{124}$I. A method known in the art (Acta Oncol. 32, 825-830, 1993) can be used in the labeling of the anti-TM4SF20 antibody with these positron-emitting nuclides.

The anti-TM4SF20 antibody labeled with the positron-emitting nuclide is administered to humans or animals. Then, radiation emitted by the radionuclide is measured ex vivo using PET (positron emission tomograph) and converted to images by a computed tomographic approach. The PET is an apparatus for noninvasively obtaining data about in vivo drug behavior or the like. The PET can quantitatively image radiation intensity as signal intensity. By such use of the PET, antigen molecules highly expressed in particular cancer can be detected without collecting samples from patients. The anti-TM4SF20 antibody may be radiolabeled with a short-life nuclide using a positron-emitting nuclide such as 11C, 13N, 15O, 18F, and 45Ti, in addition to the nuclides described above.

Research and development have been pursued as to, for example, techniques of producing short-life nuclides using a medical cyclotron and the nuclides described above or producing short-life radiolabeling compounds. The anti-TM4SF20 antibody can be labeled with various radioisotopes by these techniques. The anti-TM4SF20 antibody administered to patients accumulates in primary foci and metastatic foci according to the specific of the anti-TM4SF20 antibody for pathological tissues at each site. When the anti-TM4SF20 antibody is labeled with the positron-emitting nuclide, its radioactivity can be detected to detect the presence of the primary foci and the metastatic foci based on the localization of the radioactivity. An active value of gamma radiation or positron emission of 25 to 4000 keV can be used appropriately for the diagnostic use. Moreover, therapeutic effect can also be expected by selecting an appropriate nuclide and administering the selected nuclide in larger amounts. A nuclide that provides a value of gamma radiation or positron emission of 70 to 700 keV can be used for obtaining anticancer effect attributed to radiation.

6.2 Detection of TM4SF20 Gene

In an alternative aspect of the method of the present invention, the expression of the TM4SF20 gene is detected. In the present invention, the detected gene is not particularly limited and is preferably mRNA. In the present invention, the detection encompasses quantitative or qualitative detection. Examples of the qualitative detection can include the following assay procedures:
simple assay on the presence or absence of the TM4SF20 mRNA,
assay on the presence or absence of more than a predetermined amount of the TM4SF20 mRNA, and
assay comprising comparing the amount of the TM4SF20 mRNA with that contained in another sample (e.g., a control sample).

On the other hand, examples of the quantitative detection can include measurement of a TM4SF20 mRNA concentration and measurement of the amount of the TM4SF20 mRNA.

In the present invention, an arbitrary sample likely to contain the TM4SF20 mRNA can be used as the test sample. Samples collected from living bodies such as mammals are preferable. Samples collected from humans are more preferable. Specific examples of the test sample can include blood, interstitial fluid, plasma, extravascular fluid, cerebrospinal fluid, synovial fluid, pleural fluid, serum, lymph, saliva, urine, and tissues. The sample is preferably a preparation in which a tissue or cells collected from a living body is fixed, or a sample obtained from the test sample, such as a cell culture medium. These samples are encompassed by the test sample of the present invention.

When a sample obtained from the test sample is used, such as a preparation in which a tissue or cells collected from a living body is fixed, or a cell culture medium, in situ hybridization is preferably used. The in situ hybridization has been evolved as an approach for confirming the presence or absence or distribution of particular DNA or RNA in cells or tissues, and the strength of its expression. This method employs the principles on which a probe nucleic acid having a nucleotide sequence complementary to an intracellular particular nucleic acid sequence has the property of specifically forming a complex. The probe is labeled in advance with a radioisotope (RI), an antigenic substance ((hapten), or the like. As a result, the hybridization site can be distinguished through the detection of the label. Thus, the in situ hybridization is used in, for example, the detection of intracellular DNA or RNA, or the like. Labeling with RI can be used preferably as the probe labeling. Furthermore, for example, fluorescence labeling with a nonradioactive substance such as biotin or hapten (e.g., digoxigenin) can be used more preferably. For example, a detection method by fluorescence in situ hybridization called FISH is particularly preferably used.

The diagnosed cancer is not particularly limited. Specific examples thereof can include stomach cancer, lung adenocarcinoma, pancreatic cancer, and colon cancer. In the present invention, any of primary foci and metastatic foci of these cancers can be diagnosed.

In the present invention, an arbitrary animal species expressing the TM4SF20 gene can be used as the test subject. The test subject is particularly preferably a human. When a non-human animal species is used as the test subject, a TM4SF20 gene derived from this animal species is detected.

Hereinafter, a specific aspect of the detection method will be described. First, a sample is prepared from a test subject. Subsequently, TM4SF20 mRNA contained in the sample is detected. In the present invention, cDNA synthesized from the mRNA can also be detected. In the present invention, when TM4SF20 mRNA or TM4SF20-encoding cDNA is detected in the test sample, the test subject is diagnosed as possibly having cancer. For example, when the amount of the TM4SF20 mRNA or TM4SF20-encoding cDNA detected in the test sample is larger than that in negative controls or healthy individuals, the test subject is shown to have cancer or highly possible have cancer in the future.

A method for detecting the mRNA is known in the art. Specific examples of the method that can be used in the present invention include: nucleic acid hybridization using samples immobilized on a solid phase selected from gene chips, cDNA arrays, and membrane filters; RT-PCR; real-time PCR; subtraction method; differential display method; differential hybridization; and cross hybridization.

The detection method of the present invention can be automated using various automatic detectors. Such automation achieves detection of a large number of samples in a short time.

6.3 Diagnostic Drug, Reagent, and Kit

The present invention also provides a diagnostic drug or a kit for cancer diagnosis, comprising a reagent for detecting a TM4SF20 protein in a test sample. The diagnostic drug of the present invention comprises at least the anti-TM4SF20 antibody.

The reagent for cancer diagnosis of the present invention can be combined with other factors used in TM4SF20 detection to prepare a kit for cancer diagnosis. Specifically, the present invention relates to a kit for cancer diagnosis, which comprises: an antibody binding to TM4SF20; and a reagent for detecting the binding of the antibody to TM4SF20 and may further comprise a control sample comprising a biological sample containing TM4SF20. A manual for instruction of assay procedures may further be included in the kit of the present invention.

Hereinafter, the present invention will be described specifically with reference to Examples. However, the present invention is not intended to be limited to these Examples.

Example 1

Analysis of TM4SF20 mRNA Expression

The expression of TM4SF20 mRNA in clinical cancers, cancer cell lines, and normal tissues was analyzed using Human Exon 1.0 ST Array or Human Genome U133 Set and Human Genome U133 Plus 2.0 Array (all, Affymetrix, Inc.). The expression analysis using Human Exon 1.0 ST Array was conducted according to GeneChip Whole Transcript (WT) Sense Target Labeling Assay Manual (Affymetrix, Inc.) using 1 μg of total RNA of each sample shown in FIG. 1. The data was digitized using ExACT (Exon Array Computational Tool) software (Affymetrix, Inc.). The expression analysis using Human Genome U133 Set and Human Genome U133 Plus 2.0 Array was conducted according to Expression Analysis Technical Manual (Affymetrix, Inc.) using 10 μg of total RNA of each sample shown in FIG. 2. The normal tissue-derived total RNAs were purchased from Clontech Laboratories, Inc., Ambion, Inc., STRATAGENE, Cell APPLICATIONS, Inc., Panomics Inc., CHEMICON, and BioChain Institute, Inc. For tumor or normal sites of the clinical cancer samples (after obtainment of informed consent) and the cancer cell lines, total RNA was purified using Trizol (Invitrogen Corp.) or Isogen (Nippon Gene Co., Ltd.) according to the protocol included in the product.

For the Human Exon 1.0 ST Array, expression data was defined as the mean of numeric values obtained using core probe sets (probe set IDs: 2602308, 2602309, 2602310, 2602312, and 2602315) designed for coding regions. The expression data obtained from normal tissues, cancer cell lines, clinical stomach cancers, and clinical lung adenocarcinomas are shown in FIG. 1. The clinical stomach cancer samples include intestinal types (sample Nos.: stomach 102t, 106t, 107t, 109t, 111t, and 27t), scirrhous types (stomach 103t, 108t, 112t, 113t, 52t, 78t, 87t, and 167t), and other types (stomach 105t and 101t).

Figure 2:
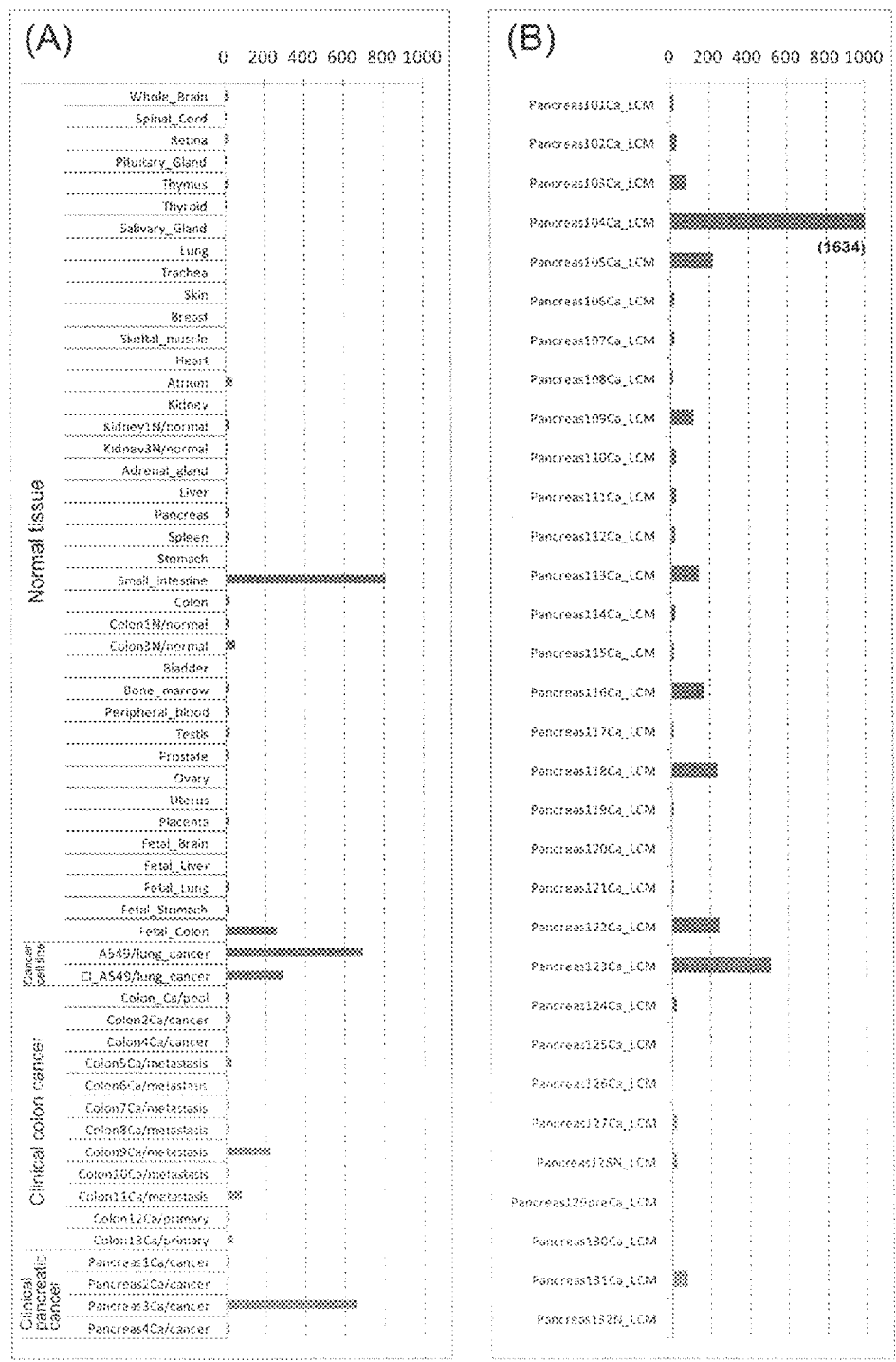
FIG. 2(A) is a diagram showing the expression profile of TM4SF20 mRNA obtained using Human Genome U133 Set.
FIG. 2(B) is a diagram showing the expression profile of TM4SF20 mRNA in clinical pancreatic cancer tissues obtained using Human Genome U133 Plus 2.0 Array.

For the Human Genome U133 Set and the Human Genome U133 Plus 2.0 Array, expression data was defined as a numeric value obtained using a probe for TM4SF20 (probe ID: 220639_at). The expression data obtained from normal tissues, cancer cell lines, clinical colon cancers, and clinical pancreatic cancers are shown in FIG. 2.

As a result of these expression analyses, TM4SF20 is hardly expressed in normal tissues other than the small intestine and the fetal large intestine, whereas its expression was confirmed in cancers: a pancreatic cancer cell line AsPC-1, a lung adenocarcinoma cell line A549, clinical stomach cancers (including intestinal types and scirrhous types), clinical lung adenocarcinomas, clinical colon cancers, and clinical pancreatic cancers. These results demonstrated that TM4SF20 serves as a therapeutic target molecule or a diagnostic marker for stomach cancer, lung adenocarcinoma, pancreatic cancer, and colon cancer.

Example 2

Preparation of Antibody Against TM4SF20

1. Cloning of TM4SF20

Total RNA was extracted from a cancer cell line A549 (JCRB) using Trizol (Invitrogen Corp.). Further, cDNA was prepared using SuperScript III Reverse Transcriptase (Invitrogen Corp.) according to the protocol included in the product. This cDNA was used as a template to perform PCR amplification using a primer represented by SEQ ID NO: 1 (NotI recognition sequence-Kozak sequence-TM4SF20 5'-terminal sequence) and a primer represented by SEQ ID NO: 2 (XbaI recognition sequence-TM4SF20 3'-terminal sequence). The amplification product was cloned into pGEM-T Easy vectors using pGEM-T Easy Vector Systems (Promega Corp.) (the resultant vectors were designated as pGEM-T_TM4SF20). In the PCR amplification, KOD Plus Ver. 2 (TOYOBO CO., LTD.) was used, and a solution containing 5 μL of 10×KOD Plus Ver. 2 buffer, 5 μL of dNTP mixture, 3 μL of 25 mM MgSO$_4$, 1.5 μL of the primer of SEQ ID NO: 1 (10 μM), 1.5 μL of the primer of SEQ ID NO: 2 (10 μM), 2.5 μL of A549 cDNA, 1 μL of KOD Plus Polymerase, and 30.5 μL nuclease-free water was prepared, followed by amplification involving 94° C. for 2 minutes, (98° C. for 10 seconds, 72° C. for 30 seconds, and 68° C. for 2 minutes)×5 cycles, (98° C. for 10 seconds, 70° C. for 30 seconds, and 68° C. for 2 minutes)×5 cycles, (98° C. for 10 seconds and 68° C. for 2 minutes)×25 cycles, and 72° C. for 7 minutes. The pGEM-T_TM4SF20 was sequenced to confirm that its sequence was the same as that of RefSeq Accession No. NM_024795.3.

2. Preparation of Expression Vector for DNA Immunization

TM4SF20 cDNA was cloned into expression vectors for mammalian cells (pMC and pCOS2). The pMC is a vector that is capable of inducing expression under the control of a mouse CMV promoter (GenBank Accession No. U68299). The pCOS2 is a vector that is capable of inducing expression under the control of a human EEF1A1 promoter (GenBank Accession No. NM_001402) and has a neomycin resistance gene incorporated therein. pGEM-T_TM4SF20 was digested with NotI and XbaI and cloned into the NotI-XbaI sites of pMC and pCOS2 (the resultant vectors were designated as pMC_TM4SF20 and pCOS2_TM4SF20, respectively).

3. Preparation of TM4SF20-Expressing Ba/F3 Cell Line

TM4SF20 cDNA was cloned into expression vectors for mammalian cells (pMCDN2_ntHA). The pMCDN2_ntHA is a vector that is capable of inducing expression under the control of a mouse CMV promoter and has a neomycin resistance gene incorporated therein. Moreover, an HA tag sequence is added to the 5' end of the inserted gene of interest. The HA tag sequence is an HA epitope sequence (YPYDVP-DYA) derived from influenza hemagglutinin proteins and is recognized by HA-specific antibodies. pGEM-T_TM4SF20 was used as a template to perform PCR amplification using a primer represented by SEQ ID NO: 3 (NheI recognition sequence-TM4SF20 5'-terminal sequence except for start codon) and a primer represented by SEQ ID NO: 4 (NotI recognition sequence-TM4SF20 3'-terminal sequence except for stop codon). The amplification fragment was digested with NheI and NotI and cloned into the NheI-NotI site of pMCDN2_ntHA (the resultant vector was designated as pMCDN2_TM4SF20_ntHA). The nucleotide sequence from the start codon to stop codon of the pMCDN2_TM4SF20_ntHA is shown in SEQ ID NO: 5, and its amino acid sequence is shown in SEQ ID NO: 6.

The pMCDN2_TM4SF20_ntHA was digested with PvuI, and the digestion product was introduced into a mouse B cell line Ba/F3 (RIKEN, Japan) by electroporation. The cell line was screened using 500 μg/mL Geneticin (Invitrogen Corp.) to establish a Ba/F3 cell line constantly expressing N-terminally HA-tagged TM4SF20 (this cell line was designated as TM4SF20_Ba/F3). An RPMI1640 medium (Invitrogen Corp.) containing 500 μg/mL Geneticin, 1 ng/mL mouse IL-3

(R&D Systems), 10% fetal bovine serum (FBS, Invitrogen Corp.), and penicillin/streptomycin (Invitrogen Corp.) was used in culture.

4. Preparation of Anti-TM4SF20 Antibody

For MRL/MpJUmmCrj-lpr/lpr mice (male, 6-week-old, Charles River Laboratories Japan, Inc.), DNA immunization was performed twice a week (10 times in total; day O-day 32) using Helios Gene Gun (Bio-Rad Laboratories, Inc.) according to the protocol included in the product. In the DNA immunization, pMC_TM4SF20 and pCOS2_TM4SF20 expression vectors were concurrently used. Following the DNA immunization, $5 \times 10^6$ TM4SF20_Ba/F3 cells were administered to the tail veins (day 35). Then, to one of the mice, TM4SF20_Ba/F3 cells were administered again to the tail vein on day 42. Four days later, spleen cells were excised therefrom. To another mouse, TM4SF20_Ba/F3 cells were administered again to tail vein on day 63. Three days later, spleen cells were excised therefrom. Both the spleen cells were separately mixed with a mouse myeloma cell line P3-X63Ag8U1 (P3U1, ATCC) at a ratio of 3:1 to 4:1. PEG1500 (Roche Diagnostics GmbH) was gradually added to the mixture to prepare hybridomas. After addition of an RPMI1640 medium and centrifugation, the supernatant was removed to remove PEG1500. Next, the hybridomas were suspended in a HAT medium (RPMI1640 medium containing 10% FBS, penicillin-streptomycin, 1×HAT media supplement (Sigma-Aldrich Corp.), and 0.5×BM-Condimed H1 Hybridoma Cloning Supplement (Roche Diagnostics GmbH)) and inoculated to eight 96-well plates at a concentration of $1 \times 10^5$ P3U1 cells/well. These hybridomas were cultured at 37° C. for 7 days in a 5% $CO_2$ incubator, and the culture supernatant was then used in screening. The screening was performed by determining the binding of antibodies contained in the culture supernatant to TM4SF20_Ba/F3 cells and their parental strain Ba/F3 cells using a flow cytometer (FACS Calibur, Becton, Dickinson and Company). The hybridomas in wells specifically bound to the TM4SF20_Ba/F3 cells were continuously cultured and screened again in the same way as above. Then, the selected hybridomas were cloned as single clones by a limiting dilution method. In this way, clones B8, B11, B12, B15, C7, and C9 were established as antibodies specifically binding to TM4SF20.

These hybridomas were cultured in a HAT medium containing Ultra Low IgG FBS (Invitrogen Corp.) instead of FBS, and antibodies were purified from the culture supernatant using HiTrap Protein G HP column (GE Healthcare BioSciences Corp.). As a result of isotyping the purified antibodies using Isostrip (Roche Diagnostics GmbH), B11, B12, C7, and C9 were mouse IgG1κ; B15 was mouse IgG2aκ; and B8 was mouse IgG2bκ. The antibody concentrations were measured using DC Protein Assay Kit I (Bio-Rad Laboratories, Inc.). Bovine γ globulin included therein was used as standards. These procedures of antibody purification, isotyping, and antibody concentration measurement were carried out according to the protocol included in the product.

Example 3

Evaluation of Binding of Anti-TM4SF20 Antibody to Mouse TM4SF20

1. Cloning of Mouse TM4SF20 (mTM4SF20)

Mouse Normal Tissue Small Intestine cDNA (Cosmo Bio Co., Ltd.) was used as a template to perform PCR amplification using a primer represented by SEQ ID NO: 7 (mTM4SF20 5'-terminal sequence) and a primer represented by SEQ ID NO: 8 (mTM4SF20 3'-terminal sequence). The amplification product was cloned into pGEM-T Easy vectors using pGEM-T Easy Vector Systems (Promega Corp.) (the resultant vectors were designated as pGEM-T_mTM4SF20). In the PCR amplification, KOD Plus Ver. 2 (TOYOBO CO., LTD.) was used, and a solution containing 5 μL of 10×KOD Plus Ver. 2 buffer, 5 μL of dNTP mixture, 3 μL of 25 mM $MgSO_4$, 1.5 μL of the primer of SEQ ID NO: 7 (10 μM), 1.5 μL of the primer of SEQ ID NO: 8 (10 μM), 2 μL of mouse small intestine cDNA, 1 μL of KOD Plus Polymerase, and 31 μL nuclease-free water was prepared, followed by amplification involving 94° C. for 2 minutes and (98° C. for 10 seconds, 57° C. for 30 seconds, and 68° C. for 1 minute)×27 cycles. The pGEM-T_mTM4SF20 was sequenced to confirm that its sequence differed from that registered in GenBank (RefSeq Accession No. NM_025453.3) by 4 bases between their nucleotide sequences and by 2 amino acids between their amino acid sequences. The nucleotide sequence of the cloned mTM4SF20 is shown in SEQ ID NO: 9, and its amino acid sequence is shown in SEQ ID NO:10.

2. Preparation of mTM4SF20-Expressing CHO Cell Line mTM4SF20 cDNA was cloned into pMCDN2_ntHA. pGEM-T_mTM4SF20 was used as a template to perform PCR amplification using a primer represented by SEQ ID NO:11 (NheI recognition sequence-mTM4SF20 5'-terminal sequence except for start codon) and a primer represented by SEQ ID NO: 12 (NotI recognition sequence-mTM4SF20 3'-terminal sequence except for stop codon). The amplification fragment was digested with NheI and NotI and cloned into the NheI-NotI site of pMCDN2_ntHA (the resultant vector was designated as pMCDN2_mTM4SF20_ntHA).

Subsequently, mTM4SF20_ntHA cDNA was cloned into pCOS2. The pMCDN2_mTM4SF20_ntHA was used as a template to perform PCR amplification using a primer represented by SEQ ID NO: 13 (NotI recognition sequence-mTM4SF20_ntHA 5'-terminal sequence) and a primer represented by SEQ ID NO: 14 (BamHI recognition sequence-mTM4SF20_ntHA 3'-terminal sequence except for NotI recognition sequence). The amplification fragment was digested with NotI and BamHI and cloned into the NotI-BamHI site of pCOS2 (the resultant vector was designated as pCOS2_mTM4SF20_ntHA). The nucleotide sequence from the start codon to stop codon of the pCOS2_mTM4SF20_ntHA is shown in SEQ ID NO: 15, and its amino acid sequence is shown in SEQ ID NO: 16.

The pCOS2_mTM4SF20_ntHA was digested with PvuI, and the digestion product was introduced into a CHO cell line DG44 by electoporation. The cell line was screened using Geneticin (500 μg/mL) to establish a CHO cell line constantly expressing N-terminally HA-tagged mTM4SF20 (this cell line was designated as mTM4SF20_CHO). A CHO-S-SFM II medium (Invitrogen Corp.) containing 500 μg/mL Geneticin, HT supplement (Invitrogen Corp.), and penicillin/streptomycin (Invitrogen Corp.) (hereinafter, referred to as a CHO medium) was used in culture.

3. Preparation of TM4SF20-Expressing CHO Cell Line

TM4SF20 cDNA was cloned into expression vectors for mammalian cells (pCOS2_ctHA). The pCOS2_ctHA is a vector that is capable of inducing expression under the control of a mouse CMV promoter and has a neomycin resistance gene incorporated therein. An HA tag sequence is added to the 3' end of the inserted gene of interest. pMC_TM4SF20 was used as a template to perform PCR amplification using a primer represented by SEQ ID NO: 1 (NotI recognition sequence-Kozak sequence-TM4SF20 5'-terminal sequence) and a primer represented by SEQ ID NO: 17 (BamHI recognition sequence-TM4SF20 3'-terminal sequence except for stop codon). The amplification fragment was digested with NotI and BamHI and cloned in the NotI-BamHI site of pCOS2_ctHA (the resultant vector was designated as (pCOS2_TM4SF20_ctHA). The nucleotide sequence from the start codon to stop codon of the pCOS2_TM4SF20_ctHA is shown in SEQ ID NO: 18, and its amino acid sequence is shown in SEQ ID NO: 19.

The pCOS2_TM4SF20_ctHA was digested with PvuI, and the digestion product was introduced into DG44 cells by electroporation. The cell line was screened using Geneticin (500 μg/mL) to establish a CHO cell line constantly expressing C-terminally HA-tagged TM4SF20 (this cell line was designated as TM4SF20_CHO). A CHO medium was used in culture.

4. Evaluation of Binding of Anti-TM4SF20 Antibody to mTM4SF20

Each anti-TM4SF20 antibody prepared in Example 2 was evaluated for its binding to mTM4SF20 by flow cytometry. Cells used were mTM4SF20_CHO, TM4SF20_CHO as a positive control, and DG44 cells as a negative control.

Figure 3:
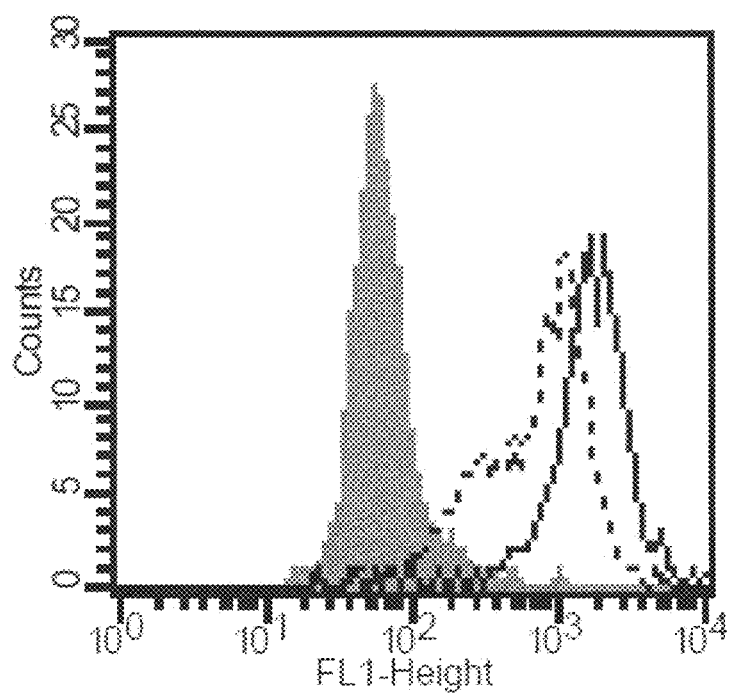
FIG. 3 is a diagram showing results of evaluating the binding of an anti-HA antibody to TM4SF20_CHO (solid line), mTM4SF20_CHO (dotted line), and DG44 cells (gray filled line) by flow cytometry.

First, mTM4SF20 or TM4SF20 expression in each cell was confirmed by flow cytometry using an anti-HA antibody. The mTM4SF20 and the TM4SF20 are four-transmembrane proteins whose N and C termini are both intracellularly located. Thus, the HA tag is also intracellularly located. For the delivery of the anti-HA antibody into the cells, these cells were treated with Intrastain (Dako) according to the protocol included in the product to make their cell membrane permeable. An FITC-labeled anti-HA antibody (Sigma-Aldrich Corp.) was added at a concentration of 3 μg/mL to the Intrastain-treated cells ($5 \times 10^4$ cells/well, U-bottom 96-well plate). After reaction at room temperature for 15 minutes, the cells were washed with PBS containing 0.5% bovine serum albumin and 0.1% $NaN_3$ (FACS buffer). The cells were suspended in FACS buffer and assayed using a flow cytometer (FACS Calibur, Becton, Dickinson and Company). The assay data was analyzed using CELLQuest software (Becton, Dickinson and Company). As a result, the mTM4SF20_CHO and TM4SF20_CHO cells were confirmed to express antigens at the same levels (FIG. 3).

Figure 4:
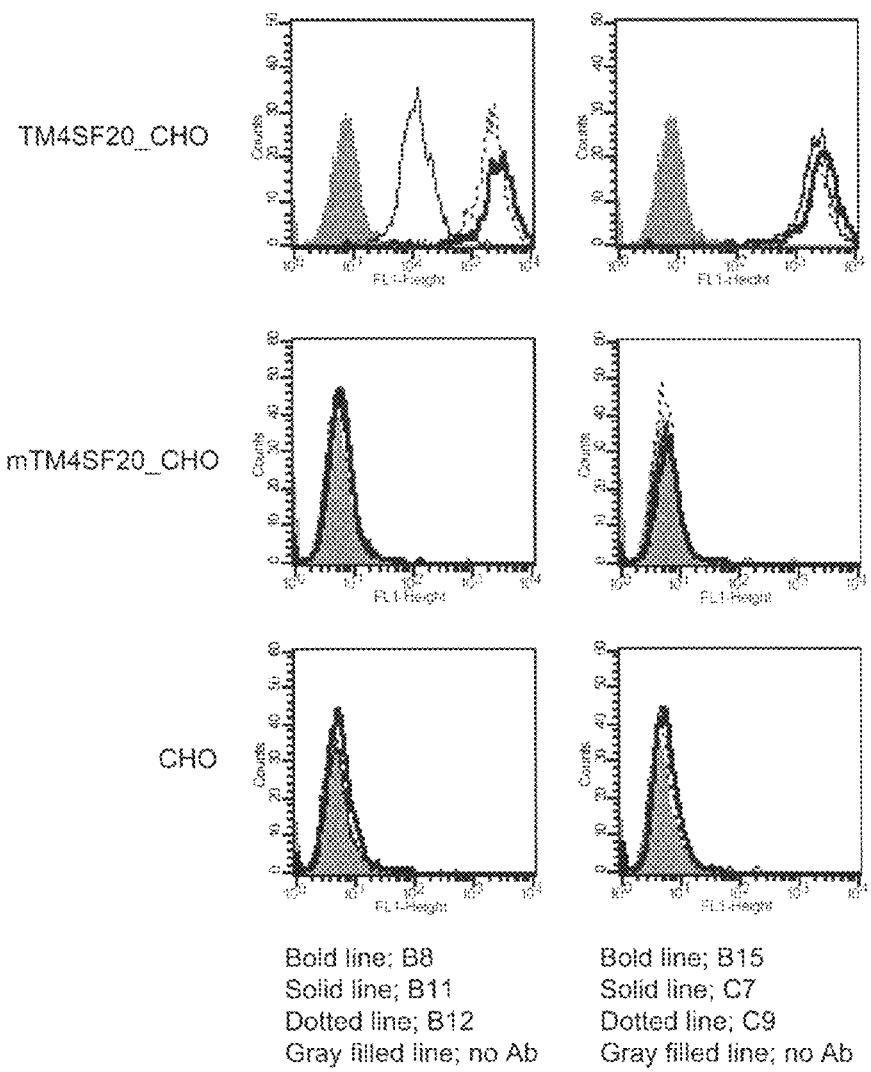
FIG. 4 is a diagram showing results of evaluating the binding of an anti-TM4SF20 antibody to TM4SF20_CHO, mTM4SF20_CHO, and DG44 cells by flow cytometry.

Next, $5 \times 10^4$ cells suspended in FACS buffer were dispensed to a U-bottom 96-well plate. The anti-TM4SF20 antibody (hybridoma culture supernatant) or the HAT medium as a negative control was added thereto at a concentration of 10 μg/mL. After reaction on ice for 1 hour, the cells were washed with FACS buffer. Next, an FITC-labeled anti-mouse antibody (Goat F(ab')$_2$ Fragment Anti-mouse IgG (H+L)-FITC, Beckman Coulter, Inc.) was added thereto as a secondary antibody and reacted on ice for 1 hour. The cells were washed with FACS buffer, then suspended in FACS buffer supplemented with 10 μg/mL propidium iodide (PI, Sigma-Aldrich Corp.), and assayed using a flow cytometer. The assay data was analyzed as to PI-negative cell populations using CELLQuest software. As a result, all the clones bound to TM4SF20_CHO but to neither mTM4SF20_CHO nor DG44 cells (FIG. 4).

Example 4

Flow Cytometry Analysis of Epitope for Anti-TM4SF20 Antibody

For analyzing epitopes for each anti-TM4SF20 antibody prepared in Example 2, the sequence of the first loop (amino acids 36-44) or the second loop (amino acids 105-185) (all from UniProt accession number Q53R12), of two extracellular loops of TM4SF20, was substituted by the corresponding sequence of mTM4SF20 (chimeric TM4SF20). This protein was expressed in CHO cells and analyzed for the binding of the anti-TM4SF20 antibody by flow cytometry.

1. Preparation of Chimeric TM4SF20 Version 1-Expressing CHO Cell Line

The cDNA of chimeric TM4SF20 comprising the first loop substituted by that of mTM4SF20 (hereinafter, referred to as chimeric TM4SF20 version 1) was cloned into pMCDN2_ntHA. pGEM-T_TM4SF20 was used as a template to perform PCR amplification using a primer represented by SEQ ID NO: 3 (NheI recognition sequence-TM4SF20 5'-terminal sequence except for start codon) and a primer represented by SEQ ID NO: 20 (TM4SF20 sequence comprising the first loop substituted by that of mTM4SF20). Likewise, pGEM-T_TM4SF20 was used as a template to perform PCR amplification using a primer represented by SEQ ID NO: 21 (TM4SF20 sequence comprising the first loop substituted by that of mTM4SF20) and a primer represented by SEQ ID NO: 4 (NotI recognition sequence-TM4SF20 3'-terminal sequence except for stop codon). These two amplification fragments were used as a template to perform PCR amplification using a primer represented by SEQ ID NO: 3 and a primer represented by SEQ ID NO: 4. The amplification fragment was digested with NheI and NotI and cloned into the NheI-NotI site of pMCDN2_ntHA (the resultant vector was designated as pMCDN2_chimeric TM4SF20 ver.1_ntHA).

Subsequently, chimeric TM4SF20 ver.1_ntHA cDNA was cloned into pCOS2. The pMCDN2_chimeric TM4SF20 ver.1_ntHA was used as a template to perform PCR amplification using a primer represented by SEQ ID NO: 13 (NotI recognition sequence-chimeric TM4SF20 ver.1_ntHA 5'-terminal sequence) and a primer represented by SEQ ID NO: 22 (BamHI recognition sequence-chimeric TM4SF20 ver.1_ntHA 3'-terminal sequence except for NotI recognition sequence). The amplification fragment was digested with NotI and BamHI and cloned into the NotI-BamHI site of pCOS2 (the resultant vector was designated as pCOS2_chimeric TM4SF20 ver.1_ntHA). The nucleotide sequence from the start codon to stop codon of the pCOS2_chimeric TM4SF20 ver.1_ntHA is shown in SEQ ID NO: 23, and its amino acid sequence is shown in SEQ ID NO: 24.

The pCOS2_chimeric TM4SF20 ver.1_ntHA was digested with PvuI, and the digestion product was introduced into DG44 cells by electroporation. The cell line was screened using Geneticin (500 μg/mL) to establish a CHO cell line constantly expressing N-terminally HA-tagged chimeric TM4SF20 ver.1 (this cell line was designated as chimeric TM4SF20 ver.1_CHO). A CHO medium was used in culture.

2. Preparation of Chimeric TM4SF20 Version 2-Expressing CHO Cell Line

The cDNA of chimeric TM4SF20 comprising the second loop substituted by that of mTM4SF20 (hereinafter, referred to as chimeric TM4SF20 version 2) was cloned into pMCDN2_ntHA. pGEM-T_mTM4SF20 was used as a template to perform PCR amplification using a primer represented by SEQ ID NO: 25 (sequence immediately before TM4SF20 second loop-mTM4SF20 second loop 5'-terminal sequence) and a primer represented by SEQ ID NO: 26 (sequence immediately after TM4SF20 second loop-mTM4SF20 second loop 3'-terminal sequence). Moreover, pGEM-T_TM4SF20 was used as a template to perform PCR amplification using a primer represented by SEQ ID NO: 3 (NheI recognition sequence-TM4SF20 5'-terminal sequence except for start codon) and a primer represented by SEQ ID NO: 27 (mTM4SF20 second loop 5'-terminal sequence-sequence immediately before TM4SF20 second loop). Likewise, pGEM-T_TM4SF20 was used as a template to perform PCR amplification using a primer represented by SEQ ID NO: 28 (mTM4SF20 second loop 3'-terminal sequence-sequence immediately after TM4SF20 second loop) and a primer represented by SEQ ID NO: 4 (NotI recognition sequence-TM4SF20 3'-terminal sequence except for stop codon). These three amplification fragments were used as a template to perform PCR amplification using a primer represented by SEQ ID NO: 3 and a primer represented by SEQ ID NO: 4. The amplification fragment was digested with NheI and NotI and cloned into the NheI-NotI site of pMCDN2_ntHA (the resultant vector was designated as pMCDN2_chimeric TM4SF20 ver.2_ntHA).

Subsequently, chimeric TM4SF20 ver.2_ntHA cDNA was cloned into pCOS2. The pMCDN2_chimeric TM4SF20 ver.2_ntHA was used as a template to perform PCR amplification using a primer represented by SEQ ID NO: 13 (NotI recognition sequence-chimeric TM4SF20 ver.2_ntHA 5'-terminal sequence) and a primer represented by SEQ ID NO: 22 (BamHI recognition sequence-chimeric TM4SF20 ver.2_ntHA 3'-terminal sequence except for NotI recognition sequence). The amplification fragment was digested with NotI and BamHI and cloned into the NotI-BamHI site of pCOS2 (the resultant vector was designated as pCOS2_chimeric TM4SF20 ver.2_ntHA). The nucleotide sequence from the start codon to stop codon of the pCOS2_chimeric TM4SF20 ver.2_ntHA is shown in SEQ ID NO: 29, and its amino acid sequence is shown in SEQ ID NO: 30.

The pCOS2_chimeric TM4SF20 ver.2_ntHA was digested with PvuI, and the digestion product was introduced into DG44 cells by electroporation. The cell line was screened using Geneticin (500 µg/mL) to establish a CHO cell line constantly expressing N-terminally HA-tagged chimeric TM4SF20 ver.2 (this cell line was designated as chimeric TM4SF20 ver.2_CHO). A CHO medium was used in culture.

3. Evaluation of Binding of Anti-TM4SF20 Antibody to Chimeric TM4SF20

Each anti-TM4SF20 antibody prepared in Example 2 was evaluated for its binding to chimeric TM4SF20 by flow cytometry. Cells used were chimeric TM4SF20 ver.1_CHO, chimeric TM4SF20 ver.2_CHO, and DG44 cells as a negative control.

Figure 5:
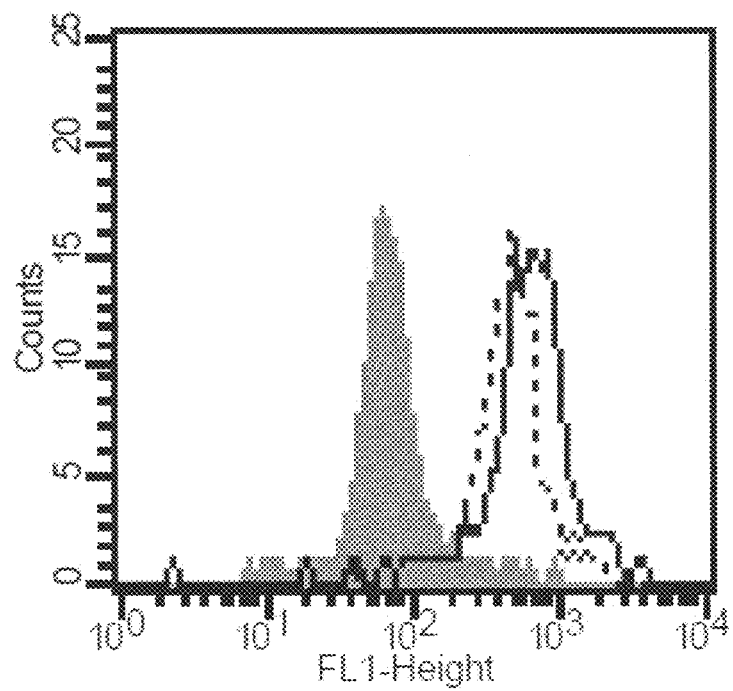
FIG. 5 is a diagram showing results of evaluating the binding of the anti-HA antibody to chimeric TM4SF20 ver.1_CHO (solid line), chimeric TM4SF20 ver.2_CHO (dotted line), and DG44 cells (gray filled line) by flow cytometry.

First, chimeric TM4SF20 expression in each cell was confirmed by flow cytometry using an anti-HA antibody. The flow cytometry was performed in the same way as in Example 3. As a result, the chimeric TM4SF20 ver.1_CHO and chimeric TM4SF20 ver.2_CHO cells were confirmed to express antigens at the same levels (FIG. 5).

Figure 6:
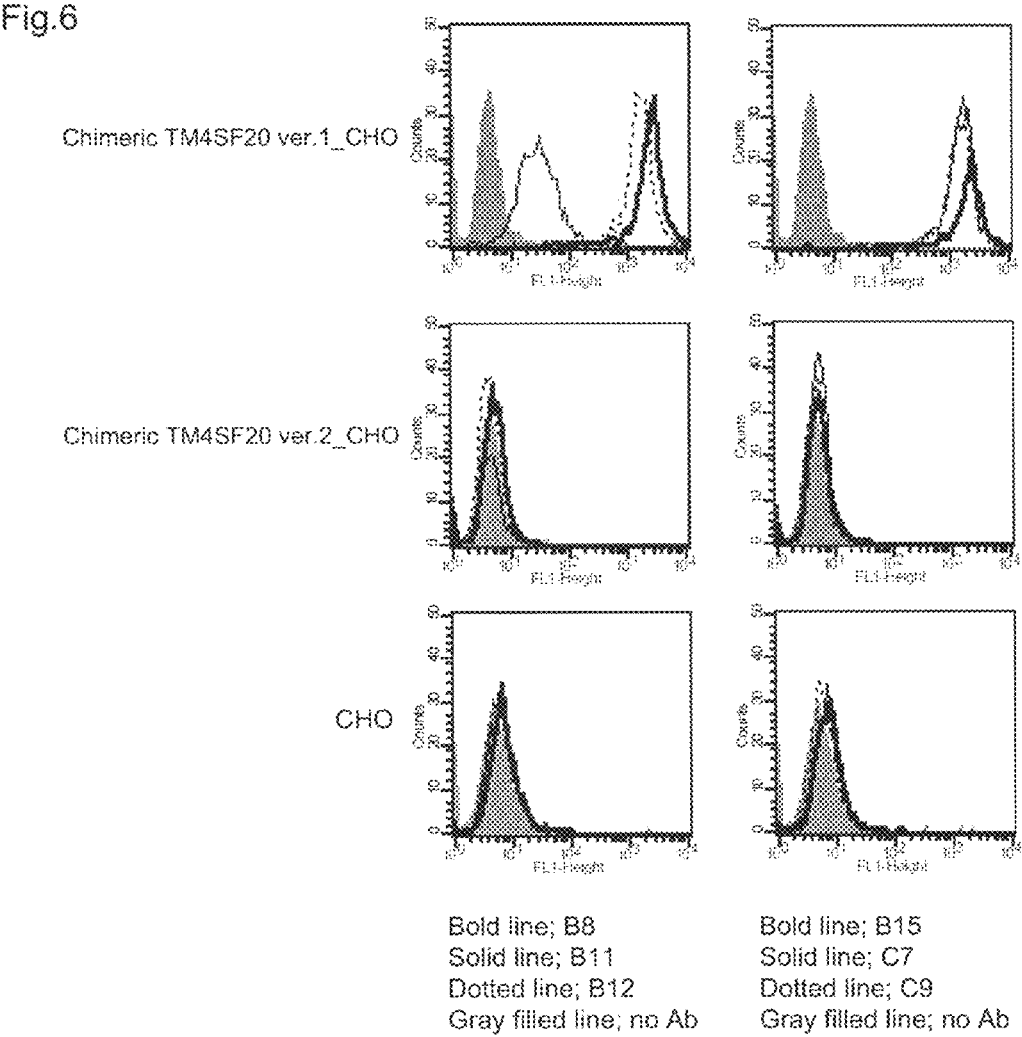
FIG. 6 is a diagram showing results of evaluating the binding of the anti-TM4SF20 antibody to chimeric TM4SF20 ver.1_CHO, chimeric TM4SF20 ver.2_CHO, and DG44 cells by flow cytometry.

Next, the binding of the anti-TM4SF20 antibody (hybridoma culture supernatant) was confirmed by flow cytometry in the same way as in Example 3. As a result, all the clones bound to chimeric TM4SF20 ver.1_CHO but to neither chimeric TM4SF20 ver.2_CHO nor DG44 cells (FIG. 6). These results demonstrated that these antibodies recognize the second loop of TM4SF20.

Example 5

Western Blotting Analysis of Epitope for Anti-TM4SF20 Antibody

For analyzing the epitope in more detail, peptides were prepared by deleting various amino acid sequences on the basis of 100 amino acids containing the TM4SF20 second loop (amino acids 101-200). These peptides were expressed in E. coli and evaluated for the binding of the anti-TM4SF20 antibody by western blotting.

Six peptides shown in a table below were prepared. All these peptides comprised a glutathione S-transferase (GST) tag attached to the 5' end and a His tag (6 consecutive histidine residues) attached to the 3' end. A forward primer (BamHI recognition sequence-TM4SF20 sequence) and a reverse primer (NotI recognition sequence-stop codon-His tag sequence-TM4SF20 sequence) used in the preparation are also shown in the table below.

TABLE 1

| Construct name | TM4SF20 amino acid No. | Forward primer (SEQ ID NO) | Reverse primer (SEQ ID NO) |
|---|---|---|---|
| GST_TM4SF20_N1 | 117-200 | F2 (31) | R1 (32) |
| GST_TM4SF20_N2 | 134-200 | F3 (33) | R1 |
| GST_TM4SF20_N3 | 151-200 | F4 (34) | R1 |
| GST_TM4SF20_C1 | 101-184 | F1 (35) | R2 (36) |
| GST_TM4SF20_C2 | 101-167 | F1 | R3 (37) |
| GST_TM4SF20_C3 | 101-150 | F1 | R4 (38) | pGEM-T_TM4SF20 was used as a template to perform PCR amplification using each set of these forward and reverse primers. Each amplification product was digested with BamHI and NotI and cloned into the BamHI-NotI site of GST fusion protein expression vectors (pGEX-6P-1, GE Healthcare Bio-Sciences Corp.). The nucleotide sequence from the BamHI recognition sequence to stop codon of each prepared construct and its amino acid sequence are shown in a table below.

TABLE 2

| Construct name | SEQ ID NO (nucleotide sequence) | SEQ ID NO (amino acid sequence) |
|---|---|---|
| GST_TM4SF20_N1 | 39 | 40 |
| GST_TM4SF20_N2 | 41 | 42 |
| GST_TM4SF20_N3 | 43 | 44 |
| GST_TM4SF20_C1 | 45 | 46 |
| GST_TM4SF20_C2 | 47 | 48 |
| GST_TM4SF20_C3 | 49 | 50 |

Each construct was expressed using BL21 (DE3) Competent Cells (Takara Bio Inc.). The whole cell lysate was electrophoresed by SDS-PAGE and then transferred to a PVDF membrane (Immobilon-P, Millipore Corp.) for western blotting. The construct was detected using the anti-TM4SF20 antibody (purified antibody) at a concentration of 5 µg/mL, a 3000 fold-diluted secondary antibody (HRP-anti mIgG, GE Healthcare Bio-Sciences Corp.), and ECL Western Blotting Detection Reagents (GE Healthcare Bio-Sciences Corp). The expression of each construct was confirmed using an anti-GST antibody (GE Healthcare Bio-Sciences Corp.) and an anti-His antibody (Santa Cruz Biotechnology, Inc.). Secondary antibodies used were a HRP-labeled anti-goat antibody (Invitrogen Corp.) and a HRP-labeled anti-rabbit antibody (GE Healthcare Bio-Sciences Corp.), respectively.

Figure 7:
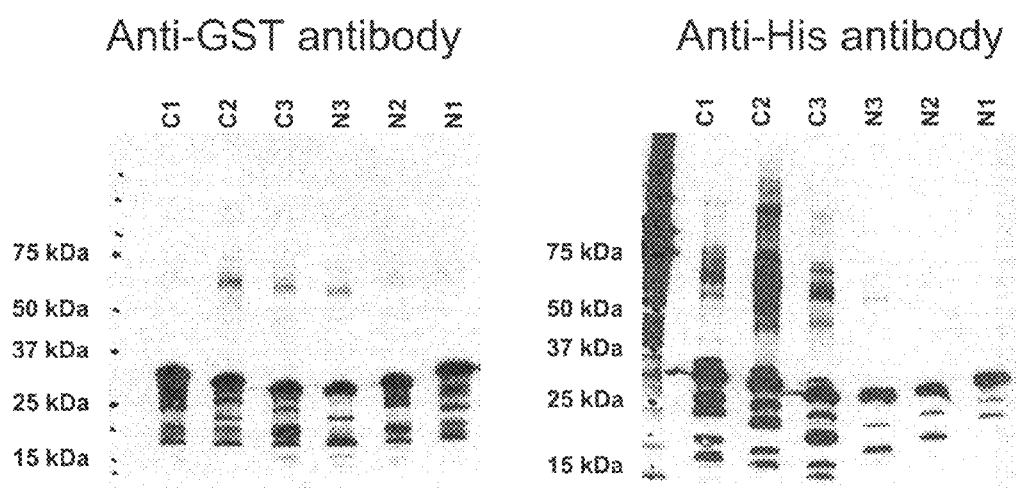
FIG. 7 is a diagram showing results of western blotting using anti-GST and anti-His antibodies. Whole cell lysates of *E. coli* expressing GST_TM4SF20_N1, GST_TM4SF20_N2, GST_TM4SF20_N3, GST_TM4SF20_C1, GST_TM4SF20_C2, or GST_TM4SF20_C3 were used as samples. In the diagram, they are indicated in N1, N2, N3, C1, C2, and C3, respectively.
Figure 8:
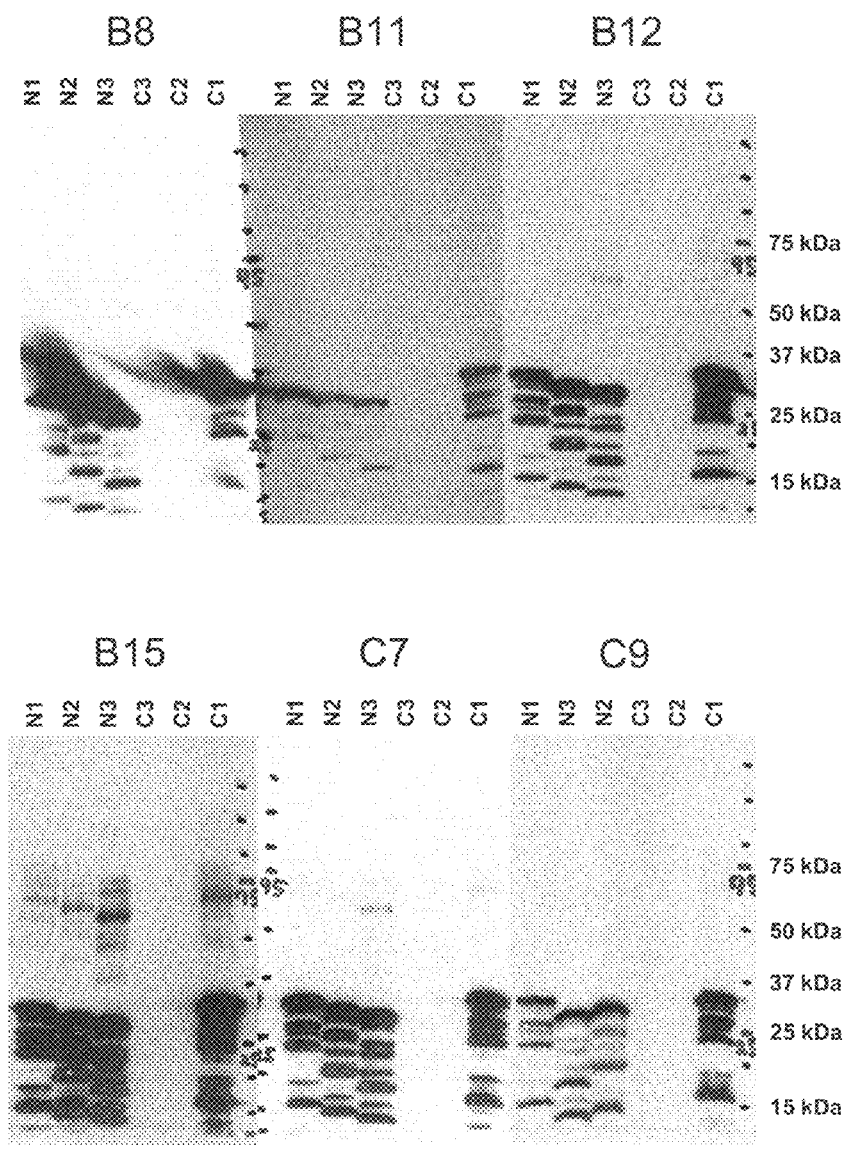
FIG. 8 is a diagram showing results of western blotting using the anti-TM4SF20 antibody. Whole cell lysates of *E. coli* expressing GST_TM4SF20_N1, GST_TM4SF20_N2, GST_TM4SF20_N3, GST_TM4SF20_C1, GST_TM4SF20_C2, or GST_TM4SF20_C3 were used as samples. In the diagram, they are indicated in N1, N2, N3, C1, C2, and C3, respectively.

As a result of western blotting using anti-GST and anti-His antibodies, all the constructs were confirmed to be expressed in E. coli (FIG. 7). All the anti-TM4SF20 antibody clones bound to neither GST_TM4SF20_C2 nor GST_TM4SF20_C3 (FIG. 8). These results demonstrated that the amino acid sequence of amino acids 168-184 in TM4SF20 serves as an epitope for all the clones.

Example 6

Figure 9:
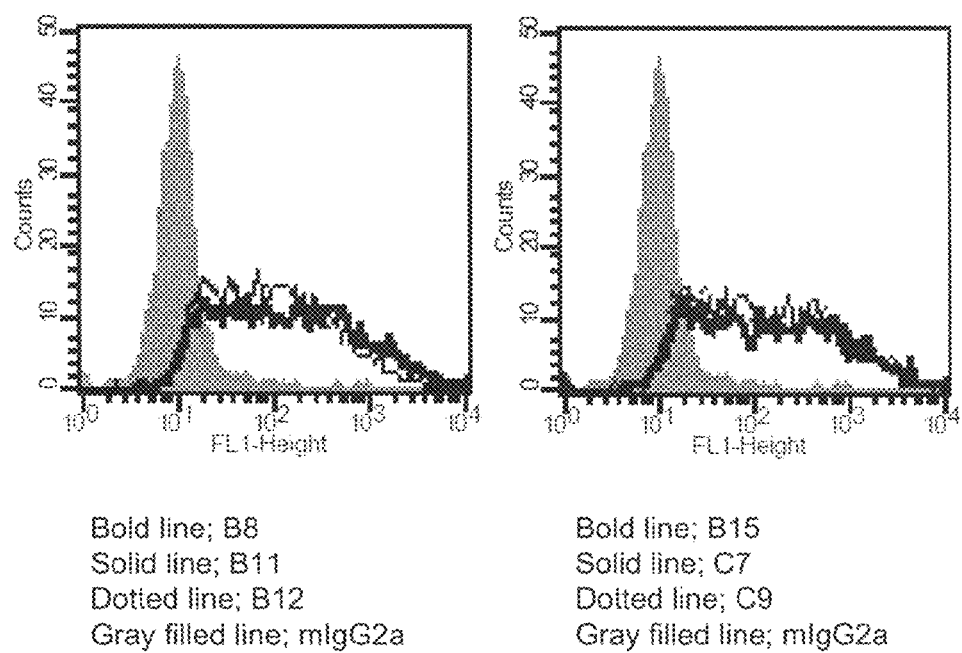
FIG. 9 is a diagram showing results of evaluating the binding of the anti-TM4SF20 antibody to a lung adenocarcinoma cell line A549 by flow cytometry.

Evaluation of TM4SF20 expression in human cancer cell line and antibody-dependent cellular cytotoxicity (ADCC) activity and complement-dependent cytotoxicity (CDC) activity of anti-TM4SF20 antibody 1. Evaluation of TM4SF20 Expression in Human Cancer Cell Line Each anti-TM4SF20 antibody prepared in Example 2 was used to evaluate TM4SF20 expression on the cell membrane of a human cancer cell line by flow cytometry. A primary antibody used was the anti-TM4SF20 antibody (purified antibody) or a negative control antibody (mIgG2a, BD Biosciences Pharmingen). Cells used were a lung adenocarcinoma cell line A549 (JCRB) which exhibited high TM4SF20 mRNA expression in the microarray analysis (Example 1). The flow cytometry was conducted in the same way as in Example 3 except for the primary antibody used at a concentration of 10 μg/mL. As a result, the expression of TM4SF20 was confirmed on the cell membrane of the A549 cells (FIG. 9)

2. Evaluation of ADCC Activity of Anti-TM4SF20 Antibody

The ADCC activity of each anti-TM4SF20 antibody prepared in Example 2 was determined. Target cells used were A549 cells. The A549 cells were adjusted to $2 \times 10^5$ cells/mL with a medium (MEM medium (Invitrogen Corp.) supplemented with 10% FBS) and added at a concentration of 50 μL/well to a flat-bottomed 96-well plate. The cells were attached to the plate by overnight culture at 37° C. in a 5% $CO_2$ incubator. Then, Chromium-51 (GE Healthcare Bio-Sciences Corp.) was further added thereto, and the cells were further cultured for 1 hour. The wells were carefully washed with a medium to prevent the cells from being dissociated from the wells. Then, a medium was added thereto at a concentration of 50 μL/well. Next, the anti-TM4SF20 antibody (purified antibody) or mIgG2a adjusted to 40 μg/mL with a medium was added at a concentration of 50 μL/well. The plate was left standing at room temperature for 15 minutes. Then, effector cells adjusted to $4 \times 10^6$ cells/mL with a medium were added at a concentration of 100 μL/well. The effector cells used were NK-92 cells (ATCC) constantly expressing a chimeric protein comprising the extracellular region of mouse Fcγ receptor III (RefSeq Accession No. NM_010188) and the transmembrane and intracellular regions of human Fcε receptor I-gamma (RefSeq Accession No. NM_004106) (Japanese Patent Application No. 2007-20155 and WO 2008/093688). The cells in the plate were cultured at 37° C. for 4 hours in a 5% $CO_2$ incubator. Then, the culture supernatant (100 μL/well) was collected. The radioactivity (cpm) thereof was measured using a gamma counter (1480 WIZARD 3", Wallac), and the specific chromium release rate (%) was determined according to the following equation:

Specific chromium release rate(%)=$(A-C) \times 100/(B-C)$.

Figure 10:
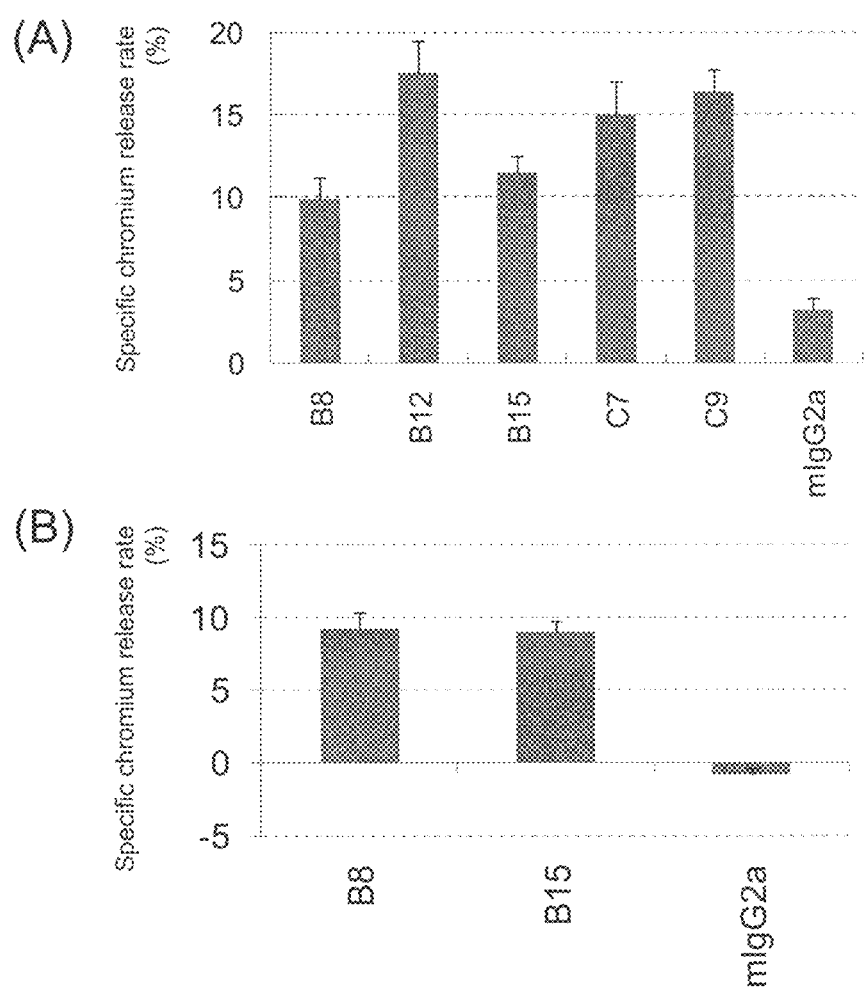
FIG. 10 is a diagram showing results of evaluating the ADCC activity (FIG. 10(A)) and CDC activity (FIG. 10(B)) of the anti-TM4SF20 antibody against a lung adenocarcinoma cell line A549.

In this equation, A represents radioactivity from each well; B represents the mean of radioactivities from wells containing cells dissolved in 1% (final concentration) Nonidet P-40; and C represents the mean of radioactivities from wells supplemented with only the target cells. The experiments were performed in triplicate, and the mean of specific chromium release rates and standard deviation were calculated. The results demonstrated that the anti-TM4SF20 antibodies B8, B12, B15, C7, and C9 have ADCC activity (FIG. 10A).

3. Evaluation of CDC Activity of Anti-TM4SF20 Antibody

The CDC activity of the anti-TM4SF20 antibody was determined in the same way as above. In the CDC activity assay, rabbit serum (Baby Rabbit Complement, CEDARLANE Laboratories Ltd.) diluted to 50% with a medium was added at a concentration of 100 μL/well instead of effector cells, and the cells in the plate were then cultured at 37° C. for 1.5 hours in a 5% $CO_2$ incubator. The results demonstrated that the anti-TM4SF20 antibodies B8 and B15 have CDC activity (FIG. 10B).

Example 7

Analysis of TM4SF20 Expression in Stomach Cancer by Immunohistochemical Staining Since TM4SF20 mRNA expression was confirmed in stomach cancer (Example 1), the expression of TM4SF20 proteins in stomach cancer was analyzed by immunohistochemical staining. From clinical stomach cancer samples, 4% paraformaldehyde-fixed AMeX-embedded paraffin blocks were prepared and cut into 5-μm thin sections. These prepared sections were immunohistochemically stained using Ventana HX Discovery System (Ventana Medical Systems, Inc.) as follows: each section was deparaffinized, then washed, and reacted at 37° C. for 4 minutes with a 3.0% hydrogen peroxide solution (Inhibitor D, Ventana Medical Systems, Inc.) for removal of endogenous peroxidase. After washing, Protein Block (Dako) was added thereto for removal of nonspecific reaction and reacted at room temperature for 30 minutes. After washing, the anti-TM4SF20 antibody (clone B11) was added as a primary antibody at a concentration of 25 μg/mL and reacted at room temperature for 2 hours. After washing, a secondary antibody (Ventana Universal Secondary Antibody, Ventana Medical Systems, Inc.) was added thereto and reacted at room temperature for 30 minutes. After washing, Blocker D (Ventana Medical Systems, Inc.) was reacted at room temperature for 2 minutes for removal of nonspecific reaction, and streptavidin horseradish peroxidase (Ventana Medical Systems, Inc.) was subsequently added thereto and reacted at 37° C. for 16 minutes. After washing, diaminobenzidine (DAB map solution, Ventana Medical Systems, Inc.) and hydrogen peroxide solution (DAB map solution, Ventana Medical Systems, Inc.) were mixed, and the mixture was added thereto and reacted at 42° C. for 8 minutes for coloring of the substrate. Furthermore, the coloring was intensified with Copper sulfate solution (Ventana Medical Systems, Inc.). After washing, the nuclei were stained with hematoxylin, followed by dehydration, penetration, and inclusion.

For adenocarcinoma of the stomach, positive reaction was observed in the cell membrane of 5 out of 9 cases and in the cytoplasm of 7 out thereof. For signet ring cell adenocarcinoma in the stomach, positive reaction was observed in the cell membrane of 3 out of 4 cases and in the cytoplasm of all the cases. The typical stain images are shown in FIG. 11. These results suggest that TM4SF20 is expressed on cell membrane in stomach cancer (adenocarcinoma and signet ring cell adenocarcinoma) and is promising as a target molecule for antibody drugs.

Example 8

Determination of Variable Region Gene Sequence of Anti-TM4SF20 Antibody

The variable regions of each anti-TM4SF20 antibody prepared in Example 2 were sequenced. From $1 \times 10^6$ hybridoma cells producing each antibody, total RNA was purified using Trizol (Invitrogen Corp.). The total RNA (1 μg) was used to PCR-amplify a sequence on antibody H and L chain cDNAs from a position corresponding to each oligonucleotide sequence shown below to the 5'-cDNA end, using SMART RACE cDNA Amplification Kit (Clontech);

a synthetic oligonucleotide MHC-IgG1 (SEQ ID NO:51) complementary to a mouse IgG1 constant region sequence, a synthetic oligonucleotide MHC-G2a (SEQ ID NO: 52) complementary to a mouse IgG2a constant region sequence, a synthetic oligonucleotide MHC-G2b (SEQ ID NO: 53) complementary to a mouse IgG2b constant region sequence, or a synthetic oligonucleotide MLC-kappa (SEQ ID NO: 54) complementary to a mouse κ chain constant region sequence. Each amplification product was cloned into pGEM-T Easy vectors using pGEM-T Easy Vector Systems (Promega Corp.) to determine the cDNA sequence. The variable region sequences of each antibody are summarized in a table below.

TABLE 3

| Antibody | | SEQ ID NO (nucleotide sequence) | SEQ ID NO (amino acid sequence) |
|---|---|---|---|
| B8 | H chain variable region | 55 | 56 |
|  | L chain variable region | 57 | 58 |
| B11 | H chain variable region | 59 | 60 |
|  | L chain variable region | 61 | 62 |
| B12 | H chain variable region | 63 | 64 |
|  | L chain variable region | 65 | 66 |
| B15 | H chain variable region | 67 | 68 |
|  | L chain variable region | 69 | 70 |
| C7 | H chain variable region | 71 | 72 |
|  | L chain variable region | 73 | 74 |
| C9 | H chain variable region | 75 | 76 |
|  | L chain variable region | 77 | 78 |

Moreover, the amino acid sequences of CDRs in these variable regions are summarized in a table below.

TABLE 4

| Antibody | | | SEQ ID NO (amino acid sequence) |
|---|---|---|---|
| B8 | H chain | CDR1 | 79 |
|  |  | CDR2 | 80 |
|  |  | CDR3 | 81 |
|  | L chain | CDR1 | 82 |
|  |  | CDR2 | 83 |
|  |  | CDR3 | 84 |
| B11 | H chain | CDR1 | 85 |
|  |  | CDR2 | 86 |
|  |  | CDR3 | 87 |
|  | L chain | CDR1 | 88 |
|  |  | CDR2 | 89 |
|  |  | CDR3 | 90 |
| B12 | H chain | CDR1 | 91 |
|  |  | CDR2 | 92 |
|  |  | CDR3 | 93 |
|  | L chain | CDR1 | 94 |
|  |  | CDR2 | 95 |
|  |  | CDR3 | 96 |
| B15 | H chain | CDR1 | 97 |
|  |  | CDR2 | 98 |
|  |  | CDR3 | 99 |
|  | L chain | CDR1 | 100 |
|  |  | CDR2 | 101 |
|  |  | CDR3 | 102 |
| C7 | H chain | CDR1 | 103 |
|  |  | CDR2 | 104 |
|  |  | CDR3 | 105 |
|  | L chain | CDR1 | 106 |
|  |  | CDR2 | 107 |
|  |  | CDR3 | 108 |

TABLE 4-continued

| Antibody | | | SEQ ID NO (amino acid sequence) |
|---|---|---|---|
| C9 | H chain | CDR1 | 109 |
|  |  | CDR2 | 110 |
|  |  | CDR3 | 111 |
|  | L chain | CDR1 | 112 |
|  |  | CDR2 | 113 |
|  |  | CDR3 | 114 |

All publications, patents, and patent applications cited herein are incorporated herein by reference with their entirety.

INDUSTRIAL APPLICABILITY

An anti-TM4SF20 antibody of the present invention is useful in the treatment and diagnosis of proliferative diseases including stomach cancer, lung adenocarcinoma, pancreatic cancer, and colon cancer.

FREE TEXT OF SEQUENCE LISTING

[ref2]
SEQ ID NO: 1—primer hSF20FNot2
SEQ ID NO: 2—primer hSF20RXba
SEQ ID NO: 3—primer hSF20FNhe
SEQ ID NO: 4—primer hSF20RNot
SEQ ID NO: 5—plasmid pMCDN2_TM4SF20_ntHA (start codon-stop codon)
SEQ ID NO: 6—plasmid pMCDN2_TM4SF20_ntHA (start codon-stop codon)
SEQ ID NO: 7—primer mSF-F
SEQ ID NO: 8—primer mSF-R
SEQ ID NO: 9—plasmid pGEM-T_mTM4SF20 (start codon-stop codon)
SEQ ID NO: 10—plasmid pGEM-T_mTM4SF20 (start codon-stop codon)
SEQ ID NO: 11—primer mSF20FNhe
SEQ ID NO: 12—primer mSF20RNot
SEQ ID NO: 13—primer h.mTM20FHANot
SEQ ID NO: 14—primer mTM20RHABam
SEQ ID NO: 15—plasmid pCOS2_mTM4SF20_ntHA (start codon-stop codon)
SEQ ID NO: 16—plasmid pCOS2_mTM4SF20_ntHA (start codon-stop codon)
SEQ ID NO: 17—primer hSF20RBamH
SEQ ID NO: 18—plasmid pCOS2_TM4SF20_ctHA (start codon-stop codon)
SEQ ID NO: 19—plasmid pCOS2_TM4SF20_ctHA (start codon-stop codon)
SEQ ID NO: 20—primer hmTM4SF20ver1R1
SEQ ID NO: 21—primer hmTM4SF20ver1F1
SEQ ID NO: 22—primer hTM20RHABam
SEQ ID NO: 23—plasmid pCOS2_chimeraTM4SF20 ver.1_ntHA (start codon-stop codon)
SEQ ID NO: 24—plasmid pCOS2_chimeraTM4SF20 ver.1_ntHA (start codon-stop codon)
SEQ ID NO: 25—primer hmTM4SF20-2-F1
SEQ ID NO: 26—primer hmTM4SF20-2-R1
SEQ ID NO: 27—primer hmTM4SF20-2-R2
SEQ ID NO: 28—primer hmTM4SF20-2-F3
SEQ ID NO: 29—plasmid pCOS2_chimeraTM4SF20 ver.2_ntHA (start codon-stop codon)
SEQ ID NO: 30—plasmid pCOS2_chimeraTM4SF20 ver.2_ntHA (start codon-stop codon)
SEQ ID NO: 31—primer F2
SEQ ID NO: 32—primer R1
SEQ ID NO: 33—primer F3

SEQ ID NO: 34—primer F4
SEQ ID NO: 35—primer F1
SEQ ID NO: 36—primer R2
SEQ ID NO: 37—primer R3
SEQ ID NO: 38—primer R4
SEQ ID NO: 39—construct GST_TM4SF20_N1
SEQ ID NO: 40—construct GST_TM4SF20_N1
SEQ ID NO: 41—construct GST_TM4SF20_N2
SEQ ID NO: 42—construct GST_TM4SF20_N2
SEQ ID NO: 43—construct GST_TM4SF20_N3
SEQ ID NO: 44—construct GST_TM4SF20_N3
SEQ ID NO: 45—construct GST_TM4SF20_C1
SEQ ID NO: 46—construct GST_TM4SF20_C1
SEQ ID NO: 47—construct GST_TM4SF20_C2
SEQ ID NO: 48—construct GST_TM4SF20_C2
SEQ ID NO: 49—construct GST_TM4SF20_C3
SEQ ID NO: 50—construct GST_TM4SF20_C3
SEQ ID NO: 51—synthetic oligonucleotide MHC-IgG1
SEQ ID NO: 52—synthetic oligonucleotide MHC-IgG2a
SEQ ID NO: 53—synthetic oligonucleotide MHC-IgG2b
SEQ ID NO: 54—synthetic oligonucleotide MLC-kappa
SEQ ID NO: 55—B8 H V
SEQ ID NO: 56—B8 H V
SEQ ID NO: 57—B8 L V
SEQ ID NO: 58—B8 L V
SEQ ID NO: 59—B11 H V
SEQ ID NO: 60—B11 H V
SEQ ID NO: 61—B11 L V
SEQ ID NO: 62—B11 L V
SEQ ID NO: 63—B12 H V
SEQ ID NO: 64—B12 H V
SEQ ID NO: 65—B12 L V
SEQ ID NO: 66—B12 L V
SEQ ID NO: 67—B15 H V
SEQ ID NO: 68—B15 H V
SEQ ID NO: 69—B15 L V
SEQ ID NO: 70—B15 L V
SEQ ID NO: 71—C7 H V
SEQ ID NO: 72—C7 H V
SEQ ID NO: 73—C7 L V
SEQ ID NO: 74—C7 L V
SEQ ID NO: 75—C9 H V
SEQ ID NO: 76—C9 H V
SEQ ID NO: 77—C9 L V
SEQ ID NO: 78—C9 L V
SEQ ID NO: 79—B8 H CDR1
SEQ ID NO: 80—B8 H CDR2
SEQ ID NO: 81—B8 H CDR3
SEQ ID NO: 82—B8 L CDR1
SEQ ID NO: 83—B8 L CDR2
SEQ ID NO: 84—B8 L CDR3
SEQ ID NO: 85—B11 H CDR1
SEQ ID NO: 86—B11 H CDR2
SEQ ID NO: 87—B11 H CDR3
SEQ ID NO: 88—B11 L CDR1
SEQ ID NO: 89—B11 L CDR2
SEQ ID NO: 90—B11 L CDR3
SEQ ID NO: 91—B12 H CDR1
SEQ ID NO: 92—B12 H CDR2
SEQ ID NO: 93—B12 H CDR3
SEQ ID NO: 94—B12 L CDR1
SEQ ID NO: 95—B12 L CDR2
SEQ ID NO: 96—B12 L CDR3
SEQ ID NO: 97—B15 H CDR1
SEQ ID NO: 98—B15 H CDR2
SEQ ID NO: 99—B15 H CDR3
SEQ ID NO: 100—B15 L CDR1
SEQ ID NO: 101—B15 L CDR2
SEQ ID NO: 102—B15 L CDR3
SEQ ID NO: 103—C7 H CDR1
SEQ ID NO: 104—C7 H CDR2
SEQ ID NO: 105—C7 H CDR3
SEQ ID NO: 106—C7 L CDR1
SEQ ID NO: 107—C7 L CDR2
SEQ ID NO: 108—C7 L CDR3
SEQ ID NO: 109—C9 H CDR1
SEQ ID NO: 110—C9 H CDR2
SEQ ID NO: 111—C9 H CDR3
SEQ ID NO: 112—C9 L CDR1
SEQ ID NO: 113—C9 L CDR2
SEQ ID NO: 114—C9 L CDR3
SEQ ID NO: 115—human TM4SF20 (GenBank Accession No:NM_024795)
SEQ ID NO: 116—human TM4SF20 (GenBank Accession No:NM_024795)
SEQ ID NO: 117—linker
SEQ ID NO: 118—linker
SEQ ID NO: 119—linker
SEQ ID NO: 120—linker
SEQ ID NO: 121—linker
SEQ ID NO: 122—linker
SEQ ID NO: 123—linker
SEQ ID NO: 124—linker

The invention claimed is:

1. An isolated monoclonal antibody binding to a TM4SF20 protein, wherein the antibody binds to amino acids 168-184 in the amino acid sequence of SEQ ID NO: 116.

2. The antibody according to claim 1, wherein the antibody has cytotoxic activity, wherein the cytotoxic activity is antibody-dependent cellular cytotoxicity (ADCC activity) or complement-dependent cytotoxicity (CDC activity).

3. The antibody according to claim 1, the antibody being selected from the following:

(1) an antibody comprising a heavy chain variable region comprising heavy chain CDR1 having the amino acid sequence represented by SEQ ID NO: 79, heavy chain CDR2 having the amino acid sequence represented by SEQ ID NO: 80, and heavy chain CDR3 having the amino acid sequence represented by SEQ ID NO: 81 and comprising a light chain variable region comprising light chain CDR1 having the amino acid sequence represented by SEQ ID NO: 82, light chain CDR2 having the amino acid sequence represented by SEQ ID NO: 83, and light chain CDR3 having the amino acid sequence represented by SEQ ID NO: 84;

(2) an antibody comprising a heavy chain variable region comprising heavy chain CDR1 having the amino acid sequence represented by SEQ ID NO: 85, heavy chain CDR2 having the amino acid sequence represented by SEQ ID NO: 86, and heavy chain CDR3 having the amino acid sequence represented by SEQ ID NO: 87 and comprising a light chain variable region comprising light chain CDR1 having the amino acid sequence represented by SEQ ID NO: 88, light chain CDR2 having the amino acid sequence represented by SEQ ID NO: 89, and light chain CDR3 having the amino acid sequence represented by SEQ ID NO: 90;

(3) an antibody comprising a heavy chain variable region comprising heavy chain CDR1 having the amino acid sequence represented by SEQ ID NO: 91, heavy chain CDR2 having the amino acid sequence represented by SEQ ID NO: 92, and heavy chain CDR3 having the amino acid sequence represented by SEQ ID NO: 93 and comprising a light chain variable region comprising light chain CDR1 having the amino acid sequence represented by SEQ ID NO: 94, light chain CDR2 having the amino acid sequence represented by SEQ ID NO: 95, and light chain CDR3 having the amino acid sequence represented by SEQ ID NO: 96;

(4) an antibody comprising a heavy chain variable region comprising heavy chain CDR1 having the amino acid sequence represented by SEQ ID NO: 97, heavy chain CDR2 having the amino acid sequence represented by SEQ ID NO: 98, and heavy chain CDR3 having the amino acid sequence represented by SEQ ID NO: 99 and comprising a light chain variable region comprising light chain CDR1 having the amino acid sequence represented by SEQ ID NO: 100, light chain CDR2 having the amino acid sequence represented by SEQ ID NO: 101, and light chain CDR3 having the amino acid sequence represented by SEQ ID NO: 102;

(5) an antibody comprising a heavy chain variable region comprising heavy chain CDR1 having the amino acid sequence represented by SEQ ID NO: 103, heavy chain CDR2 having the amino acid sequence represented by SEQ ID NO: 104, and heavy chain CDR3 having the amino acid sequence represented by SEQ ID NO: 105 and comprising a light chain variable region comprising light chain CDR1 having the amino acid sequence represented by SEQ ID NO: 106, light chain CDR2 having the amino acid sequence represented by SEQ ID NO: 107, and light chain CDR3 having the amino acid sequence represented by SEQ ID NO: 108;

(6) an antibody comprising a heavy chain variable region comprising heavy chain CDR1 having the amino acid sequence represented by SEQ ID NO: 109, heavy chain CDR2 having the amino acid sequence represented by SEQ ID NO: 110, and heavy chain CDR3 having the amino acid sequence represented by SEQ ID NO: 111 and comprising a light chain variable region comprising light chain CDR1 having the amino acid sequence represented by SEQ ID NO: 112, light chain CDR2 having the amino acid sequence represented by SEQ ID NO: 113, and light chain CDR3 having the amino acid sequence represented by SEQ ID NO: 114;

(7) an antibody of (1) to (6), wherein the antibody is a humanized antibody, and has ADCC or CDC activity equivalent to that of the any antibody of (1) to (6); and (8) an antibody binding to the same epitope as that via which any antibody of (1) to (6) binds to the TM4SF20 protein.

4. A pharmaceutical composition comprising an antibody according to claim 1 as an active ingredient.

5. A method for diagnosing cancer, comprising the following steps:
(a) preparing a sample isolated from a test subject; and
(b) detecting the expression level of a TM4SF20 protein in the sample with the isolated monoclonal antibody of claim 1; (c) diagnosing a cancer based on the expression level of the TM4SF20 protein.

6. The diagnosis method according to claim 5, wherein the diagnosis method is intended for the diagnosis of cancer selected from stomach cancer, lung adenocarcinoma, pancreatic cancer, and colon cancer.

7. A diagnostic drug for cancer comprising an antibody according to claim 1.

8. The diagnostic drug according to claim 7, wherein the diagnostic drug is intended for the diagnosis of cancer selected from stomach cancer, lung adenocarcinoma, pancreatic cancer, and colon cancer.

* * * * *

```
                         SEQUENCE LISTING

<160> NUMBER OF SEQ ID NOS: 124

<210> SEQ ID NO 1
<211> LENGTH: 35
<212> TYPE: DNA
<213> ORGANISM: Artificial Sequence
<220> FEATURE:
<223> OTHER INFORMATION: primer hSF20FNot2

<400> SEQUENCE: 1
attgcggccg ccaccatgac ctgctgcgaa ggatg                              35

<210> SEQ ID NO 2
<211> LENGTH: 30
<212> TYPE: DNA
<213> ORGANISM: Artificial Sequence
```

<220> FEATURE:
<223> OTHER INFORMATION: primer hSF20RXba

<400> SEQUENCE: 2
aatctagact acacaatttg acttcttcgc                                           30

<210> SEQ ID NO 3
<211> LENGTH: 29
<212> TYPE: DNA
<213> ORGANISM: Artificial Sequence
<220> FEATURE:
<223> OTHER INFORMATION: primer hSF20FNhe

<400> SEQUENCE: 3
aatgctagca cctgctgcga aggatggac                                            29

<210> SEQ ID NO 4
<211> LENGTH: 30
<212> TYPE: DNA
<213> ORGANISM: Artificial Sequence
<220> FEATURE:
<223> OTHER INFORMATION: primer hSF20RNot

<400> SEQUENCE: 4
tatgcggccg ctcacaattt gacttcttcg                                           30

<210> SEQ ID NO 5
<211> LENGTH: 729
<212> TYPE: DNA
<213> ORGANISM: Artificial Sequence
<220> FEATURE:
<223> OTHER INFORMATION: plasmid pMCDN2_TM4SF20_ntHA(initiation codon -
      stop codon)

<400> SEQUENCE: 5
atgtacccat acgatgttcc agattacgct agcacctgct gcgaaggatg gacatcctgc          60
aatggattca gcctgctggt tctactgctg ttaggagtag ttctcaatgc gatacctcta         120
attgtcagct tagttgagga agaccaattt tctcaaaaacc ccatctcttg ctttgagtgg        180
tggttcccag gaattatagg agcaggtctg atggccattc cagcaacaac aatgtccttg         240
acagcaagaa aaagagcgtg ctgcaacaac agaactggaa tgtttctttc atcactttc         300 agtgtgatca cagtcattgg tgctctgtat gcatgctga tatccatcca ggctctctta         360
aaaggtcctc tcatgtgtaa ttctccaagc aacagtaatg ccaattgtga attttcattg        420
aaaaacatca gtgacattca tccagaatcc ttcaacttgc agtggttttt caatgactct         480
tgtgcacctc ctactggttt caataaaccc accagtaacg acaccatggc gagtggctgg         540
agagcatcta gtttccactt cgattctgaa gaaaacaaac ataggcttat ccacttctca         600 gtattttag gtctattgct tgttggaatt ctggaggtcc tgtttgggct cagtcagata         660
gtcatcggtt ccttggctg tctgtgtgga gtctctaagc gaagaagtca aattgtgagc         720
ggccgctga                                                                 729

<210> SEQ ID NO 6
<211> LENGTH: 242
<212> TYPE: PRT
<213> ORGANISM: Artificial Sequence
<220> FEATURE:
<223> OTHER INFORMATION: plasmid pMCDN2_TM4SF20_ntHA(initiation codon -
      stop codon)

<400> SEQUENCE: 6

Met Tyr Pro Tyr Asp Val Pro Asp Tyr Ala Ser Thr Cys Cys Glu Gly
1               5                   10                  15

Trp Thr Ser Cys Asn Gly Phe Ser Leu Leu Val Leu Leu Leu Leu Gly
            20                  25                  30

Val Val Leu Asn Ala Ile Pro Leu Ile Val Ser Leu Val Glu Glu Asp
        35                  40                  45

Gln Phe Ser Gln Asn Pro Ile Ser Cys Phe Glu Trp Trp Phe Pro Gly
    50                  55                  60

Ile Ile Gly Ala Gly Leu Met Ala Ile Pro Ala Thr Thr Met Ser Leu
65              70                  75                  80

Thr Ala Arg Lys Arg Ala Cys Cys Asn Asn Arg Thr Gly Met Phe Leu
                85                  90                  95

Ser Ser Leu Phe Ser Val Ile Thr Val Ile Gly Ala Leu Tyr Cys Met
            100                 105                 110

Leu Ile Ser Ile Gln Ala Leu Leu Lys Gly Pro Leu Met Cys Asn Ser
            115                 120                 125

Pro Ser Asn Ser Asn Ala Asn Cys Glu Phe Ser Leu Lys Asn Ile Ser
    130                 135                 140

Asp Ile His Pro Glu Ser Phe Asn Leu Gln Trp Phe Phe Asn Asp Ser
145                 150                 155                 160

Cys Ala Pro Pro Thr Gly Phe Asn Lys Pro Thr Ser Asn Asp Thr Met
                165                 170                 175

Ala Ser Gly Trp Arg Ala Ser Ser Phe His Phe Asp Ser Glu Glu Asn
            180                 185                 190

Lys His Arg Leu Ile His Phe Ser Val Phe Leu Gly Leu Leu Leu Val
        195                 200                 205

Gly Ile Leu Glu Val Leu Phe Gly Leu Ser Gln Ile Val Ile Gly Phe
    210                 215                 220

Leu Gly Cys Leu Cys Gly Val Ser Lys Arg Arg Ser Gln Ile Val Ser
225                 230                 235                 240

Gly Arg

<210> SEQ ID NO 7
<211> LENGTH: 20
<212> TYPE: DNA
<213> ORGANISM: Artificial Sequence
<220> FEATURE:
<223> OTHER INFORMATION: primer mSF-F

<400> SEQUENCE: 7
atgacgtgct gtgaagggtg                                           20

<210> SEQ ID NO 8
<211> LENGTH: 20
<212> TYPE: DNA
<213> ORGANISM: Artificial Sequence
<220> FEATURE:
<223> OTHER INFORMATION: primer mSF-R

<400> SEQUENCE: 8
ttatacaatt tgactccgtc                                           20

<210> SEQ ID NO 9
<211> LENGTH: 681
<212> TYPE: DNA
<213> ORGANISM: Artificial Sequence

```
<220> FEATURE:
<223> OTHER INFORMATION: plasmid pGEM-T_mTM4SF20(initiation codon - stop
      codon)

<400> SEQUENCE: 9
atgacgtgct gtgaagggtg gacatcctgc aatggcttca gcctgctcat tctgatcctg      60
ctaggagtgg ttatcaattg tataccctg ggaatcagct tagtggaggc agactcgact      120
tctcaaaacc ccatctcctg ctatgagtgg tggtttccag gaattatagg agcaggtctg      180
atggccatcc cggcaacaac aatgtccttg gcagcaagaa aaagagcgtg ctgcaacaat      240
aagactggga tgtttctttc atcactcttc agtatgatca cagtcgttgg tgctgtgtat      300
tgcatgttgg tatcactcca ggctctcttg gaaggacctc taatttgtaa tactcaggcc      360
aacagtactg tcacttgtga attttcattg aaaaacttaa gtaactttga tcctgaatcc      420
ttcaatctgc tgtggttctt caatggcact tgtgtttctc ctactgattt taaaaacccc      480
accatcaata acatggtcag taactggaaa atacccaact ccaactctga gaaagacaga      540
cacaggattt tccacttctc agtatttatg agtctcctgc ttgttggaat cctggagctc      600
ctgtttgggc tcagtcagat actcattggt tccttggct gtctgtgtgg cgtctctcag      660
cgacggagtc aaattgtata a                                                681

<210> SEQ ID NO 10
<211> LENGTH: 226
<212> TYPE: PRT
<213> ORGANISM: Artificial Sequence
<220> FEATURE:
<223> OTHER INFORMATION: plasmid pGEM-T_mTM4SF20(initiation codon - stop
      codon)

<400> SEQUENCE: 10

Met Thr Cys Cys Glu Gly Trp Thr Ser Cys Asn Gly Phe Ser Leu Leu
1               5                   10                  15

Ile Leu Ile Leu Leu Gly Val Val Ile Asn Cys Ile Pro Leu Gly Ile
            20                  25                  30

Ser Leu Val Glu Ala Asp Ser Thr Ser Gln Asn Pro Ile Ser Cys Tyr
        35                  40                  45

Glu Trp Trp Phe Pro Gly Ile Ile Gly Ala Gly Leu Met Ala Ile Pro
    50                  55                  60

Ala Thr Thr Met Ser Leu Ala Ala Arg Lys Arg Ala Cys Cys Asn Asn
65                  70                  75                  80

Lys Thr Gly Met Phe Leu Ser Ser Leu Phe Ser Met Ile Thr Val Val
                85                  90                  95

Gly Ala Val Tyr Cys Met Leu Val Ser Leu Gln Ala Leu Leu Glu Gly
            100                 105                 110

Pro Leu Ile Cys Asn Thr Gln Ala Asn Ser Thr Val Thr Cys Glu Phe
        115                 120                 125

Ser Leu Lys Asn Leu Ser Asn Phe Asp Pro Glu Ser Phe Asn Leu Leu
    130                 135                 140

Trp Phe Phe Asn Gly Thr Cys Val Ser Pro Thr Asp Phe Lys Asn Pro
145                 150                 155                 160

Thr Ile Asn Asn Met Val Ser Asn Trp Lys Ile Pro Asn Ser Asn Ser
                165                 170                 175

Glu Glu Asp Arg His Arg Ile Phe His Phe Ser Val Phe Met Ser Leu
            180                 185                 190

Leu Leu Val Gly Ile Leu Glu Leu Leu Phe Gly Leu Ser Gln Ile Leu
        195                 200                 205
```

```
Ile Gly Phe Leu Gly Cys Leu Cys Gly Val Ser Gln Arg Arg Ser Gln
    210                 215                 220

Ile Val
225

<210> SEQ ID NO 11
<211> LENGTH: 23
<212> TYPE: DNA
<213> ORGANISM: Artificial Sequence
<220> FEATURE:
<223> OTHER INFORMATION: primer mSF20FNhe

<400> SEQUENCE: 11
aagcggccgc ttacaatttg act                                          23

<210> SEQ ID NO 12
<211> LENGTH: 22
<212> TYPE: DNA
<213> ORGANISM: Artificial Sequence
<220> FEATURE:
<223> OTHER INFORMATION: primer mSF20RNot

<400> SEQUENCE: 12
aagcggccgc caccatgtac cc                                           22

<210> SEQ ID NO 13
<211> LENGTH: 22
<212> TYPE: DNA
<213> ORGANISM: Artificial Sequence
<220> FEATURE:
<223> OTHER INFORMATION: primer h.mTM20FHANot

<400> SEQUENCE: 13
aagcggccgc caccatgtac cc                                           22

<210> SEQ ID NO 14
<211> LENGTH: 17
<212> TYPE: DNA
<213> ORGANISM: Artificial Sequence
<220> FEATURE:
<223> OTHER INFORMATION: primer mTM20RHABam

<400> SEQUENCE: 14
ttggatcctc atacaat                                                 17

<210> SEQ ID NO 15
<211> LENGTH: 717
<212> TYPE: DNA
<213> ORGANISM: Artificial Sequence
<220> FEATURE:
<223> OTHER INFORMATION: plasmid pCOS2_mTM4SF20_ntHA(initiation codon -
      stop codon)

<400> SEQUENCE: 15
atgtacccat acgatgttcc agattacgct agcacgtgct gtgaagggtg gacatcctgc    60
aatggcttca gcctgctcat tctgatcctg ctaggagtgg ttatcaattg tataccctg    120 ggaatcagct tagtggaggc agactcgact tctcaaaacc ccatctcctg ctatgagtgg   180
tggtttccag gaattatagg agcaggtctg atggccatcc cggcaacaac aatgtccttg   240
gcagcaagaa aaagagcgtg ctgcaacaat aagactggga tgtttctttc atcactcttc   300
agtatgatca cagtcgttgg tgctgtgtat tgcatgttgg tatcactcca ggctctcttg   360
gaaggacctc taatttgtaa tactcaggcc aacagtactg tcacttgtga attttcattg   420
```

```
aaaaacttaa gtaactttga tcctgaatcc ttcaatctgc tgtggttctt caatggcact    480
tgtgtttctc ctactgattt taaaaacccc accatcaata acatggtcag taactggaaa    540
atacccaact ccaactctga agaagacaga cacaggattt tccacttctc agtatttatg    600
agtctcctgc ttgttggaat cctggagctc ctgtttgggc tcagtcagat actcattggt    660
ttccttggct gtctgtgtgg cgtctctcag cgacggagtc aaattgtagg atcctag     717
```

<210> SEQ ID NO 16
<211> LENGTH: 238
<212> TYPE: PRT
<213> ORGANISM: Artificial Sequence
<220> FEATURE:
<223> OTHER INFORMATION: plasmid pCOS2_mTM4SF20_ntHA(initiation codon - stop codon)

<400> SEQUENCE: 16

```
Met Tyr Pro Tyr Asp Val Pro Asp Tyr Ala Ser Thr Cys Cys Glu Gly
1               5                   10                  15

Trp Thr Ser Cys Asn Gly Phe Ser Leu Leu Ile Leu Ile Leu Leu Gly
            20                  25                  30

Val Val Ile Asn Cys Ile Pro Leu Gly Ile Ser Leu Val Glu Ala Asp
        35                  40                  45

Ser Thr Ser Gln Asn Pro Ile Ser Cys Tyr Glu Trp Trp Phe Pro Gly
    50                  55                  60

Ile Ile Gly Ala Gly Leu Met Ala Ile Pro Ala Thr Thr Met Ser Leu
65                  70                  75                  80

Ala Ala Arg Lys Arg Ala Cys Cys Asn Asn Lys Thr Gly Met Phe Leu
                85                  90                  95

Ser Ser Leu Phe Ser Met Ile Thr Val Val Gly Ala Val Tyr Cys Met
            100                 105                 110

Leu Val Ser Leu Gln Ala Leu Leu Glu Gly Pro Leu Ile Cys Asn Thr
        115                 120                 125

Gln Ala Asn Ser Thr Val Thr Cys Glu Phe Ser Leu Lys Asn Leu Ser
    130                 135                 140

Asn Phe Asp Pro Glu Ser Phe Asn Leu Leu Trp Phe Phe Asn Gly Thr
145                 150                 155                 160

Cys Val Ser Pro Thr Asp Phe Lys Asn Pro Thr Ile Asn Asn Met Val
                165                 170                 175

Ser Asn Trp Lys Ile Pro Asn Ser Asn Ser Glu Glu Asp Arg His Arg
            180                 185                 190

Ile Phe His Phe Ser Val Phe Met Ser Leu Leu Leu Val Gly Ile Leu
        195                 200                 205

Glu Leu Leu Phe Gly Leu Ser Gln Ile Leu Ile Gly Phe Leu Gly Cys
    210                 215                 220

Leu Cys Gly Val Ser Gln Arg Arg Ser Gln Ile Val Gly Ser
225                 230                 235
```

<210> SEQ ID NO 17
<211> LENGTH: 27
<212> TYPE: DNA
<213> ORGANISM: Artificial Sequence
<220> FEATURE:
<223> OTHER INFORMATION: primer hSF20RBamH

<400> SEQUENCE: 17

```
ttggatccca caatttgact tcttcgc                                       27
```

<210> SEQ ID NO 18
<211> LENGTH: 723
<212> TYPE: DNA
<213> ORGANISM: Artificial Sequence
<220> FEATURE:
<223> OTHER INFORMATION: plasmid pCOS2_TM4SF20_ctHA(initiation codon - stop codon)

<400> SEQUENCE: 18

```
atgacctgct gcgaaggatg gacatcctgc aatggattca gcctgctggt tctactgctg      60
ttaggagtag ttctcaatgc gatacctcta attgtcagct tagttgagga agaccaattt     120
tctcaaaacc ccatctcttg ctttgagtgg tggttcccag gaattatagg agcaggtctg     180
atggccattc cagcaacaac aatgtccttg acagcaagaa aaagagcgtg ctgcaacaac     240
agaactggaa tgtttctttc atcactttc agtgtgatca cagtcattgg tgctctgtat     300
tgcatgctga tatccatcca ggctctctta aaaggtcctc tcatgtgtaa ttctccaagc     360
aacagtaatg ccaattgtga attttcattg aaaaacatca gtgacattca tccagaatcc     420
ttcaacttgc agtggttttt caatgactct tgtgcacctc ctactggttt caataaaccc     480
accagtaacg acaccatggc gagtggctgg agagcatcta gtttccactt cgattctgaa     540
gaaaacaaac ataggcttat ccacttctca gtattttag gtctattgct tgttggaatt     600
ctggaggtcc tgtttgggct cagtcagata gtcatcggtt ccttggctg tctgtgtgga     660
gtctctaagc gaagaagtca aattgtggga tcctacccat acgatgttcc agattacgct     720
tga                                                                    723
```

<210> SEQ ID NO 19
<211> LENGTH: 240
<212> TYPE: PRT
<213> ORGANISM: Artificial Sequence
<220> FEATURE:
<223> OTHER INFORMATION: plasmid pCOS2_TM4SF20_ctHA(initiation codon - stop codon)

<400> SEQUENCE: 19

```
Met Thr Cys Cys Glu Gly Trp Thr Ser Cys Asn Gly Phe Ser Leu Leu
1               5                   10                  15

Val Leu Leu Leu Gly Val Val Leu Asn Ala Ile Pro Leu Ile Val
            20                  25                  30

Ser Leu Val Glu Glu Asp Gln Phe Ser Gln Asn Pro Ile Ser Cys Phe
        35                  40                  45

Glu Trp Trp Phe Pro Gly Ile Ile Gly Ala Gly Leu Met Ala Ile Pro
    50                  55                  60

Ala Thr Thr Met Ser Leu Thr Ala Arg Lys Arg Ala Cys Cys Asn Asn
65                  70                  75                  80

Arg Thr Gly Met Phe Leu Ser Ser Leu Phe Ser Val Ile Thr Val Ile
                85                  90                  95

Gly Ala Leu Tyr Cys Met Leu Ile Ser Ile Gln Ala Leu Leu Lys Gly
            100                 105                 110

Pro Leu Met Cys Asn Ser Pro Ser Asn Ser Asn Ala Asn Cys Glu Phe
        115                 120                 125

Ser Leu Lys Asn Ile Ser Asp Ile His Pro Glu Ser Phe Asn Leu Gln
    130                 135                 140

Trp Phe Phe Asn Asp Ser Cys Ala Pro Pro Thr Gly Phe Asn Lys Pro
145                 150                 155                 160

Thr Ser Asn Asp Thr Met Ala Ser Gly Trp Arg Ala Ser Ser Phe His
                165                 170                 175
```

```
Phe Asp Ser Glu Glu Asn Lys His Arg Leu Ile His Phe Ser Val Phe
                180                 185                 190

Leu Gly Leu Leu Leu Val Gly Ile Leu Glu Val Leu Phe Gly Leu Ser
            195                 200                 205

Gln Ile Val Ile Gly Phe Leu Gly Cys Leu Cys Gly Val Ser Lys Arg
210                 215                 220

Arg Ser Gln Ile Val Gly Ser Tyr Pro Tyr Asp Val Pro Asp Tyr Ala
225                 230                 235                 240
```

<210> SEQ ID NO 20
<211> LENGTH: 52
<212> TYPE: DNA
<213> ORGANISM: Artificial Sequence
<220> FEATURE:
<223> OTHER INFORMATION: primer hmTM4SF20ver1R1

<400> SEQUENCE: 20

```
ggttttgaga gtcgagtct gcctcaacta agctgacaat tagaggtatc gc        52
```

<210> SEQ ID NO 21
<211> LENGTH: 51
<212> TYPE: DNA
<213> ORGANISM: Artificial Sequence
<220> FEATURE:
<223> OTHER INFORMATION: primer hmTM4SF20ver1F1

<400> SEQUENCE: 21

```
gaggcagact cgacttctca aaccccatc tcttgctttg agtggtggtt c         51
```

<210> SEQ ID NO 22
<211> LENGTH: 20
<212> TYPE: DNA
<213> ORGANISM: Artificial Sequence
<220> FEATURE:
<223> OTHER INFORMATION: primer hTM20RHABam

<400> SEQUENCE: 22

```
ttggatcctc acacaatttg                                           20
```

<210> SEQ ID NO 23
<211> LENGTH: 720
<212> TYPE: DNA
<213> ORGANISM: Artificial Sequence
<220> FEATURE:
<223> OTHER INFORMATION: plasmid pCOS2_chimeraTM4SF20 ver.1_ntHA
      (initiation codon - stop codon)

<400> SEQUENCE: 23

```
atgtacccat acgatgttcc agattacgct agcacctgct gcgaaggatg gacatcctgc    60
aatggattca gcctgctggt tctactgctg ttaggagtag ttctcaatgc gatacctcta   120
attgtcagct tagttgaggc agactcgact tctcaaaacc ccatctcttg ctttgagtgg   180
tggttcccag gaattatagg agcaggtctg atggccattc agcaacaac aatgtccttg    240 acagcaagaa aaagagcgtg ctgcaacaac agaactggaa tgtttctttc atcactttc    300 agtgtgatca cagtcattgg tgctctgtat gcatgctga tatccatcca ggctctctta    360
aaaggtcctc tcatgtgtaa ttctccaagc aacagtaatg ccaattgtga attttcattg    420
aaaaacatca gtgacattca tccagaatcc ttcaacttgc agtggttttt caatgactct   480
tgtgcacctc ctactggttt caataaaccc accagtaacg acaccatggc gagtggctgg   540
agagcatcta gtttccactt cgattctgaa gaaaacaaac ataggcttat ccacttctca   600
```

```
gtattttag gtctattgct tgttggaatt ctggaggtcc tgtttgggct cagtcagata    660
gtcatcggtt tccttggctg tctgtgtgga gtctctaagc gaagaagtca aattgtgtga   720
```

<210> SEQ ID NO 24
<211> LENGTH: 239
<212> TYPE: PRT
<213> ORGANISM: Artificial Sequence
<220> FEATURE:
<223> OTHER INFORMATION: plasmid pCOS2_chimeraTM4SF20 ver.1_ntHA
      (initiation codon - stop codon)

<400> SEQUENCE: 24

Met Tyr Pro Tyr Asp Val Pro Asp Tyr Ala Ser Thr Cys Cys Glu Gly
1               5                   10                  15

Trp Thr Ser Cys Asn Gly Phe Ser Leu Leu Val Leu Leu Leu Leu Gly
            20                  25                  30

Val Val Leu Asn Ala Ile Pro Leu Ile Val Ser Leu Val Glu Ala Asp
        35                  40                  45

Ser Thr Ser Gln Asn Pro Ile Ser Cys Phe Glu Trp Trp Phe Pro Gly
    50                  55                  60

Ile Ile Gly Ala Gly Leu Met Ala Ile Pro Ala Thr Thr Met Ser Leu
65                  70                  75                  80

Thr Ala Arg Lys Arg Ala Cys Cys Asn Asn Arg Thr Gly Met Phe Leu
                85                  90                  95

Ser Ser Leu Phe Ser Val Ile Thr Val Ile Gly Ala Leu Tyr Cys Met
            100                 105                 110

Leu Ile Ser Ile Gln Ala Leu Leu Lys Gly Pro Leu Met Cys Asn Ser
        115                 120                 125

Pro Ser Asn Ser Asn Ala Asn Cys Glu Phe Ser Leu Lys Asn Ile Ser
    130                 135                 140

Asp Ile His Pro Glu Ser Phe Asn Leu Gln Trp Phe Phe Asn Asp Ser
145                 150                 155                 160

Cys Ala Pro Pro Thr Gly Phe Asn Lys Pro Thr Ser Asn Asp Thr Met
                165                 170                 175

Ala Ser Gly Trp Arg Ala Ser Ser Phe His Phe Asp Ser Glu Glu Asn
            180                 185                 190

Lys His Arg Leu Ile His Phe Ser Val Phe Leu Gly Leu Leu Leu Val
        195                 200                 205

Gly Ile Leu Glu Val Leu Phe Gly Leu Ser Gln Ile Val Ile Gly Phe
    210                 215                 220

Leu Gly Cys Leu Cys Gly Val Ser Lys Arg Arg Ser Gln Ile Val
225                 230                 235

<210> SEQ ID NO 25
<211> LENGTH: 33
<212> TYPE: DNA
<213> ORGANISM: Artificial Sequence
<220> FEATURE:
<223> OTHER INFORMATION: primer hmTM4SF20-2-F1

<400> SEQUENCE: 25
tattgcatgc tgatatcact ccaggctctc ttg                                33

<210> SEQ ID NO 26
<211> LENGTH: 24
<212> TYPE: DNA
<213> ORGANISM: Artificial Sequence
<220> FEATURE:

<223> OTHER INFORMATION: primer hmTM4SF20-2-R1

<400> SEQUENCE: 26
gaagtggata agcctgtgtc tgtc                                              24

<210> SEQ ID NO 27
<211> LENGTH: 21
<212> TYPE: DNA
<213> ORGANISM: Artificial Sequence
<220> FEATURE:
<223> OTHER INFORMATION: primer hmTM4SF20-2-R2

<400> SEQUENCE: 27
agcctggagt gatatcagca t                                                 21

<210> SEQ ID NO 28
<211> LENGTH: 21
<212> TYPE: DNA
<213> ORGANISM: Artificial Sequence
<220> FEATURE:
<223> OTHER INFORMATION: primer hmTM4SF20-2-F3

<400> SEQUENCE: 28
gacagacaca ggcttatcca c                                                 21

<210> SEQ ID NO 29
<211> LENGTH: 711
<212> TYPE: DNA
<213> ORGANISM: Artificial Sequence
<220> FEATURE:
<223> OTHER INFORMATION: plasmid pCOS2_chimeraTM4SF20 ver.2_ntHA
      (initiation codon - stop codon)

<400> SEQUENCE: 29
atgtacccat acgatgttcc agattacgct agcacctgct gcgaaggatg gacatcctgc       60
aatggattca gcctgctggt tctactgctg ttaggagtag ttctcaatgc gatacctcta      120
attgtcagct tagttgagga agaccaattt tctcaaaacc ccatctcttg ctttgagtgg      180
tggttcccag gaattatagg agcaggtctg atggccattc agcaacaac aatgtccttg       240 acagcaagaa aaagagcgtg ctgcaacaac agaactggaa tgtttctttc atcactttc      300 agtgtgatca cagtcattgg tgctctgtat tgcatgctga tatcactcca ggctctcttg      360
gaaggacctc taatttgtaa tactcaggcc aacagtactg tcacttgtga attttcattg      420
aaaaacttaa gtaactttga tcctgaatcc ttcaatctgc tgtggttctt caatggcact      480
tgtgtttctc ctactgattt taaaaacccc accatcaata acatggtcag taactggaaa      540
atacccaact ccaactctga agaagacaga cacaggctta tccacttctc agtattttta      600
ggtctattgc ttgttggaat tctggaggtc ctgtttgggc tcagtcagat agtcatcggt      660
ttccttggct gtctgtgtgg agtctctaag cgaagaagtc aaattgtgtg a              711

<210> SEQ ID NO 30
<211> LENGTH: 236
<212> TYPE: PRT
<213> ORGANISM: Artificial Sequence
<220> FEATURE:
<223> OTHER INFORMATION: plasmid pCOS2_chimeraTM4SF20 ver.2_ntHA
      (initiation codon - stop codon)

<400> SEQUENCE: 30

Met Tyr Pro Tyr Asp Val Pro Asp Tyr Ala Ser Thr Cys Cys Glu Gly
1               5                   10                  15

```
Trp Thr Ser Cys Asn Gly Phe Ser Leu Leu Val Leu Leu Leu Gly
             20                  25                  30

Val Val Leu Asn Ala Ile Pro Leu Ile Val Ser Leu Val Glu Glu Asp
         35                  40                  45

Gln Phe Ser Gln Asn Pro Ile Ser Cys Phe Glu Trp Trp Phe Pro Gly
     50                  55                  60

Ile Ile Gly Ala Gly Leu Met Ala Ile Pro Ala Thr Thr Met Ser Leu
 65                  70                  75                  80

Thr Ala Arg Lys Arg Ala Cys Cys Asn Asn Arg Thr Gly Met Phe Leu
             85                  90                  95

Ser Ser Leu Phe Ser Val Ile Thr Val Ile Gly Ala Leu Tyr Cys Met
            100                 105                 110

Leu Ile Ser Leu Gln Ala Leu Leu Glu Gly Pro Leu Ile Cys Asn Thr
        115                 120                 125

Gln Ala Asn Ser Thr Val Thr Cys Glu Phe Ser Leu Lys Asn Leu Ser
    130                 135                 140

Asn Phe Asp Pro Glu Ser Phe Asn Leu Leu Trp Phe Phe Asn Gly Thr
145                 150                 155                 160

Cys Val Ser Pro Thr Asp Phe Lys Asn Pro Thr Ile Asn Asn Met Val
                165                 170                 175

Ser Asn Trp Lys Ile Pro Asn Ser Asn Ser Glu Glu Asp Arg His Arg
            180                 185                 190

Leu Ile His Phe Ser Val Phe Leu Gly Leu Leu Leu Val Gly Ile Leu
        195                 200                 205

Glu Val Leu Phe Gly Leu Ser Gln Ile Val Ile Gly Phe Leu Gly Cys
    210                 215                 220

Leu Cys Gly Val Ser Lys Arg Arg Ser Gln Ile Val
225                 230                 235

<210> SEQ ID NO 31
<211> LENGTH: 35
<212> TYPE: DNA
<213> ORGANISM: Artificial Sequence
<220> FEATURE:
<223> OTHER INFORMATION: primer F2

<400> SEQUENCE: 31
attggatcca attctccaag caacagtaat gccaa                          35

<210> SEQ ID NO 32
<211> LENGTH: 56
<212> TYPE: DNA
<213> ORGANISM: Artificial Sequence
<220> FEATURE:
<223> OTHER INFORMATION: primer R1

<400> SEQUENCE: 32
ttagcggccg cttatcaatg atgatgatga tgatgaattc caacaagcaa tagacc   56

<210> SEQ ID NO 33
<211> LENGTH: 36
<212> TYPE: DNA
<213> ORGANISM: Artificial Sequence
<220> FEATURE:
<223> OTHER INFORMATION: primer F3

<400> SEQUENCE: 33
attggatcca gtgacattca tccagaatcc ttcaac                         36
```

```
<210> SEQ ID NO 34
<211> LENGTH: 37
<212> TYPE: DNA
<213> ORGANISM: Artificial Sequence
<220> FEATURE:
<223> OTHER INFORMATION: primer F4

<400> SEQUENCE: 34
attggatcct gtgcacctcc tactggtttc aataaac                              37

<210> SEQ ID NO 35
<211> LENGTH: 28
<212> TYPE: DNA
<213> ORGANISM: Artificial Sequence
<220> FEATURE:
<223> OTHER INFORMATION: primer F1

<400> SEQUENCE: 35
attggatcct gcatgctgat atccatcc                                       28

<210> SEQ ID NO 36
<211> LENGTH: 63
<212> TYPE: DNA
<213> ORGANISM: Artificial Sequence
<220> FEATURE:
<223> OTHER INFORMATION: primer R2

<400> SEQUENCE: 36
ttagcggccg cttatcaatg atgatgatga tgatgatgtt tgttttcttc agaatcgaag    60
tgg                                                                  63

<210> SEQ ID NO 37
<211> LENGTH: 56
<212> TYPE: DNA
<213> ORGANISM: Artificial Sequence
<220> FEATURE:
<223> OTHER INFORMATION: primer R3

<400> SEQUENCE: 37
ttagcggccg cttatcaatg atgatgatga tgatgcgcca tggtgtcgtt actggt        56

<210> SEQ ID NO 38
<211> LENGTH: 62
<212> TYPE: DNA
<213> ORGANISM: Artificial Sequence
<220> FEATURE:
<223> OTHER INFORMATION: primer R4

<400> SEQUENCE: 38
ttagcggccg cttatcaatg atgatgatga tgatgagagt cattgaaaaa ccactgcaag    60
tt                                                                   62

<210> SEQ ID NO 39
<211> LENGTH: 279
<212> TYPE: DNA
<213> ORGANISM: Artificial Sequence
<220> FEATURE:
<223> OTHER INFORMATION: construct GST_TM4SF20_N1

<400> SEQUENCE: 39
ggatccaatt ctccaagcaa cagtaatgcc aattgtgaat tttcattgaa aaacatcagt    60
gacattcatc cagaatcctt caacttgcag tggttttttca atgactcttg tgcacctcct  120
actggtttca ataaacccac cagtaacgac accatggcga gtggctggag agcatctagt  180
```

```
ttccacttcg attctgaaga aaacaaacat aggcttatcc acttctcagt attttaggt    240 ctattgcttg ttggaattca tcatcatcat catcattga                          279
```

```
<210> SEQ ID NO 40
<211> LENGTH: 92
<212> TYPE: PRT
<213> ORGANISM: Artificial Sequence
<220> FEATURE:
<223> OTHER INFORMATION: construct GST_TM4SF20_N1

<400> SEQUENCE: 40
```

Gly Ser Asn Ser Pro Ser Asn Ser Asn Ala Asn Cys Glu Phe Ser Leu
1               5                   10                  15

Lys Asn Ile Ser Asp Ile His Pro Glu Ser Phe Asn Leu Gln Trp Phe
            20                  25                  30

Phe Asn Asp Ser Cys Ala Pro Pro Thr Gly Phe Asn Lys Pro Thr Ser
        35                  40                  45

Asn Asp Thr Met Ala Ser Gly Trp Arg Ala Ser Ser Phe His Phe Asp
    50                  55                  60

Ser Glu Glu Asn Lys His Arg Leu Ile His Phe Ser Val Phe Leu Gly
65                  70                  75                  80

Leu Leu Leu Val Gly Ile His His His His His His
                85                  90

```
<210> SEQ ID NO 41
<211> LENGTH: 228
<212> TYPE: DNA
<213> ORGANISM: Artificial Sequence
<220> FEATURE:
<223> OTHER INFORMATION: construct GST_TM4SF20_N2

<400> SEQUENCE: 41
ggatccagtg acattcatcc agaatccttc aacttgcagt ggttttcaa tgactcttgt     60 gcacctccta ctggttttca taaacccacc agtaacgaca ccatggcgag tggctggaga   120
gcatctagtt tccacttcga ttctgaagaa acaaacata ggcttatcca cttctcagta    180 ttttaggtc tattgcttgt tggaattcat catcatcatc atcattga                 228
```

```
<210> SEQ ID NO 42
<211> LENGTH: 75
<212> TYPE: PRT
<213> ORGANISM: Artificial Sequence
<220> FEATURE:
<223> OTHER INFORMATION: construct GST_TM4SF20_N2

<400> SEQUENCE: 42
```

Gly Ser Ser Asp Ile His Pro Glu Ser Phe Asn Leu Gln Trp Phe Phe
1               5                   10                  15

Asn Asp Ser Cys Ala Pro Pro Thr Gly Phe Asn Lys Pro Thr Ser Asn
            20                  25                  30

Asp Thr Met Ala Ser Gly Trp Arg Ala Ser Ser Phe His Phe Asp Ser
        35                  40                  45

Glu Glu Asn Lys His Arg Leu Ile His Phe Ser Val Phe Leu Gly Leu
    50                  55                  60

Leu Leu Val Gly Ile His His His His His His
65                  70                  75

```
<210> SEQ ID NO 43
<211> LENGTH: 177
<212> TYPE: DNA
```

<210> SEQ ID NO 43
<211> LENGTH: 177
<212> TYPE: DNA
<213> ORGANISM: Artificial Sequence
<220> FEATURE:
<223> OTHER INFORMATION: construct GST_TM4SF20_N3

<400> SEQUENCE: 43

```
ggatcctgtg cacctcctac tggtttcaat aaacccacca gtaacgacac catggcgagt      60
ggctggagag catctagttt ccacttcgat tctgaagaaa acaaacatag gcttatccac     120
ttctcagtat ttttaggtct attgcttgtt ggaattcatc atcatcatca tcattga        177
```

<210> SEQ ID NO 44
<211> LENGTH: 58
<212> TYPE: PRT
<213> ORGANISM: Artificial Sequence
<220> FEATURE:
<223> OTHER INFORMATION: construct GST_TM4SF20_N3

<400> SEQUENCE: 44

```
Gly Ser Cys Ala Pro Pro Thr Gly Phe Asn Lys Pro Thr Ser Asn Asp
1               5                   10                  15

Thr Met Ala Ser Gly Trp Arg Ala Ser Ser Phe His Phe Asp Ser Glu
            20                  25                  30

Glu Asn Lys His Arg Leu Ile His Phe Ser Val Phe Leu Gly Leu Leu
        35                  40                  45

Leu Val Gly Ile His His His His His His
    50                  55
```

<210> SEQ ID NO 45
<211> LENGTH: 279
<212> TYPE: DNA
<213> ORGANISM: Artificial Sequence
<220> FEATURE:
<223> OTHER INFORMATION: construct GST_TM4SF20_C1

<400> SEQUENCE: 45

```
ggatcctgca tgctgatatc catccaggct ctcttaaaag gtcctctcat gtgtaattct      60
ccaagcaaca gtaatgccaa ttgtgaattt tcattgaaaa acatcagtga cattcatcca     120
gaatccttca acttgcagtg gttttttcaat gactcttgtg cacctcctac tggtttcaat    180
aaacccacca gtaacgacac catggcgagt ggctggagag catctagttt ccacttcgat     240
tctgaagaaa acaaacatca tcatcatcat catcattga                            279
```

<210> SEQ ID NO 46
<211> LENGTH: 92
<212> TYPE: PRT
<213> ORGANISM: Artificial Sequence
<220> FEATURE:
<223> OTHER INFORMATION: construct GST_TM4SF20_C1

<400> SEQUENCE: 46

```
Gly Ser Cys Met Leu Ile Ser Ile Gln Ala Leu Leu Lys Gly Pro Leu
1               5                   10                  15

Met Cys Asn Ser Pro Ser Asn Ser Ala Asn Cys Glu Phe Ser Leu
            20                  25                  30

Lys Asn Ile Ser Asp Ile His Pro Glu Ser Phe Asn Leu Gln Trp Phe
        35                  40                  45

Phe Asn Asp Ser Cys Ala Pro Pro Thr Gly Phe Asn Lys Pro Thr Ser
    50                  55                  60

Asn Asp Thr Met Ala Ser Gly Trp Arg Ala Ser Ser Phe His Phe Asp
65                  70                  75                  80
```

Ser Glu Glu Asn Lys His His His His His His
                85                  90

<210> SEQ ID NO 47
<211> LENGTH: 228
<212> TYPE: DNA
<213> ORGANISM: Artificial Sequence
<220> FEATURE:
<223> OTHER INFORMATION: construct GST_TM4SF20_C2

<400> SEQUENCE: 47

```
ggatcctgca tgctgatatc catccaggct ctcttaaaag gtcctctcat gtgtaattct      60
ccaagcaaca gtaatgccaa ttgtgaattt tcattgaaaa acatcagtga cattcatcca     120
gaatccttca acttgcagtg gttttttcaat gactcttgtg cacctcctac tggtttcaat   180
aaacccacca gtaacgacac catggcgcat catcatcatc atcattga                  228
```

<210> SEQ ID NO 48
<211> LENGTH: 75
<212> TYPE: PRT
<213> ORGANISM: Artificial Sequence
<220> FEATURE:
<223> OTHER INFORMATION: construct GST_TM4SF20_C2

<400> SEQUENCE: 48

Gly Ser Cys Met Leu Ile Ser Ile Gln Ala Leu Leu Lys Gly Pro Leu
1               5                   10                  15

Met Cys Asn Ser Pro Ser Asn Ser Asn Ala Asn Cys Glu Phe Ser Leu
            20                  25                  30

Lys Asn Ile Ser Asp Ile His Pro Glu Ser Phe Asn Leu Gln Trp Phe
        35                  40                  45

Phe Asn Asp Ser Cys Ala Pro Pro Thr Gly Phe Asn Lys Pro Thr Ser
    50                  55                  60

Asn Asp Thr Met Ala His His His His His His
65                  70                  75

<210> SEQ ID NO 49
<211> LENGTH: 177
<212> TYPE: DNA
<213> ORGANISM: Artificial Sequence
<220> FEATURE:
<223> OTHER INFORMATION: construct GST_TM4SF20_C3

<400> SEQUENCE: 49

```
ggatcctgca tgctgatatc catccaggct ctcttaaaag gtcctctcat gtgtaattct      60
ccaagcaaca gtaatgccaa ttgtgaattt tcattgaaaa acatcagtga cattcatcca     120
gaatccttca acttgcagtg gttttttcaat gactctcatc atcatcatca tcattga      177
```

<210> SEQ ID NO 50
<211> LENGTH: 58
<212> TYPE: PRT
<213> ORGANISM: Artificial Sequence
<220> FEATURE:
<223> OTHER INFORMATION: construct GST_TM4SF20_C3

<400> SEQUENCE: 50

Gly Ser Cys Met Leu Ile Ser Ile Gln Ala Leu Leu Lys Gly Pro Leu
1               5                   10                  15

Met Cys Asn Ser Pro Ser Asn Ser Asn Ala Asn Cys Glu Phe Ser Leu
            20                  25                  30

Lys Asn Ile Ser Asp Ile His Pro Glu Ser Phe Asn Leu Gln Trp Phe

-continued

```
                  35                  40                  45
Phe Asn Asp Ser His His His His His
        50                  55

<210> SEQ ID NO 51
<211> LENGTH: 21
<212> TYPE: DNA
<213> ORGANISM: Artificial Sequence
<220> FEATURE:
<223> OTHER INFORMATION: synthesized oligonucleotide MHC-IgG1

<400> SEQUENCE: 51
gggccagtgg atagacagat g                                              21

<210> SEQ ID NO 52
<211> LENGTH: 24
<212> TYPE: DNA
<213> ORGANISM: Artificial Sequence
<220> FEATURE:
<223> OTHER INFORMATION: synthesized oligonucleotide MHC-IgG2a

<400> SEQUENCE: 52
caggggccag tggatagacc gatg                                           24

<210> SEQ ID NO 53
<211> LENGTH: 24
<212> TYPE: DNA
<213> ORGANISM: Artificial Sequence
<220> FEATURE:
<223> OTHER INFORMATION: synthesized oligonucleotide MHC-IgG2b

<400> SEQUENCE: 53
caggggccag tggatagact gatg                                           24

<210> SEQ ID NO 54
<211> LENGTH: 23
<212> TYPE: DNA
<213> ORGANISM: Artificial Sequence
<220> FEATURE:
<223> OTHER INFORMATION: synthesized oligonucleotide MLC-kappa

<400> SEQUENCE: 54
gctcactgga tggtgggaag atg                                            23

<210> SEQ ID NO 55
<211> LENGTH: 357
<212> TYPE: DNA
<213> ORGANISM: Homo sapiens
<223> OTHER INFORMATION: B8 H V

<400> SEQUENCE: 55
cgggtgcagc tgaaggagtc aggacctgac cttgtgcagc cctcacagac cctgtctctc    60
acctgcactg tctctggggtt ctcattaacc aactatggtg ttcactggat tcgccagcct  120
ccaggaaagg gactggagtg gtgggaaca gtgggctggg atgacaaaaa atattataat    180
tcagttctaa aatctcgact gagcatcaac aggatacct ccaagaacca gtttttctta    240
aaactgagca gtctgcaaac tgaagacaca gccatgtact actgtacccc gtactacgat    300
ggtagcccct atgttatgga ctactggggt caaggaacct cagtcaccgt ctcctca       357

<210> SEQ ID NO 56
<211> LENGTH: 119
<212> TYPE: PRT
<213> ORGANISM: Homo sapiens
```

<223> OTHER INFORMATION: B8 H V

<400> SEQUENCE: 56

Arg Val Gln Leu Lys Glu Ser Gly Pro Asp Leu Val Gln Pro Ser Gln
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Val
        35                  40                  45

Gly Thr Val Gly Trp Asp Asp Lys Tyr Tyr Asn Ser Val Leu Lys
    50                  55                  60

Ser Arg Leu Ser Ile Asn Arg Asp Thr Ser Lys Asn Gln Val Phe Leu
65                  70                  75                  80

Lys Leu Ser Ser Leu Gln Thr Glu Asp Thr Ala Met Tyr Tyr Cys Thr
                85                  90                  95

Pro Tyr Tyr Asp Gly Ser Pro Tyr Val Met Asp Tyr Trp Gly Gln Gly
            100                 105                 110

Thr Ser Val Thr Val Ser Ser
        115

<210> SEQ ID NO 57
<211> LENGTH: 336
<212> TYPE: DNA
<213> ORGANISM: Homo sapiens
<223> OTHER INFORMATION: B8 L V

<400> SEQUENCE: 57
gacattgtga tgtcacagtc tccatcctcc ctggctgtgt cagcaggaga aaaggtcact    60
atgacctgca aatccagtca gagtctgttc gacagtggaa cccgaaagaa ctacttggct   120
tggtaccagc agaaaccagg gcagtctcct aaactgctga tctactgggc atccactagg   180
gagtctgggg tccctgatcg cttcacaggc agtggatctg ggacagattt cactctcacc   240
atcagcagtg tgcaggctga agacctggca gtttattact gcaagcaatc ttattatctg   300
ctcacgttcg gtgctgggac caagctggag ctgaaa                             336

<210> SEQ ID NO 58
<211> LENGTH: 112
<212> TYPE: PRT
<213> ORGANISM: Homo sapiens
<223> OTHER INFORMATION: B8 L V

<400> SEQUENCE: 58

Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Phe Asp Ser
            20                  25                  30

Gly Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Leu Thr Phe Gly Ala Gly Thr Lys Leu Glu Leu Lys
            100                 105                 110

<210> SEQ ID NO 59
<211> LENGTH: 357
<212> TYPE: DNA
<213> ORGANISM: Homo sapiens
<223> OTHER INFORMATION: B11 H V

<400> SEQUENCE: 59

```
gaggtccagc tgcagcagtc tggacctgag ctggtaaagc ctggggcttc agtgaagatg      60
tcctgcaagg cttctggata cagattcact aactatgtta tgcactgggt gaagcagaag     120
cctgggcagg gccttgagtg gattggatat attaatcctt acaatgctgg tactaagtac     180
aatgagaagt tcaaaggcaa ggccacactg acttcagaca atcctccag cacagcctac     240
atggagctca gcagcctgac ctctgaggac tctgcggtct attactgtgc aagaggggcg     300
ggatggtcac taaggtttgc tgactggggc caagggactc tggtcactgt ctctgca       357
```

<210> SEQ ID NO 60
<211> LENGTH: 119
<212> TYPE: PRT
<213> ORGANISM: Homo sapiens
<223> OTHER INFORMATION: B11 H V

<400> SEQUENCE: 60

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Arg Phe Thr Asn Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Ala Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Trp Ser Leu Arg Phe Ala Asp Trp Gly Gln Gly
            100                 105                 110

Thr Leu Val Thr Val Ser Ala
        115
```

<210> SEQ ID NO 61
<211> LENGTH: 321
<212> TYPE: DNA
<213> ORGANISM: Homo sapiens
<223> OTHER INFORMATION: B11 L V

<400> SEQUENCE: 61

```
gacatcctga tgacccaatc tccatcctcc atgtctgtat ctctgggaga cacagtcagc      60
atcacttgcc atgcaagtca gggcattagc agtaatatag gtggttgca gcagaaacca     120
gggaaatcat ttaagggcct gatctatctt gcaaccaact ggaagatgg agttccatca     180
aggttcagtg gcagtggatc tggagcagat tattctctca ccatcaccag cctggaatct     240
gaagattttg cagtctatta ctgtgtacag tatagtcagt ttcctcggac gttcggtgga     300
ggcaccaagc tagaaatcaa a                                                321
```

<210> SEQ ID NO 62
<211> LENGTH: 107
<212> TYPE: PRT

<213> ORGANISM: Homo sapiens
<223> OTHER INFORMATION: B11 L V

<400> SEQUENCE: 62

```
Asp Ile Leu Met Thr Gln Ser Pro Ser Ser Met Ser Val Ser Leu Gly
1               5                   10                  15

Asp Thr Val Ser Ile Thr Cys His Ala Ser Gln Gly Ile Ser Ser Asn
            20                  25                  30

Ile Gly Trp Leu Gln Gln Lys Pro Gly Lys Ser Phe Lys Gly Leu Ile
        35                  40                  45

Tyr Leu Ala Thr Asn Leu Glu Asp Gly Val Pro Ser Arg Phe Ser Gly
50                  55                  60

Ser Gly Ser Gly Ala Asp Tyr Ser Leu Thr Ile Thr Ser Leu Glu Ser
65                  70                  75                  80

Glu Asp Phe Ala Val Tyr Tyr Cys Val Gln Tyr Ser Gln Phe Pro Arg
                85                  90                  95

Thr Phe Gly Gly Gly Thr Lys Leu Glu Ile Lys
            100                 105
```

<210> SEQ ID NO 63
<211> LENGTH: 342
<212> TYPE: DNA
<213> ORGANISM: Homo sapiens
<223> OTHER INFORMATION: B12 H V

<400> SEQUENCE: 63

```
caggtgcagc tgaaggagtc aggacctgac cttgtgcagc cctcacagac cctgtctctc      60
acctgcactg tctctggatt ctcattaacc aactatggtg ttcactgggt tcgccagcct     120
ccaggaaagg gactggagtg gtgggaaca atgggctggg atgacaaaaa atattataat      180
tcagctctaa aatctcgact gagcatcagc agggatacct ccaagaacca gttttcttta    240
aaactgagca gtctgcaaac tgaagacaca gccatgtact actgtactag aaatgttaat    300
tttgactact ggggccaagg caccactctc acagtctcct ca                       342
```

<210> SEQ ID NO 64
<211> LENGTH: 114
<212> TYPE: PRT
<213> ORGANISM: Homo sapiens
<223> OTHER INFORMATION: B12 H V

<400> SEQUENCE: 64

```
Gln Val Gln Leu Lys Glu Ser Gly Pro Asp Leu Val Gln Pro Ser Gln
1               5                   10                  15

Thr Leu Ser Leu Thr Cys Thr Val Ser Gly Phe Ser Leu Thr Asn Tyr
            20                  25                  30

Gly Val His Trp Val Arg Gln Pro Pro Gly Lys Gly Leu Glu Trp Val
        35                  40                  45

Gly Thr Met Gly Trp Asp Asp Lys Lys Tyr Tyr Asn Ser Ala Leu Lys
    50                  55                  60

Ser Arg Leu Ser Ile Ser Arg Asp Thr Ser Lys Asn Gln Val Phe Leu
65                  70                  75                  80

Lys Leu Ser Ser Leu Gln Thr Glu Asp Thr Ala Met Tyr Tyr Cys Thr
                85                  90                  95

Arg Asn Val Asn Phe Asp Tyr Trp Gly Gln Gly Thr Thr Leu Thr Val
            100                 105                 110

Ser Ser
```

<210> SEQ ID NO 65
<211> LENGTH: 336
<212> TYPE: DNA
<213> ORGANISM: Homo sapiens
<223> OTHER INFORMATION: B12 L V

<400> SEQUENCE: 65

```
gatgttgtga tgacccagac tccactcact ttgtcggtta ccattggaca accagcctcc      60
atctcttgca agtcaagtca gagcctctta gatggtgatg aaagacata  tttgaattgg     120
ttgttacaga ggccaggcca gtctccaagg cgcctaatct atctggtgtc taaactggac    180
tctggagtcc ctgacaggtt cactggcagt ggatcaggga cagatttcac actgaaaatc    240
agcagagtgg aggctgagga tttgggagtt tattattgct ggcaaggtac acatttcct     300
cccacgttcg gtgctgggac caagctggag ctgaaa                              336
```

<210> SEQ ID NO 66
<211> LENGTH: 112
<212> TYPE: PRT
<213> ORGANISM: Homo sapiens
<223> OTHER INFORMATION: B12 L V

<400> SEQUENCE: 66

Asp Val Val Met Thr Gln Thr Pro Leu Thr Leu Ser Val Thr Ile Gly
1               5                   10                  15
Gln Pro Ala Ser Ile Ser Cys Lys Ser Ser Gln Ser Leu Leu Asp Gly
            20                  25                  30
Asp Gly Lys Thr Tyr Leu Asn Trp Leu Leu Gln Arg Pro Gly Gln Ser
        35                  40                  45
Pro Arg Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Trp Gln Gly
                85                  90                  95
Thr His Phe Pro Pro Thr Phe Gly Ala Gly Thr Lys Leu Glu Leu Lys
            100                 105                 110

<210> SEQ ID NO 67
<211> LENGTH: 357
<212> TYPE: DNA
<213> ORGANISM: Homo sapiens
<223> OTHER INFORMATION: B15 H V

<400> SEQUENCE: 67

```
cgggtgcagc tgaaggagtc aggacctgac cttgtgcagc cctcacagac cctgtctctc      60
acctgcactg tctctgggtt ctcattaacc aactatggtg ttcactggat tcgccagcct    120
ccaggaaagg gactggagtg gctgggaaca gtgggctggg atgacaaaaa atattataat    180
tcagttctaa aatctcgact gagcatcaac agggatacct ccaagaacca gttttctta    240
aaactgagca gtctccaaac tgaagacaca gccatgtact actgtacccc gtactacgat    300
ggtagcccct atgttatgga ctactggggt caaggaacct cagtcaccgt ctcctca       357
```

<210> SEQ ID NO 68
<211> LENGTH: 119
<212> TYPE: PRT
<213> ORGANISM: Homo sapiens
<223> OTHER INFORMATION: B15 H V -continued

<400> SEQUENCE: 68

Arg Val Gln Leu Lys Glu Ser Gly Pro Asp Leu Val Gln Pro Ser Gln
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Val
        35                  40                  45

Gly Thr Val Gly Trp Asp Asp Lys Lys Tyr Tyr Asn Ser Val Leu Lys
    50                  55                  60

Ser Arg Leu Ser Ile Asn Arg Asp Thr Ser Lys Asn Gln Val Phe Leu
65                  70                  75                  80

Lys Leu Ser Ser Leu Gln Thr Glu Asp Thr Ala Met Tyr Tyr Cys Thr
                85                  90                  95

Pro Tyr Tyr Asp Gly Ser Pro Tyr Val Met Asp Tyr Trp Gly Gln Gly
            100                 105                 110

Thr Ser Val Thr Val Ser Ser
        115

<210> SEQ ID NO 69
<211> LENGTH: 336
<212> TYPE: DNA
<213> ORGANISM: Homo sapiens
<223> OTHER INFORMATION: B15 L V

<400> SEQUENCE: 69
gacattgtga tgtcacagtc tccatcctcc ctggctgtgt cagcaggaga aaaggtcact      60
atgacctgca atccagtca gagtctgttc gacagtggaa cccgaaagaa ctacttggct     120
tggtaccagc agaaaccagg gcagtctcct aaactgctga tctactgggc atccactagg     180
gagtctgggg tccctgatcg cttcacaggc agtggatctg ggacagattt cactctcacc     240
atcagcagtg tgcaggctga agacctggca gtttattact gcaagcaatc ttattatctg     300
ctcacgttcg gtgctgggac caagctggag ctgaaa                               336

<210> SEQ ID NO 70
<211> LENGTH: 112
<212> TYPE: PRT
<213> ORGANISM: Homo sapiens
<223> OTHER INFORMATION: B15 L V

<400> SEQUENCE: 70

Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Phe Asp Ser
            20                  25                  30

Gly Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Tyr Leu Leu Thr Phe Gly Ala Gly Thr Lys Leu Glu Leu Lys
            100                 105                 110

<210> SEQ ID NO 71

```
<211> LENGTH: 354
<212> TYPE: DNA
<213> ORGANISM: Homo sapiens
<223> OTHER INFORMATION: C7 H V

<400> SEQUENCE: 71
caggtgcagc tgaaggagtc aggacctgac cttgtgcagc cctcacagac cctgtctctc    60
acctgcactg tctctgggtt ctcattatcc agctatggtg ttcactgggt tcgccagcct   120
ccaggaaagg gactagagtg ggtgggaaca atgggctggg atgacaaaaa atattataat   180
tcagctctaa actctcgact gagcctcagc aggatacct ccaagaacca ggttttctta    240
aaactgagca gtctgcaaac tgaagacaca gccatgtact actgtactag agattattac   300
tccgatggtt cctttgctta ctggggccaa gggactctgg tcactgtctc tgca         354

<210> SEQ ID NO 72
<211> LENGTH: 118
<212> TYPE: PRT
<213> ORGANISM: Homo sapiens
<223> OTHER INFORMATION: C7 H V

<400> SEQUENCE: 72

Gln Val Gln Leu Lys Glu Ser Gly Pro Asp Leu Val Gln Pro Ser Gln
1               5                  10                  15

Thr Leu Ser Leu Thr Cys Thr Val Ser Gly Phe Ser Leu Ser Ser Tyr
            20                  25                  30

Gly Val His Trp Val Arg Gln Pro Pro Gly Lys Gly Leu Glu Trp Val
        35                  40                  45

Gly Thr Met Gly Trp Asp Asp Lys Lys Tyr Tyr Asn Ser Ala Leu Asn
    50                  55                  60

Ser Arg Leu Ser Leu Ser Arg Asp Thr Ser Lys Asn Gln Val Phe Leu
65                  70                  75                  80

Lys Leu Ser Ser Leu Gln Thr Glu Asp Thr Ala Met Tyr Tyr Cys Thr
                85                  90                  95

Arg Asp Tyr Tyr Ser Asp Gly Ser Phe Ala Tyr Trp Gly Gln Gly Thr
            100                 105                 110

Leu Val Thr Val Ser Ala
        115

<210> SEQ ID NO 73
<211> LENGTH: 336
<212> TYPE: DNA
<213> ORGANISM: Homo sapiens
<223> OTHER INFORMATION: C7 L V

<400> SEQUENCE: 73
gatgttttga tgacccaaac tccactctcc ctgcctgtca gtcttggaga tcaagcctcc    60
atctcttgca aatctagtca gagtattgta catagtgatg aaacaccta tttacaatgg    120 tacctgcaga aaccaggcca gtctccaaag ctcctgatct acaaagtttc caaccgattt   180 tctgggtcc cagacaggtt cagtggcagt ggatcaggga cagatttcac actcaagatc    240
agcagagtgg aggctgagga tctgggaatt tattactgct ttcaaggttc acatgttcct   300
ccaacgttcg gcacgggac aaaattggaa ataaaa                               336

<210> SEQ ID NO 74
<211> LENGTH: 112
<212> TYPE: PRT
<213> ORGANISM: Homo sapiens
<223> OTHER INFORMATION: C7 L V
```

<400> SEQUENCE: 74

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Asp Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Thr Gly Thr Lys Leu Glu Ile Lys
            100                 105                 110

<210> SEQ ID NO 75
<211> LENGTH: 354
<212> TYPE: DNA
<213> ORGANISM: Homo sapiens
<223> OTHER INFORMATION: C9 H V

<400> SEQUENCE: 75
caggtgcagc tgaaggagtc aggacctgac cttgtgcagc cctcacagac cctgtctctc      60
acctgcactg tctctggggtt ctcattatcc agctatggtg ttcactgggt tcgccagcct    120
ccaggaaagg gactagagtg ggtgggaaca atgggctggg atgacaaaaa atattataat    180
tcagctctaa actctcgact gagcctcagc agggatacct caagaaccca ggttttctta    240
aaactgagca gtctgcaaac tgaagacaca gccatgtact actgtactag agattattac    300
tccgatggtt cctttgctta ctggggccaa gggactctgg tcactgtctc tgca          354

<210> SEQ ID NO 76
<211> LENGTH: 118
<212> TYPE: PRT
<213> ORGANISM: Homo sapiens
<223> OTHER INFORMATION: C9 H V

<400> SEQUENCE: 76

Gln Val Gln Leu Lys Glu Ser Gly Pro Asp Leu Val Gln Pro Ser Gln
1               5                   10                  15

Thr Leu Ser Leu Thr Cys Thr Val Ser Gly Phe Ser Leu Ser Ser Tyr
            20                  25                  30

Gly Val His Trp Val Arg Gln Pro Pro Gly Lys Gly Leu Glu Trp Val
        35                  40                  45

Gly Thr Met Gly Trp Asp Asp Lys Lys Tyr Tyr Asn Ser Ala Leu Asn
    50                  55                  60

Ser Arg Leu Ser Leu Ser Arg Asp Thr Ser Lys Asn Gln Val Phe Leu
65                  70                  75                  80

Lys Leu Ser Ser Leu Gln Thr Glu Asp Thr Ala Met Tyr Tyr Cys Thr
                85                  90                  95

Arg Asp Tyr Tyr Ser Asp Gly Ser Phe Ala Tyr Trp Gly Gln Gly Thr
            100                 105                 110

Leu Val Thr Val Ser Ala
        115

<210> SEQ ID NO 77
<211> LENGTH: 336
<212> TYPE: DNA
<213> ORGANISM: Homo sapiens
<223> OTHER INFORMATION: C9 L V

<400> SEQUENCE: 77

```
gatgttttga tgacccaaac tccactctcc ctgcctgtca gtcttggaga tcaagcctcc    60
atctcttgca aatctagtca gagtattgta catagtgatg aaacaccta tttacaatgg   120
tacctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggaatt tattactgct ttcaaggttc acatgttcct   300
ccaacgttcg gcacggggac aaaattggaa ataaaa                            336
```

<210> SEQ ID NO 78
<211> LENGTH: 112
<212> TYPE: PRT
<213> ORGANISM: Homo sapiens
<223> OTHER INFORMATION: C9 L V

<400> SEQUENCE: 78

Asp Val Leu Met Thr Gln Thr Pro Leu Ser Leu Pro Val Ser Leu Gly
1               5                   10                  15

Asp Gln Ala Ser Ile Ser Cys Lys Ser Ser Gln Ser Ile Val His Ser
            20                  25                  30

Asp Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Pro Thr Phe Gly Thr Gly Thr Lys Leu Glu Ile Lys
            100                 105                 110

<210> SEQ ID NO 79
<211> LENGTH: 5
<212> TYPE: PRT
<213> ORGANISM: Homo sapiens
<223> OTHER INFORMATION: B8 H CDR1

<400> SEQUENCE: 79

Asn Tyr Gly Val His
1               5

<210> SEQ ID NO 80
<211> LENGTH: 16
<212> TYPE: PRT
<213> ORGANISM: Homo sapiens
<223> OTHER INFORMATION: B8 H CDR2

<400> SEQUENCE: 80

Thr Val Gly Trp Asp Asp Lys Lys Tyr Tyr Asn Ser Val Leu Lys Ser
1               5                   10                  15

<210> SEQ ID NO 81
<211> LENGTH: 11
<212> TYPE: PRT
<213> ORGANISM: Homo sapiens

<223> OTHER INFORMATION: B8 H CDR3

<400> SEQUENCE: 81

Tyr Tyr Asp Gly Ser Pro Tyr Val Met Asp Tyr
1               5                   10

<210> SEQ ID NO 82
<211> LENGTH: 17
<212> TYPE: PRT
<213> ORGANISM: Homo sapiens
<223> OTHER INFORMATION: B8 L CDR1

<400> SEQUENCE: 82

Lys Ser Ser Gln Ser Leu Phe Asp Ser Gly Thr Arg Lys Asn Tyr Leu
1               5                   10                  15

Ala

<210> SEQ ID NO 83
<211> LENGTH: 7
<212> TYPE: PRT
<213> ORGANISM: Homo sapiens
<223> OTHER INFORMATION: B8 L CDR2

<400> SEQUENCE: 83

Trp Ala Ser Thr Arg Glu Ser
1               5

<210> SEQ ID NO 84
<211> LENGTH: 8
<212> TYPE: PRT
<213> ORGANISM: Homo sapiens
<223> OTHER INFORMATION: B8 L CDR3

<400> SEQUENCE: 84

Lys Gln Ser Tyr Tyr Leu Leu Thr
1               5

<210> SEQ ID NO 85
<211> LENGTH: 5
<212> TYPE: PRT
<213> ORGANISM: Homo sapiens
<223> OTHER INFORMATION: B11 H CDR1

<400> SEQUENCE: 85

Asn Tyr Val Met His
1               5

<210> SEQ ID NO 86
<211> LENGTH: 17
<212> TYPE: PRT
<213> ORGANISM: Homo sapiens
<223> OTHER INFORMATION: B11 H CDR2

<400> SEQUENCE: 86

Tyr Ile Asn Pro Tyr Asn Ala Gly Thr Lys Tyr Asn Glu Lys Phe Lys
1               5                   10                  15

Gly

<210> SEQ ID NO 87
<211> LENGTH: 10
<212> TYPE: PRT
<213> ORGANISM: Homo sapiens
<223> OTHER INFORMATION: B11 H CDR3

<400> SEQUENCE: 87

Gly Ala Gly Trp Ser Leu Arg Phe Ala Asp
1               5                   10

<210> SEQ ID NO 88
<211> LENGTH: 11
<212> TYPE: PRT
<213> ORGANISM: Homo sapiens
<223> OTHER INFORMATION: B11 L CDR1

<400> SEQUENCE: 88

His Ala Ser Gln Gly Ile Ser Ser Asn Ile Gly
1               5                   10

<210> SEQ ID NO 89
<211> LENGTH: 7
<212> TYPE: PRT
<213> ORGANISM: Homo sapiens
<223> OTHER INFORMATION: B11 L CDR2

<400> SEQUENCE: 89

Leu Ala Thr Asn Leu Glu Asp
1               5

<210> SEQ ID NO 90
<211> LENGTH: 9
<212> TYPE: PRT
<213> ORGANISM: Homo sapiens
<223> OTHER INFORMATION: B11 L CDR3

<400> SEQUENCE: 90

Val Gln Tyr Ser Gln Phe Pro Arg Thr
1               5

<210> SEQ ID NO 91
<211> LENGTH: 5
<212> TYPE: PRT
<213> ORGANISM: Homo sapiens
<223> OTHER INFORMATION: B12 H CDR1

<400> SEQUENCE: 91

Asn Tyr Gly Val His
1               5

<210> SEQ ID NO 92
<211> LENGTH: 16
<212> TYPE: PRT
<213> ORGANISM: Homo sapiens
<223> OTHER INFORMATION: B12 H CDR2

<400> SEQUENCE: 92

Thr Met Gly Trp Asp Asp Lys Lys Tyr Tyr Asn Ser Ala Leu Lys Ser
1               5                   10                  15

<210> SEQ ID NO 93
<211> LENGTH: 6
<212> TYPE: PRT
<213> ORGANISM: Homo sapiens
<223> OTHER INFORMATION: B12 H CDR3

<400> SEQUENCE: 93

Asn Val Asn Phe Asp Tyr
1               5

<210> SEQ ID NO 94
<211> LENGTH: 16

```
<212> TYPE: PRT
<213> ORGANISM: Homo sapiens
<223> OTHER INFORMATION: B12 L CDR1

<400> SEQUENCE: 94

Lys Ser Ser Gln Ser Leu Leu Asp Gly Asp Gly Lys Thr Tyr Leu Asn
1               5                   10                  15

<210> SEQ ID NO 95
<211> LENGTH: 7
<212> TYPE: PRT
<213> ORGANISM: Homo sapiens
<223> OTHER INFORMATION: B12 L CDR2

<400> SEQUENCE: 95

Leu Val Ser Lys Leu Asp Ser
1               5

<210> SEQ ID NO 96
<211> LENGTH: 9
<212> TYPE: PRT
<213> ORGANISM: Homo sapiens
<223> OTHER INFORMATION: B12 L CDR3

<400> SEQUENCE: 96

Trp Gln Gly Thr His Phe Pro Pro Thr
1               5

<210> SEQ ID NO 97
<211> LENGTH: 5
<212> TYPE: PRT
<213> ORGANISM: Homo sapiens
<223> OTHER INFORMATION: B15 H CDR1

<400> SEQUENCE: 97

Asn Tyr Gly Val His
1               5

<210> SEQ ID NO 98
<211> LENGTH: 16
<212> TYPE: PRT
<213> ORGANISM: Homo sapiens
<223> OTHER INFORMATION: B15 H CDR2

<400> SEQUENCE: 98

Thr Val Gly Trp Asp Asp Lys Lys Tyr Tyr Asn Ser Val Leu Lys Ser
1               5                   10                  15

<210> SEQ ID NO 99
<211> LENGTH: 11
<212> TYPE: PRT
<213> ORGANISM: Homo sapiens
<223> OTHER INFORMATION: B15 H CDR3

<400> SEQUENCE: 99

Tyr Tyr Asp Gly Ser Pro Tyr Val Met Asp Tyr
1               5                   10

<210> SEQ ID NO 100
<211> LENGTH: 17
<212> TYPE: PRT
<213> ORGANISM: Homo sapiens
<223> OTHER INFORMATION: B15 L CDR1

<400> SEQUENCE: 100

Lys Ser Ser Gln Ser Leu Phe Asp Ser Gly Thr Arg Lys Asn Tyr Leu
```

```
1               5                  10                  15
Ala
```

<210> SEQ ID NO 101
<211> LENGTH: 7
<212> TYPE: PRT
<213> ORGANISM: Homo sapiens
<223> OTHER INFORMATION: B15 L CDR2

<400> SEQUENCE: 101

```
Trp Ala Ser Thr Arg Glu Ser
1               5
```

<210> SEQ ID NO 102
<211> LENGTH: 8
<212> TYPE: PRT
<213> ORGANISM: Homo sapiens
<223> OTHER INFORMATION: B15 L CDR3

<400> SEQUENCE: 102

```
Lys Gln Ser Tyr Tyr Leu Leu Thr
1               5
```

<210> SEQ ID NO 103
<211> LENGTH: 5
<212> TYPE: PRT
<213> ORGANISM: Homo sapiens
<223> OTHER INFORMATION: C7 H CDR1

<400> SEQUENCE: 103

```
Ser Tyr Gly Val His
1               5
```

<210> SEQ ID NO 104
<211> LENGTH: 16
<212> TYPE: PRT
<213> ORGANISM: Homo sapiens
<223> OTHER INFORMATION: C7 H CDR2

<400> SEQUENCE: 104

```
Thr Met Gly Trp Asp Asp Lys Lys Tyr Tyr Asn Ser Ala Leu Asn Ser
1               5                  10                  15
```

<210> SEQ ID NO 105
<211> LENGTH: 10
<212> TYPE: PRT
<213> ORGANISM: Homo sapiens
<223> OTHER INFORMATION: C7 H CDR3

<400> SEQUENCE: 105

```
Asp Tyr Tyr Ser Asp Gly Ser Phe Ala Tyr
1               5                  10
```

<210> SEQ ID NO 106
<211> LENGTH: 16
<212> TYPE: PRT
<213> ORGANISM: Homo sapiens
<223> OTHER INFORMATION: C7 L CDR1

<400> SEQUENCE: 106

```
Lys Ser Ser Gln Ser Ile Val His Ser Asp Gly Asn Thr Tyr Leu Gln
1               5                  10                  15
```

<210> SEQ ID NO 107
<211> LENGTH: 7

```
<212> TYPE: PRT
<213> ORGANISM: Homo sapiens
<223> OTHER INFORMATION: C7 L CDR2

<400> SEQUENCE: 107

Lys Val Ser Asn Arg Phe Ser
1               5

<210> SEQ ID NO 108
<211> LENGTH: 9
<212> TYPE: PRT
<213> ORGANISM: Homo sapiens
<223> OTHER INFORMATION: C7 L CDR3

<400> SEQUENCE: 108

Phe Gln Gly Ser His Val Pro Pro Thr
1               5

<210> SEQ ID NO 109
<211> LENGTH: 5
<212> TYPE: PRT
<213> ORGANISM: Homo sapiens
<223> OTHER INFORMATION: C9 H CDR1

<400> SEQUENCE: 109

Ser Tyr Gly Val His
1               5

<210> SEQ ID NO 110
<211> LENGTH: 16
<212> TYPE: PRT
<213> ORGANISM: Homo sapiens
<223> OTHER INFORMATION: C9 H CDR2

<400> SEQUENCE: 110

Thr Met Gly Trp Asp Asp Lys Lys Tyr Tyr Asn Ser Ala Leu Asn Ser
1               5                   10                  15

<210> SEQ ID NO 111
<211> LENGTH: 10
<212> TYPE: PRT
<213> ORGANISM: Homo sapiens
<223> OTHER INFORMATION: C9 H CDR3

<400> SEQUENCE: 111

Asp Tyr Tyr Ser Asp Gly Ser Phe Ala Tyr
1               5                   10

<210> SEQ ID NO 112
<211> LENGTH: 16
<212> TYPE: PRT
<213> ORGANISM: Homo sapiens
<223> OTHER INFORMATION: C9 L CDR1

<400> SEQUENCE: 112

Lys Ser Ser Gln Ser Ile Val His Ser Asp Gly Asn Thr Tyr Leu Gln
1               5                   10                  15

<210> SEQ ID NO 113
<211> LENGTH: 7
<212> TYPE: PRT
<213> ORGANISM: Homo sapiens
<223> OTHER INFORMATION: C9 L CDR2

<400> SEQUENCE: 113

Lys Val Ser Asn Arg Phe Ser
```

<210> SEQ ID NO 114
<211> LENGTH: 9
<212> TYPE: PRT
<213> ORGANISM: Homo sapiens
<223> OTHER INFORMATION: C9 L CDR3

<400> SEQUENCE: 114

Phe Gln Gly Ser His Val Pro Pro Thr
1               5

<210> SEQ ID NO 115
<211> LENGTH: 2310
<212> TYPE: DNA
<213> ORGANISM: Homo sapiens
<220> FEATURE:
<221> NAME/KEY: CDS
<222> LOCATION: (39)..(728)
<223> OTHER INFORMATION: human TM4SF20 (GenBank Accession No:NM_024795)

<400> SEQUENCE: 115

```
atagccactt tgacaacgtt tctgagccag gggtgacc atg acc tgc tgc gaa gga          56
                                         Met Thr Cys Cys Glu Gly
                                           1               5 tgg aca tcc tgc aat gga ttc agc ctg ctg gtt cta ctg ctg tta gga           104
Trp Thr Ser Cys Asn Gly Phe Ser Leu Leu Val Leu Leu Leu Leu Gly
             10                  15                  20 gta gtt ctc aat gcg ata cct cta att gtc agc tta gtt gag gaa gac           152
Val Val Leu Asn Ala Ile Pro Leu Ile Val Ser Leu Val Glu Glu Asp
         25                  30                  35 caa ttt tct caa aac ccc atc tct tgc ttt gag tgg tgg ttc cca gga           200
Gln Phe Ser Gln Asn Pro Ile Ser Cys Phe Glu Trp Trp Phe Pro Gly
     40                  45                  50 att ata gga gca ggt ctg atg gcc att cca gca aca aca atg tcc ttg           248
Ile Ile Gly Ala Gly Leu Met Ala Ile Pro Ala Thr Thr Met Ser Leu
55                  60                  65                  70 aca gca aga aaa aga gcg tgc tgc aac aac aga act gga atg ttt ctt           296
Thr Ala Arg Lys Arg Ala Cys Cys Asn Asn Arg Thr Gly Met Phe Leu
                 75                  80                  85 tca tca ctt ttc agt gtg atc aca gtc att ggt gct ctg tat tgc atg           344
Ser Ser Leu Phe Ser Val Ile Thr Val Ile Gly Ala Leu Tyr Cys Met
             90                  95                 100 ctg ata tcc atc cag gct ctc tta aaa ggt cct ctc atg tgt aat tct           392
Leu Ile Ser Ile Gln Ala Leu Leu Lys Gly Pro Leu Met Cys Asn Ser
        105                 110                 115 cca agc aac agt aat gcc aat tgt gaa ttt tca ttg aaa aac atc agt           440
Pro Ser Asn Ser Asn Ala Asn Cys Glu Phe Ser Leu Lys Asn Ile Ser
    120                 125                 130 gac att cat cca gaa tcc ttc aac ttg cag tgg ttt ttc aat gac tct           488
Asp Ile His Pro Glu Ser Phe Asn Leu Gln Trp Phe Phe Asn Asp Ser
135                 140                 145                 150 tgt gca cct cct act ggt ttc aat aaa ccc acc agt aac gac acc atg           536
Cys Ala Pro Pro Thr Gly Phe Asn Lys Pro Thr Ser Asn Asp Thr Met
                155                 160                 165 gcg agt ggc tgg aga gca tct agt ttc cac ttc gat tct gaa gaa aac           584
Ala Ser Gly Trp Arg Ala Ser Ser Phe His Phe Asp Ser Glu Glu Asn
            170                 175                 180 aaa cat agg ctt atc cac ttc tca gta ttt tta ggt cta ttg ctt gtt           632
Lys His Arg Leu Ile His Phe Ser Val Phe Leu Gly Leu Leu Leu Val
        185                 190                 195 gga att ctg gag gtc ctg ttt ggg ctc agt cag ata gtc atc ggt ttc           680
Gly Ile Leu Glu Val Leu Phe Gly Leu Ser Gln Ile Val Ile Gly Phe
```

```
Gly Ile Leu Glu Val Leu Phe Gly Leu Ser Gln Ile Val Ile Gly Phe
    200             205                 210 ctt ggc tgt ctg tgt gga gtc tct aag cga aga agt caa att gtg tag    728
Leu Gly Cys Leu Cys Gly Val Ser Lys Arg Arg Ser Gln Ile Val
215                 220                 225 tttaatggga ataaaatgta agtatcagta gtttgaatta atttgagaag tacacttgtt    788
ttcaaagtca tctttgagat gatttaaaaa atcaaccctt cacgtagaaa gcacgttgta    848
aatgcataac actctcatat cagtggttga tttgggaaag gtggagagaa ttttcaatta    908
gttttgtgtt gtactattca aattttttac ctcttcactg tgtgtagaga aggagaagg    968 gaaggaggat gagaaggaac ggaagtcatc ctgaaaataa agtacagga cttttttttt    1028 tttttttga dacagggtct caaaaaaggc tggagtacag tagtacagtg gtgctatctc    1088
agcttactgc agcctcaacc tcctgggctc aggtgattct cccatctcag cctccctagt    1148
agctgggact acaggtgcgt gccactatgc caagctaatt tttgtatttt tagtagagat    1208
gggggttttc catattgccc aggctggtcc cgaactcatg gactcaagtg atctgcctgc    1268
ctcagcctcc taaagtgctg cgattacagg catgagccat cgcgcctaaa ggacaggacc    1328
tttttattgt atttctttaa agaataaata cataaccTga atgcaatcaa gtctttagat    1388
ctaattctca gcttgcaggg aacactagga caaatccaaa aagtgggtca gcgggcacag    1448
aatggcccaa ttttcaacag gaaaatgtta taaaagaaaa atattttga gggaactgtt    1508 atagattaag agaatagagg catgtttcag ctaaacacat gtaaactttg tcagagataa    1568
ttgggaggag tatgtagaag aatcggatta ttgttaattt tggtaggtct gataatggtt    1628
ttatagtata aaggctgagt accccttatc caaaatgatt aagatcagaa gtgttttggc    1688
tttcacattt ttttggattt tggaattttg cctataataa tgagacatct tggggatggg    1748
atgcaagtct aaccacaaaa ttcatttatg tctcatacac actttgaaca cctggcctga    1808
aggtaatttc acacaatatt ttaaataact ttgtgcatga aacacaattt tgactgcatt    1868
ttgactgcaa ctcatcacat gaggtcaggt atggaatttt ccacttgtgg tgttacgtta    1928
ctggctcaaa aagttttgga tctcggagca ttctggattt tgaattttg gattagtgat    1988 gctcaacctg tatacagaaa tgtcctcatt tttaaaaaaa gaaatgcata tttatatgtt    2048
ttaaaattac ttcaaccaaa agcaacgggg agatgtttac tgttatattt aggtgacagg    2108
tacatggcaa ttcattatac cctcctattt tcctatgttt acattattca ttaattaaaa    2168
aacaatacct agaaaaaccc aagactttca aaagctattt tctatatgtg ccaatcttta    2228
aaaaacagga taacaagggt atttatcaca ttaaaatgtt gtaaaacagc aaagctaaaa    2288
atctaaaaaa aaaaaaaaaa aa                                            2310
```

<210> SEQ ID NO 116
<211> LENGTH: 229
<212> TYPE: PRT
<213> ORGANISM: Homo sapiens
<223> OTHER INFORMATION: human TM4SF20 (GenBank Accession No:NM_024795)

<400> SEQUENCE: 116

```
Met Thr Cys Cys Glu Gly Trp Thr Ser Cys Asn Gly Phe Ser Leu Leu
1               5                   10                  15

Val Leu Leu Leu Leu Gly Val Val Leu Asn Ala Ile Pro Leu Ile Val
                20                  25                  30

Ser Leu Val Glu Glu Asp Gln Phe Ser Gln Asn Pro Ile Ser Cys Phe
            35                  40                  45
```

-continued

```
Glu Trp Trp Phe Pro Gly Ile Ile Gly Ala Gly Leu Met Ala Ile Pro
 50                  55                  60

Ala Thr Thr Met Ser Leu Thr Ala Arg Lys Arg Ala Cys Cys Asn Asn
 65                  70                  75                  80

Arg Thr Gly Met Phe Leu Ser Ser Leu Phe Ser Val Ile Thr Val Ile
                 85                  90                  95

Gly Ala Leu Tyr Cys Met Leu Ile Ser Ile Gln Ala Leu Leu Lys Gly
                100                 105                 110

Pro Leu Met Cys Asn Ser Pro Ser Asn Ser Asn Ala Asn Cys Glu Phe
                115                 120                 125

Ser Leu Lys Asn Ile Ser Asp Ile His Pro Glu Ser Phe Asn Leu Gln
130                 135                 140

Trp Phe Phe Asn Asp Ser Cys Ala Pro Pro Thr Gly Phe Asn Lys Pro
145                 150                 155                 160

Thr Ser Asn Asp Thr Met Ala Ser Gly Trp Arg Ala Ser Ser Phe His
                165                 170                 175

Phe Asp Ser Glu Glu Asn Lys His Arg Leu Ile His Phe Ser Val Phe
                180                 185                 190

Leu Gly Leu Leu Leu Val Gly Ile Leu Glu Val Leu Phe Gly Leu Ser
                195                 200                 205

Gln Ile Val Ile Gly Phe Leu Gly Cys Leu Cys Gly Val Ser Lys Arg
210                 215                 220

Arg Ser Gln Ile Val
225
```

```
<210> SEQ ID NO 117
<211> LENGTH: 4
<212> TYPE: PRT
<213> ORGANISM: Artificial
<220> FEATURE:
<223> OTHER INFORMATION: linker

<400> SEQUENCE: 117

Gly Gly Gly Ser
1

<210> SEQ ID NO 118
<211> LENGTH: 4
<212> TYPE: PRT
<213> ORGANISM: Artificial
<220> FEATURE:
<223> OTHER INFORMATION: linker

<400> SEQUENCE: 118

Ser Gly Gly Gly
1

<210> SEQ ID NO 119
<211> LENGTH: 5
<212> TYPE: PRT
<213> ORGANISM: Artificial
<220> FEATURE:
<223> OTHER INFORMATION: linker

<400> SEQUENCE: 119

Gly Gly Gly Gly Ser
1               5

<210> SEQ ID NO 120
<211> LENGTH: 5
<212> TYPE: PRT
```

```
<213> ORGANISM: Artificial
<220> FEATURE:
<223> OTHER INFORMATION: linker

<400> SEQUENCE: 120

Ser Gly Gly Gly Gly
1               5

<210> SEQ ID NO 121
<211> LENGTH: 6
<212> TYPE: PRT
<213> ORGANISM: Artificial
<220> FEATURE:
<223> OTHER INFORMATION: linker

<400> SEQUENCE: 121

Gly Gly Gly Gly Gly Ser
1               5

<210> SEQ ID NO 122
<211> LENGTH: 6
<212> TYPE: PRT
<213> ORGANISM: Artificial
<220> FEATURE:
<223> OTHER INFORMATION: linker

<400> SEQUENCE: 122

Ser Gly Gly Gly Gly Gly
1               5

<210> SEQ ID NO 123
<211> LENGTH: 7
<212> TYPE: PRT
<213> ORGANISM: Artificial
<220> FEATURE:
<223> OTHER INFORMATION: linker

<400> SEQUENCE: 123

Gly Gly Gly Gly Gly Gly Ser
1               5

<210> SEQ ID NO 124
<211> LENGTH: 7
<212> TYPE: PRT
<213> ORGANISM: Artificial
<220> FEATURE:
<223> OTHER INFORMATION: linker

<400> SEQUENCE: 124

Ser Gly Gly Gly Gly Gly Gly
1               5
```